US011690497B2

United States Patent
Sato et al.

(10) Patent No.: US 11,690,497 B2
(45) Date of Patent: Jul. 4, 2023

(54) LENS UNIT

(71) Applicants: Fujikura Ltd., Tokyo (JP); SEIKOH GIKEN Co., Ltd., Matsudo (JP)

(72) Inventors: Takao Sato, Sakura (JP); Hideo Shiratani, Sakura (JP); Kengo Takamizawa, Sakura (JP); Ryosuke Niwaki, Matsudo (JP); Tomomi Hirao, Matsudo (JP)

(73) Assignees: Fujikura Ltd.; SEIKOH GIKEN Co., Ltd.

( * ) Notice: Subject to any disclaimer, the term of this patent is extended or adjusted under 35 U.S.C. 154(b) by 398 days.

(21) Appl. No.: 16/695,201

(22) Filed: Nov. 26, 2019

(65) Prior Publication Data

US 2020/0178765 A1 Jun. 11, 2020

(30) Foreign Application Priority Data

Nov. 27, 2018 (JP) .................................. 2018-221512
Nov. 22, 2019 (JP) .................................. 2019-211340

(51) Int. Cl.
*A61B 1/00* (2006.01)
*A61B 1/05* (2006.01)
(Continued)

(52) U.S. Cl.
CPC ...... *A61B 1/00096* (2013.01); *A61B 1/00186* (2013.01); *A61B 1/05* (2013.01);
(Continued)

(58) Field of Classification Search
CPC .......... A61B 1/05; A61B 1/051; A61B 1/055; A61B 1/0008; A61B 1/00096;
(Continued)

(56) References Cited

U.S. PATENT DOCUMENTS 6,142,930 A * 11/2000 Ito ...................... A61B 1/00096
600/110
8,988,516 B2 * 3/2015 Sasamoto .......... G02B 27/0075
348/65

(Continued)

FOREIGN PATENT DOCUMENTS

JP   H05-323227 A    12/1993
JP   H10-211167 A     8/1998
(Continued)

*Primary Examiner* — Ryan N Henderson
(74) *Attorney, Agent, or Firm* — Yokoi & Co., U.S.A.; Toshiyuki Yokoi

(57) ABSTRACT

The present invention provides a lens unit having a cover member which does not cause deviation in precision and capable of being manufactured efficiently at low cost. In a lens unit 10A, side surfaces of a cover member 14a continuing from a front end surface 29 to a rear end surface located at a lens side are formed in a regular quadrangular prism, at least two of corners of the regular quadrangular prism are in contact with an inner peripheral surface 27 of a housing space 17 of a holder 11a for housing the cover member 14a, a gap 34 is formed between each of the side surfaces of the cover member 14a and the inner peripheral surface 27 of the holder 11a, and an effective area of a light beam is located inside a light receiving area having a regular quadrangular shape surrounded by an outer peripheral edge of the front end surface 29 of the cover member 14a.

17 Claims, 27 Drawing Sheets

(51) Int. Cl.
*G02B 23/24* (2006.01)
*G02B 5/00* (2006.01)

(52) U.S. Cl.
CPC .............. *A61B 1/051* (2013.01); *G02B 5/005* (2013.01); *G02B 23/243* (2013.01)

(58) Field of Classification Search
CPC ............ A61B 1/00097; A61B 1/00163; A61B 1/00165; A61B 1/002
See application file for complete search history.

(56) References Cited

U.S. PATENT DOCUMENTS

| | | | |
|---|---|---|---|
| 9,942,452 B2* | 4/2018 | Wei | A61B 1/0052 |
| 10,433,710 B1* | 10/2019 | Griffin | A61B 1/012 |
| 2005/0089286 A1 | 4/2005 | Hatori | |
| 2006/0262415 A1* | 11/2006 | Forkey | G02B 23/2476 359/642 |
| 2013/0172678 A1* | 7/2013 | Kennedy, II | A61B 1/051 600/109 |
| 2014/0036356 A1* | 2/2014 | Feinbloom | G02B 25/004 359/361 |
| 2015/0031955 A1 | 1/2015 | Avitsian et al. | |
| 2015/0035960 A1* | 2/2015 | Nakamura | G03B 17/17 348/76 |
| 2015/0062316 A1 | 3/2015 | Haraguchi et al. | |
| 2015/0238069 A1* | 8/2015 | Osada | G02B 23/2476 600/109 |
| 2016/0213239 A1* | 7/2016 | Fujii | A61B 1/00163 |
| 2016/0266373 A1* | 9/2016 | Sakai | A61B 1/04 |
| 2017/0059848 A1* | 3/2017 | Haraguchi | G02B 23/2469 |
| 2017/0064162 A1* | 3/2017 | Haraguchi | A61B 1/051 |
| 2017/0307872 A1* | 10/2017 | Hatase | H04N 23/51 |
| 2017/0322411 A1* | 11/2017 | Igarashi | G02B 23/2484 |
| 2018/0063387 A1* | 3/2018 | Wei | A61B 1/07 |
| 2018/0213207 A1* | 7/2018 | Wilson | A61B 1/041 |
| 2018/0303325 A1* | 10/2018 | Fujimori | A61B 1/04 |
| 2019/0076002 A1* | 3/2019 | Shimohata | H04N 23/00 |
| 2019/0082944 A1* | 3/2019 | Fujimori | H04N 23/50 |
| 2019/0086657 A1* | 3/2019 | Sueyoshi | A61B 1/051 |
| 2019/0142249 A1* | 5/2019 | Koyama | A61B 1/051 600/160 |
| 2019/0260917 A1* | 8/2019 | Yamamoto | H04N 23/54 |
| 2020/0364575 A1* | 11/2020 | Griffin | G06N 3/006 |

FOREIGN PATENT DOCUMENTS

| | | |
|---|---|---|
| JP | 2005-118294 A | 5/2005 |
| JP | 2014-176713 A | 9/2014 |
| JP | 2015-047277 A | 3/2015 |
| JP | 2017-099485 A | 6/2017 |
| JP | 2017-195964 A | 11/2017 |

\* cited by examiner

LENS UNIT

CROSS-REFERENCES TO RELATED APPLICATIONS

This patent specification is based on Japanese patent application, No. 2018-221512 filed on Nov. 27, 2018 in the Japan Patent Office and Japanese patent application, No. 2019-211340 filed on Nov. 22, 2019 in the Japan Patent Office, the entire contents of which are incorporated by reference herein.

BACKGROUND OF THE INVENTION

1. Field of the Invention

The present invention relates to a lens unit connected to an image pickup element.

2. Description of Related Art

Various medical endoscopes such as a brain endoscope, an otological endoscope, a thoracoscope and a laparoscope are used for diagnosis and treatment. In addition to the medical endoscopes, industrial endoscopes are used for various inspection. In the endoscopes, a lens unit is installed on a distal end of a sensor module (scope).

Conventionally, as shown in FIGS. 26, 27, a lens unit 50 used for a vascular endoscope is formed by a holder 51 having a housing space 52 formed in a circular cross-section and recessed from a front end to a rear end, a lens 53 housed in the housing space 52 of the holder 51, a copper diaphragm plate 54 housed in the housing space 52 of the holder 51 so as to be contacted with a front end surface of the lens 53, and a cover glass 55 housed in the housing space 52 of the holder 51 so as to be contacted with the copper diaphragm plate 54. A sensor module 56 having an image pickup element is arranged on the rearward of the holder 51. A medical device sheath using the above described lens unit is disclosed (shown in Patent Document 1).

Note that the cover glass 55 of the lens unit 50 used for vascular endoscope is a small-sized glass having a diameter of 1.0 to 1.2 mm, the cover glass 55 is formed in a cylindrical column from the front end surface to the rear end surface so that the cover glass 55 has a complete round cross-sectional shape, and an outer peripheral surface of the cover glass 55 is in contact with an inner peripheral surface of the holder 51 without gaps. The cover glass 55 is evenly chamfered at the corners where the front end surface and the outer peripheral surface intersect.

[Patent Document 1] Japanese Unexamined Patent Application Publication No. 2014-176713

BRIEF SUMMARY OF THE INVENTION

The conventional cover glass 55 of the lens unit 50 shown in FIGS. 26, 27 is a small-sized glass as already described. Thus, the glass material should be formed in a cylindrical column by polishing so that the cross-sectional shape is a completely round shape and the diameter is within the above described range. In addition, the corners should be evenly chamfered at the corners where the circular front end surface and the outer peripheral surface intersect. Accordingly, precision is required when the cross-sectional shape is made close to a complete roundness, the diameter is specified within the above described range, and the corners are evenly chamfered. Now, the above described cover glass 55 is manufactured by handwork of skilled artisans. However, the number of manufacturable products is limited. Thus, the manufacturing cost increases and a large number of defective products are produced due to a deviation in precision. Consequently, production efficiency of the lens unit 50 cannot be increased.

In addition, in the lens unit 50 shown in FIGS. 26, 27, although an effective area of a light beam extending from the lens 53 through a diaphragm of the copper diaphragm plate 54 to the front end surface (object side) of the cover glass 55 appears on the front end surface of the cover glass 55, an accurate image cannot be formed on the lens unit 50 if a part of the effective area of the light beam is displaced outside a circular light receiving area surrounded by a peripheral edge of the front end surface of the cover glass 55.

The present invention aims for providing a lens unit which can be manufactured at low cost without depending on skilled artisans. The lens unit has a cover member which does not cause deviation in precision. Thus, production efficiency can be increased. The present invention also aims for providing a lens unit which can form an accurate image since a part of the effective area of the light beam is not displaced outside the light receiving area surrounded by the peripheral edge of the front end surface of the cover member.

In order to solve the above described problems, a precondition of the present invention is a lens unit formed by a holder having a housing space, and a lens, a diaphragm means and a cover glass which are housed individually in the housing space of the holder having a circular cross-section.

The lens unit of the present invention having the above described precondition is characterized in that side surfaces of the cover member are formed in a polygonal prism (polygonal column, polygonal cylinder) with even-numbered corners, the side surfaces continuing from a front end surface to a rear end surface which is located nearer to the lens, at least two of the corners of the polygonal prism are in contact with an inner peripheral surface of the housing space of the holder for housing the cover member, a gap is formed between each of the side surfaces of the cover member and the inner peripheral surface of the holder in the lens unit, and an effective area of a light beam is located inside a light receiving area having a polygonal shape surrounded by a peripheral edge of the front end surface of the cover member.

As an example of the lens unit of the present invention, the side surfaces of the cover member are formed in a quadrangular (rectangular) prism, the side surfaces continuing from the front end surface to the rear end surface, at least two of the corners of the quadrangular prism of the cover member are in contact with the inner peripheral surface of the housing space, the gap is formed between each of the side surfaces of the quadrangular prism of the cover member and the inner peripheral surface of the holder in the lens unit, and the effective area of the light beam is circular and located inside the light receiving area having a quadrangular shape surrounded by the peripheral edge of the front end surface of the quadrangular prism of the cover member.

As another example of the lens unit of the present invention, the side surfaces of the cover member are formed in a hexagonal prism, the side surfaces continuing from the front end surface to the rear end surface, at least two of the corners of the hexagonal prism of the cover member are in contact with the inner peripheral surface of the housing space, the gap is formed between each of the side surfaces of the hexagonal prism of the cover member and the inner peripheral surface of the holder in the lens unit, and the effective area of the light beam is circular and located inside the light receiving area having a hexagonal shape surrounded by the peripheral edge of the front end surface of the hexagonal prism of the cover member.

As another example of the lens unit of the present invention, the side surfaces of the cover member are formed in an octagonal prism, the side surfaces continuing from the front end surface to the rear end surface, at least two of the corners of the octagonal prism of the cover member are in contact with the inner peripheral surface of the housing space, the gap is formed between each of the side surfaces of the octagonal prism of the cover member and the inner peripheral surface of the holder in the lens unit, and the effective area of the light beam is circular and located inside the light receiving area having an octagonal shape surrounded by the peripheral edge of the front end surface of the octagonal prism of the cover member.

As another example of the lens unit of the present invention, when at least one of the corners of the cover member is separated inward in a radial direction from the inner peripheral surface of the housing space at a predetermined separate distance in the lens unit, the predetermined separate distance between the corners and the inner peripheral surface of the housing space is 0.1 mm or less.

As another example of the lens unit of the present invention, the cover member is chamfered at the corners where the front end surface and each of the side surfaces intersect so that a chamfered surface is formed.

As another example of the lens unit of the present invention, a length of the chamfered surface of the cover member is 0.3 mm or less in a radial direction.

As another example of the lens unit of the present invention, an inner diameter of the housing space of the holder for housing the cover member is 0.4 mm to 8 mm.

As another example of the lens unit of the present invention, a thickness from the front end surface to the rear end surface of the cover member is 0.01 mm to 0.5 mm.

As another example of the lens unit of the present invention, an inner diameter of a diaphragm in the diaphragm means is 0.01 mm to 0.3 mm, and a field angle of the lens is 150° or less.

As another example of the lens unit of the present invention, a marking protrusion extending from the inner peripheral surface of the holder inward in a radial direction is extended to the gap formed between the side surfaces of the cover member and the inner peripheral surface of the holder.

As another example of the lens unit of the present invention, a filler is filled in the gap formed between each of the side surfaces of the cover member and the inner peripheral surface of the holder.

As another example of the lens unit of the present invention, the diaphragm means is a diaphragm pattern masked (formed) by photo-etching at least on one of the front end surface and the rear end surface of the cover member.

As another example of the lens unit of the present invention, the lens unit is installed on a distal end of a sensor module of an endoscope.

In the lens unit of the present invention, the cover member (cover glass or cover plastic) can be easily manufactured by cutting a glass material or molding a synthetic resin material so that the side surfaces continuing from the front end surface to the rear end surface are formed in a polygonal prism with even-numbered corners. Thus, handwork of artisans is not required for polishing the outer peripheral surface of the cover glass into a cylindrical column so that the cover glass has a complete round cross-sectional shape. Accordingly, the lens unit having the cover member formed in a polygonal prism with even-numbered corners can be mechanically and efficiently manufactured. In the lens unit, the cover member (cover glass or cover plastic) can be manufactured by cutting the glass material into the polygonal prism with even-numbered corners or molding the synthetic resin material into the polygonal prism with even-numbered corners. Thus, the cover member can be manufactured at low cost without depending on skilled artisans. In addition, the lens unit having the cover member which is formed in the polygonal prism and does not cause deviation in precision can be manufactured at low cost. Accordingly, production efficiency of the lens unit can be increased. In the lens unit, at least two of the even-numbered corners of the polygonal prism are in contact with an inner peripheral surface of the housing space of the holder for housing the cover member. Thus, the cover member formed in the polygonal prism can be fixed to the housing space of the holder while preventing the cover member from moving in the housing space of the holder. In the lens unit, the effective area of the light beam is located inside the light receiving area having the polygonal shape surrounded by the peripheral edge of the front end surface of the cover member. Thus, the accurate image can be formed on the lens unit since a part of the effective area of the light beam is not displaced outside the light receiving area having the polygonal shape.

In the lens unit described in claim 2 where the side surfaces of the cover member continuing from the front end surface to the rear end surface are formed in a quadrangular prism, the cover member (cover glass or cover plastic) can be easily manufactured by cutting a glass material or molding a synthetic resin material so that the side surfaces continuing from the front end surface to the rear end surface are formed in a quadrangular prism. Thus, handwork of artisans is not required for polishing the outer peripheral surface of the cover glass into a cylindrical column so that the cover glass has a complete round cross-sectional shape. Accordingly, the lens unit having the cover member formed in a quadrangular prism can be mechanically and efficiently manufactured. In the lens unit, the cover member can be manufactured by cutting the glass material into the quadrangular prism or molding the synthetic resin material into the quadrangular prism. Thus, the cover member can be manufactured at low cost without depending on skilled artisans. In addition, the lens unit having the cover member which is formed in the quadrangular prism and does not cause deviation in precision can be manufactured at low cost. Accordingly, production efficiency of the lens unit can be increased. In the lens unit, at least two of the corners of the quadrangular prism are in contact with an inner peripheral surface of the holder. Thus, the cover member formed in the quadrangular prism can be fixed to the housing space of the holder while preventing the cover member from moving in the housing space of the holder. In the lens unit, the effective area of the light beam is located inside the light receiving area having the quadrangular shape surrounded by the peripheral edge of the front end surface of the cover member. Thus, the accurate image can be formed on the lens unit since a part of the effective area of the light beam is not displaced outside the light receiving area having the quadrangular shape.

In the lens unit described in claim 3 where the side surfaces of the cover member continuing from the front end surface to the rear end surface are formed in a hexagonal prism, the cover member (cover glass or cover plastic) can be easily manufactured by cutting a glass material or molding a synthetic resin material so that the side surfaces continuing from the front end surface to the rear end surface are formed in a hexagonal prism. Thus, handwork of artisans is not required for polishing the outer peripheral surface of the cover glass into a cylindrical column so that the cover glass has a complete round cross-sectional shape. Accordingly, the lens unit having the cover member formed in a hexagonal prism can be mechanically and efficiently manufactured. In the lens unit, the cover member can be manufactured by cutting the glass material into the hexagonal prism or molding the synthetic resin material into the hexagonal prism. Thus, the cover member can be manufactured at low cost without depending on skilled artisans. In addition, the lens unit having the cover member which is formed in the hexagonal prism and does not cause deviation in precision can be manufactured at low cost. Accordingly, production efficiency of the lens unit can be increased. In the lens unit, at least two of the corners of the hexagonal prism are in contact with an inner peripheral surface of the holder. Thus, the cover member formed in the hexagonal prism can be fixed to the housing space of the holder while preventing the cover member from moving in the housing space of the holder. In the lens unit, the effective area of the light beam is located inside the light receiving area having the hexagonal shape surrounded by the peripheral edge of the front end surface of the cover member. Thus, the accurate image can be formed on the lens unit since a part of the effective area of the light beam is not displaced outside the light receiving area having the hexagonal shape.

In the lens unit described in claim 4 where the side surfaces of the cover member continuing from the front end surface to the rear end surface are formed in an octagonal prism, the cover member (cover glass or cover plastic) can be easily manufactured by cutting a glass material or molding a synthetic resin material into a cylindrical column so that the side surfaces continuing from the front end surface to the rear end surface are formed in an octagonal prism. Thus, handwork of artisans is not required for polishing the outer peripheral surface of the cover glass so that the cover glass has a complete round cross-sectional shape. Accordingly, the lens unit having the cover member formed in an octagonal prism can be mechanically and efficiently manufactured. In the lens unit, the cover member can be manufactured by cutting the glass material into the octagonal prism or molding the synthetic resin material into the octagonal prism. Thus, the cover member can be manufactured at low cost without depending on skilled artisans. In addition, the lens unit having the cover member which is formed in the octagonal prism and does not cause deviation in precision can be manufactured at low cost. Accordingly, production efficiency of the lens unit can be increased. In the lens unit, at least two of the corners of the octagonal prism are in contact with an inner peripheral surface of the holder. Thus, the cover member formed in the octagonal prism can be fixed to the housing space of the holder while preventing the cover member from moving in the housing space of the holder. In the lens unit, the effective area of the light beam is located inside the light receiving area having the octagonal shape surrounded by the peripheral edge of the front end surface of the cover member. Thus, the accurate image can be formed on the lens unit since a part of the effective area of the light beam is not displaced outside the light receiving area having the octagonal shape.

In the lens unit described in claim 5 where the separate distance between the corners and the inner peripheral surface of the housing space is 0.1 mm or less, if the separate length between the corners and the inner peripheral surface of the housing space exceeds 0.1 mm, a part of the effective area of the light beam may be displaced (protruded) outside the light receiving area surrounded by the peripheral edge of the front end surface of the cover member when the cover member is moved in the housing space. Thus, the accurate image cannot be formed on the lens unit. However, since the separate distance between the corners and the inner peripheral surface of the housing space is 0.1 mm or less, a part of the effective area of the light beam is not displaced (protruded) outside the light receiving area of the front end surface of the cover member even if the cover member (cover glass or cover plastic) is moved in the housing space. Thus, the accurate image can be formed on the lens unit.

In the lens unit described in claim 6 where the cover member is chamfered at the corners where the front end surface and each of the side surfaces intersect, when the side surfaces of the cover member (cover glass or cover plastic) is formed in a quadrangular prism, a hexagonal prism, an octagonal prism or other polygonal prism with even-numbered corners, the corners can be easily chamfered by cutting the corners where the front end surface of the cover member and each of the side surfaces intersect or molding the synthetic resin material. Accordingly, unexpected breakage and damage of the corners of the cover member (cover glass or cover plastic) formed in a quadrangular prism, a hexagonal prism, an octagonal prism or other polygonal prism with even-numbered corners can be prevented.

In the lens unit described in claim 7 where a length of the chamfered surface of the cover member is 0.3 mm or less in a radial direction, if the length of the chamfered surface exceeds 0.3 mm in the radial direction, the light receiving area surrounded by the peripheral edge of the front end surface of the cover member becomes small and a part of the effective area of the light beam may be located (displaced) outside the light receiving area surrounded by the peripheral edge of the front end surface of the cover member. Thus, the accurate image cannot be formed on the lens unit. However, since the length of the chamfered surface is 0.3 mm or less in the radial direction, the effective area of the light beam can be located inside the light receiving area of the front end surface of cover member (cover glass or cover plastic). Thus, the accurate image can be formed on the lens unit while preventing a part of the effective area of the light beam from being located (displaced) outside the light receiving area of the front end surface of the cover member.

In the lens unit described in claim 8 where an inner diameter of the housing space of the holder is 0.4 mm to 8 mm, since the inner diameter of the housing space is 0.4 mm to 8 mm, the lens unit can be small-sized. Thus, a small-sized lens unit capable of suitably connected to a small-sized image pickup element can be manufactured.

In the lens unit described in claim 9 where a thickness of the cover member is 0.01 mm to 0.5 mm, since the thickness of the cover member (cover glass or cover plastic) is 0.01 mm to 0.5 mm, the lens unit can be small-sized. Thus, a small-sized lens unit capable of suitably connected to a small-sized image pickup element can be manufactured and the effective area of the light beam can be located inside the light receiving area of the front end surface of the cover member. Accordingly, the accurate image can be formed on the lens unit while preventing a part of the effective area of the light beam from being located outside the light receiving area.

In the lens unit described in claim 10 where an inner diameter of a diaphragm in the diaphragm means is 0.01 mm to 0.3 mm and a field angle of the lens is 150° or less, since the inner diameter of the diaphragm of the diaphragm means is 0.01 mm to 0.3 mm and the field angle of the lens is 150° or less, the effective area of the light beam can be located inside the light receiving area of the front end surface of the cover member (cover glass or cover plastic). Thus, a part of the effective area of the light beam is not displaced outside the light receiving area. Accordingly, the accurate image can be formed on the lens unit.

In the lens unit described in claim 11 where a marking protrusion extending from the inner peripheral surface of the holder inward in a radial direction is formed, when the lens unit is arranged on a distal end of the sensor module (scope) and the marking protrusion is arranged on the top (upper) portion of the sensor module (scope) or the marking protrusion is arranged on the bottom (lower) portion of the sensor module (scope), for example, the top (upper) portion of the sensor module and the bottom (lower) portion of the sensor module can be easily confirmed by visually recognizing the marking protrusion. Accordingly, productivity of an image pickup module and workability of assembling to the endoscope can be improved.

In the lens unit described in claim 12 where a filler is filled in the gap formed between each of the side surfaces of the cover member and the inner peripheral surface of the holder, when the cover member (cover glass or cover plastic) is formed in a quadrangular prism, a hexagonal prism, an octagonal prism or other polygonal prism with even-numbered corners, the gap is formed between each of the side surfaces of the cover member and the inner peripheral surface of the holder and unnecessary light may be entered from the gap into the image pickup element of the sensor module. However, since the filler for blocking the light is filled in the gap between each of the side surfaces of the cover member and the inner peripheral surface of the holder, the light can be blocked. Accordingly, unnecessary light can be prevented from entering in the image pickup element.

In the lens unit described in claim 13 where the diaphragm means is a diaphragm pattern masked by photo-etching at least on one of the front end surface and the rear end surface of the cover member, a diaphragm means (diaphragm pattern) can be formed by photo-etching at least on one of the front end surface and the rear end surface of the cover member (cover glass or cover plastic) formed in a quadrangular prism, a hexagonal prism, an octagonal prism or other polygonal prism with even-numbered corners. Thus, it is not required to interpose a copper diaphragm plate between the lens and the cover member. Accordingly, the copper diaphragm plate can be omitted and labor and time for an assembling work can be reduced. In the lens unit described in claim 14 where the lens unit is installed on a distal end of a sensor module of an endoscope, the cover member (cover glass or cover plastic) can be easily manufactured by cutting a glass material into a quadrangular prism, a hexagonal prism, an octagonal prism or other polygonal prism with even-numbered corners or molding the synthetic resin material into a quadrangular prism, a hexagonal prism, an octagonal prism or other polygonal prism with even-numbered corners. Thus, the lens unit used for the sensor module of the endoscope can be easily manufactured. Accordingly, a small-sized lens unit suitably used for the sensor module of the endoscope can be mechanically manufactured at low cost.

DETAILED DESCRIPTION OF THE INVENTION

Figure 1:
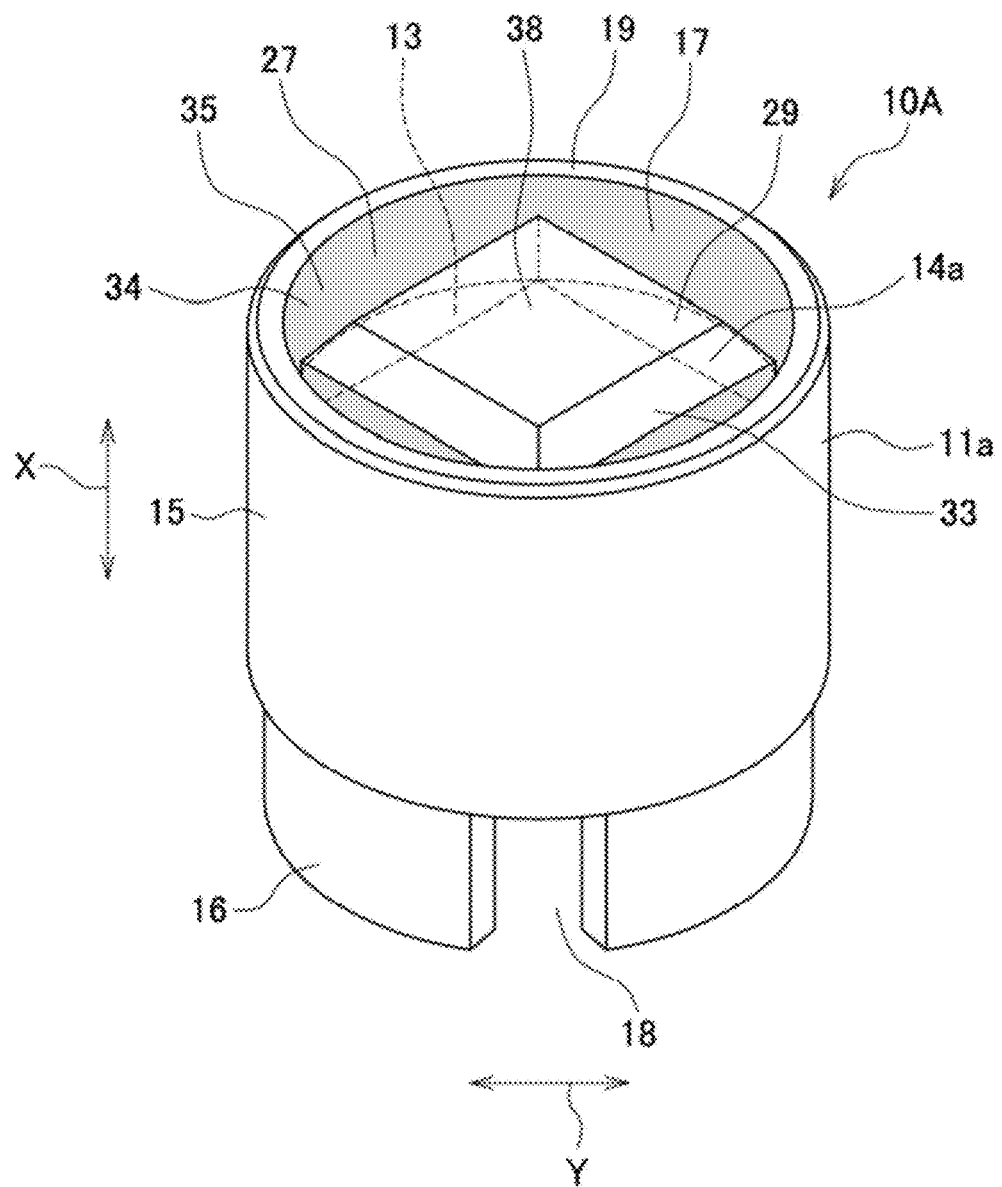
FIG. 1 is a perspective view showing an example of a lens unit.
Figure 2:
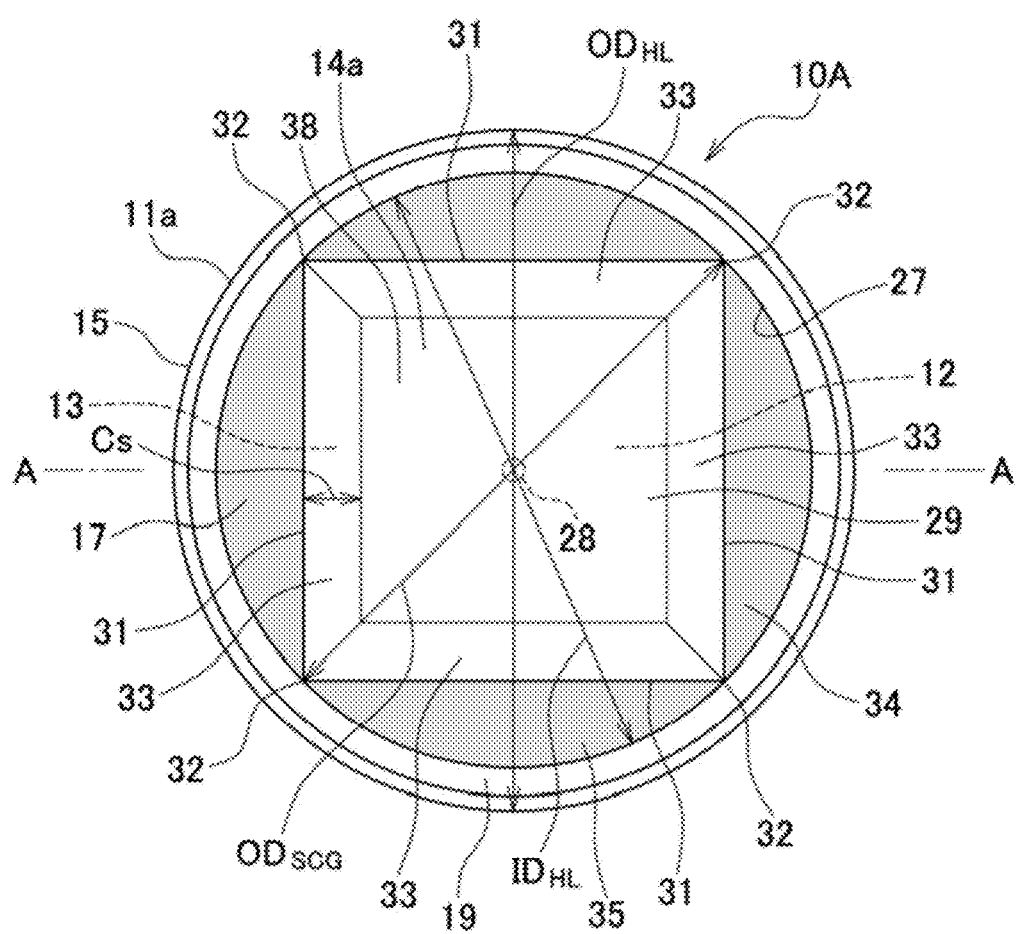
FIG. 2 is a plan view of the lens unit of FIG. 1.
Figure 3:
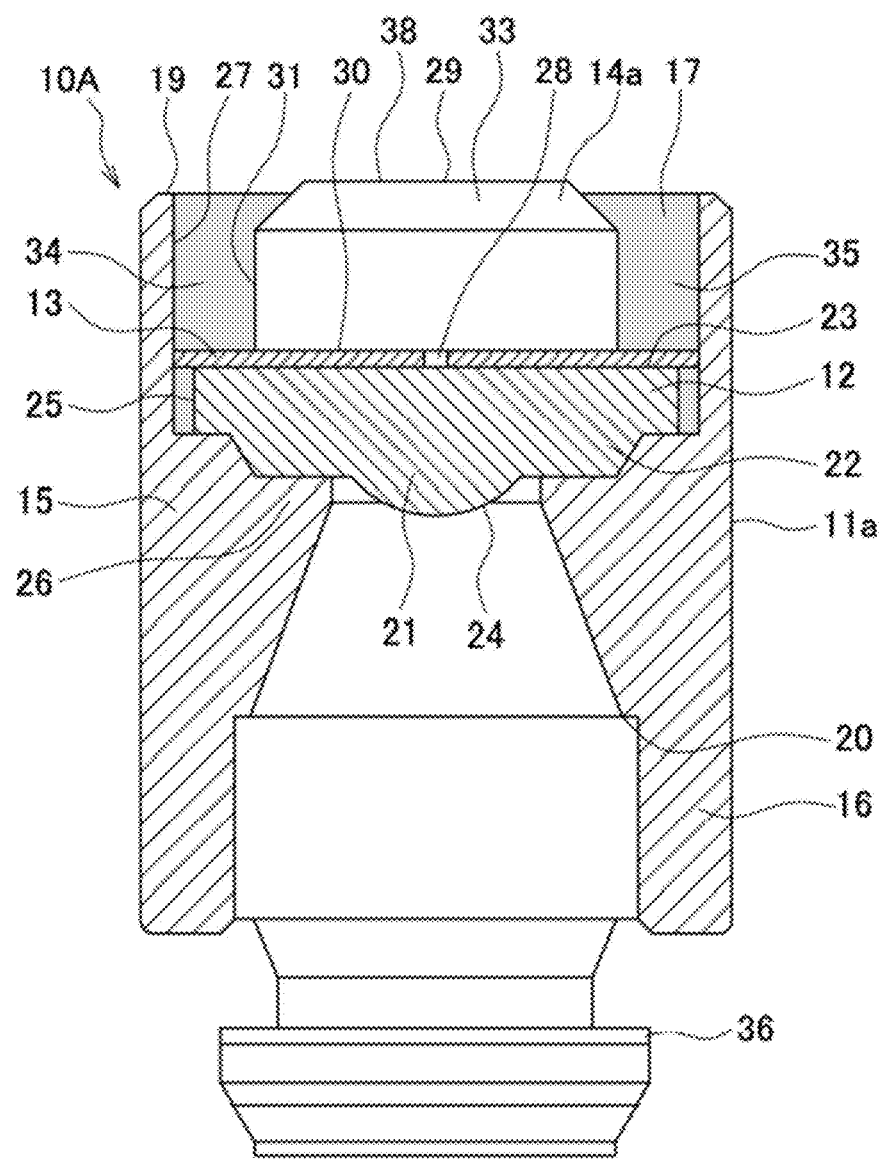
FIG. 3 is a cross-sectional view taken along the line A-A of FIG. 2 in a state that the sensor module is connected.
Figure 4:
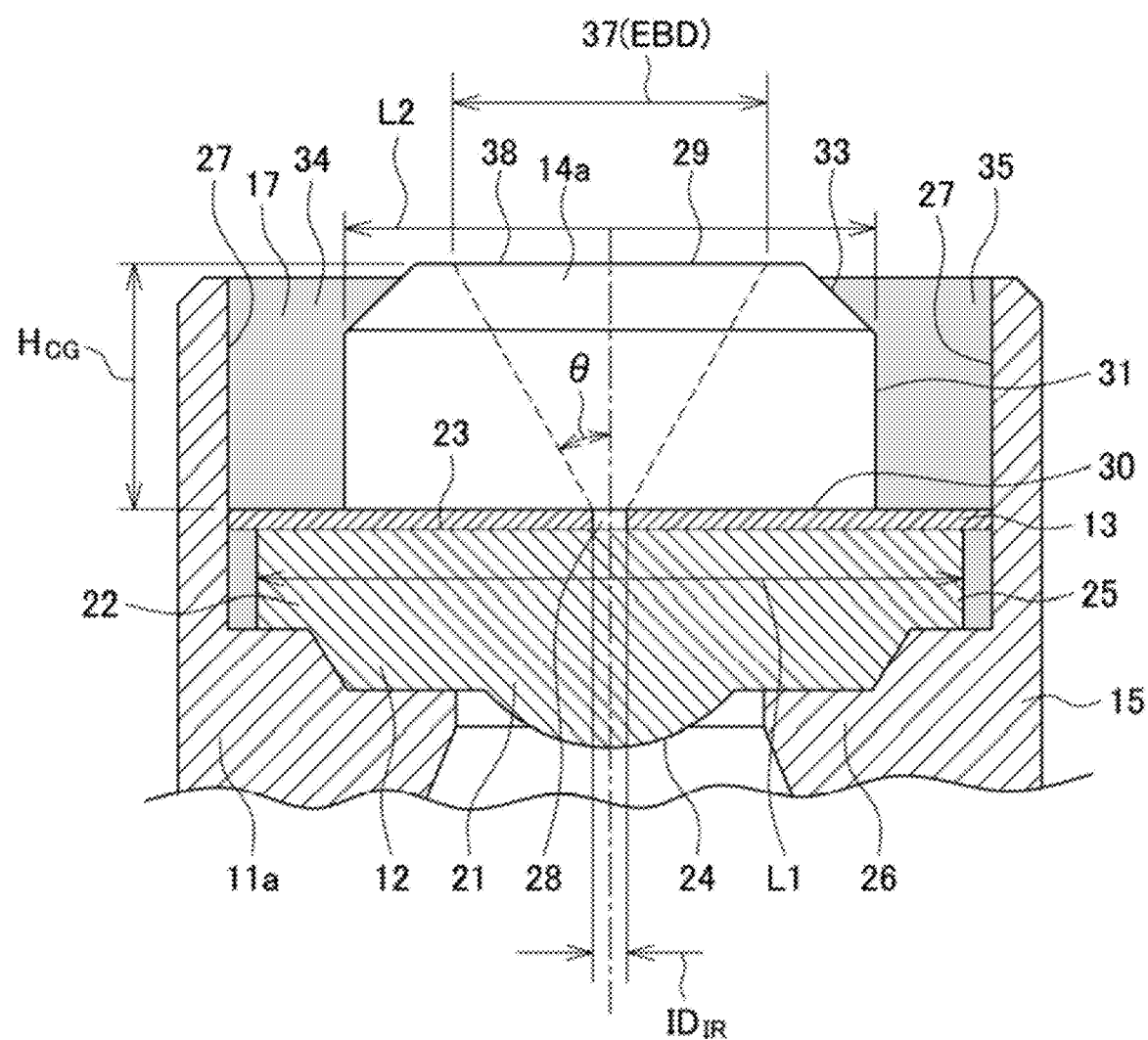
FIG. 4 is a partly enlarged cross-sectional view for explaining an inner diameter of a diaphragm of the lens unit and a field angle.

With reference to attached drawings such as FIG. 1 which is a perspective view showing an example of a lens unit 10A, a lens unit of the present invention will be explained in detail as follows. Note that FIG. 2 is a plan view of the lens unit 10A of FIG. 1, and FIG. 3 is a cross-sectional view taken along the line A-A of FIG. 2 in a state that a sensor module 36 is connected. FIG. 4 is a partly enlarged cross-sectional view for explaining an inner diameter $ID_{IR}$ of the diaphragm and a field angle θ. In FIG. 1, an optical axis direction (longitudinal direction) is shown by the arrow mark X and a radial direction is shown by the arrow mark Y.

The lens unit 10A (including small-sized lens units 10B to 10F) is suitably used as a small sized lens unit of an imaging system installed on various sensor modules 36. As an example, the lens unit 10A is installed on a distal end (tip) of the sensor module 36 (scope) of various the endoscopes (not illustrated). The endoscopes include various medical endoscopes such as a vascular endoscope, a brain endoscope and an otological endoscope, various industrial endoscopes and all endoscopes to be developed in the future.

The lens unit 10A is formed by a holder 11a and individually prepared lens 12, copper diaphragm plate 13 (diaphragm means) and cover member 14a. In the lens unit 10A, the copper diaphragm plate 13 is arranged rearward of the cover member 14a in the optical axis direction, and the lens 12 is arranged rearward of the copper diaphragm plate 13 in the optical axis direction. The cover member 14a, the copper diaphragm plate 13 and the lens 12 are arranged in a row (in series) in the optical axis direction. As shown in FIG. 3, the cover member 14a, the copper diaphragm plate 13 and the lens 12 are housed in a housing space 17 of the holder 11a individually with each other.

Although the holder 11a is made of synthetic resin (plastic), the holder 11a can be made of metals such as SUS (stainless steel) and alloy. The holder 11a includes a body portion 15 extended in the optical axis direction (longitudinal direction), a leg portion 16 continued from the body portion 15 and extended rearward in the optical axis direction from the body portion 15, a housing space 17 surrounded by the body portion 15 and formed on an approximately upper half of the body portion 15, and a sensor module housing space 18 surrounded by the leg portion 16 and formed inside the leg portion 16.

The body portion 15 of the holder 11a has a front end 19 and a rear end 20. An outer diameter $OD_{HL}$ (diameter of body portion 15 of holder 11a) is 1.4 mm. The outer diameter $OD_{HL}$ of the body portion 15 of the holder 11a is appropriately determined according to the type of the sensor module 36 connected to the lens unit 10A (including small-sized lens units 10B to 10F). Although the outer diameter $OD_{HL}$ (diameter of body portion 15) of the body portion 15 of the holder 11a is not particularly limited, the outer diameter $OD_{HL}$ of the body portion 15 is adjusted within the range of 0.5 mm to 10 mm. The leg portions 16 are integrally formed with the body portion 15 and four leg portions 16 are arranged at equal intervals in a circumferential direction of the body portion 15.

The housing space 17 of the holder 11a has a circular (complete round) cross-sectional shape in a radial direction. The housing space 17 is formed in a cylindrical shape extending from the front end 19 (frontward) to the rear end 20 (rearward) of the body portion 15 of the holder 11a. In the housing space 17, the lens 12, the copper diaphragm plate 13 and the cover member 14a are housed. In the sensor module housing space 18, as shown in FIG. 3, the sensor module 36 is fitted.

The inner diameter $ID_{HL}$ of the body portion 15 (housing space 17 for housing cover member 14a, copper diaphragm plate 13 and lens 12) of the holder 11a is within the range of 0.4 mm or more and 8 mm or less (0.4 mm to 8 mm). The outer diameter $OD_{HL}$ of the body portion 15 of the holder 11a is within the range of 0.5 mm to 10 mm and the inner diameter $ID_{HL}$ of the body portion 15 of the holder 11a is within the range of 0.4 mm or more and 8 mm or less (0.4 mm to 8 mm), the lens unit 10A can be extremely small-sized by housing the lens 12, the copper diaphragm plate 13 and the cover member 14a in the housing space 17 of the holder 11a. Thus, the lens unit 10A can be suitably connected to the small-sized sensor module 36.

The lens 12 is made by molding a transparent glass material or a transparent synthetic resin. The lens 12 has a circular cross-sectional shape and is housed in rearward of the housing space 17. The outer shape L1 of the lens 12 is within the range of 1.1 to 1.2 mm (shown in FIG. 4). The outer shape L1 of the lens 12 is appropriately determined according to the type of the sensor module 36 of the endoscope in which the lens unit 10A (including lens units 10B to 10F) is used. Although the outer shape L1 of the lens 12 is not particularly limited, it is necessary to specify the outer shape L1 (size) capable of being housed in the housing space 17 of the holder 11a.

The lens 12 a lens portion 21 having a circular shape and formed on the center of the lens 12, a flange portion 22 having a predetermined area and extending outward in a radial direction from an outer peripheral edge of the lens portion 21, a front end surface 23 having a flat shape and located at the object side (cover member 14a side), a rear end surface 24 located on an opposite side (image side) of the front end surface 23, and side surfaces 25 extending between the front and rear end surfaces 23, 24.

The front end surface 23 of the lens 12 faces the copper diaphragm plate 13 (rear end surface 30 of cover member 14a). The entire area of the front end surface 23 is fixed to the copper diaphragm plate 13 (rear end surface 30 of cover member 14a) by a transparent adhesive material (not illustrated). The rear end surface 24 of the flange portion 22 of the lens 12 is fixed to a flange abutting portion 26 of the housing space 17 of the holder 11a by an adhesive material (not illustrated). A gap is formed between the side surfaces 25 of the lens 12 and an inner peripheral surface 27 of the holder 11a.

A copper diaphragm plate 13 (diaphragm means) is fitted (housed) in the housing space 17, located at frontward in the optical axis direction of the lens 12, and contact with the front end surface 23 of the lens 12. The copper diaphragm plate 13 is formed in a disk shape. A thickness (thickness dimension) of the copper diaphragm plate 13 is 0.03 mm. A diaphragm 28 (diaphragm aperture) having a circular shape and penetrating through the copper diaphragm plate 13 is perforated on the center of the copper diaphragm plate 13. The inner diameter $ID_{IR}$ of the diaphragm 28 (diaphragm aperture) is within the range of 0.01 mm or more and 0.3 mm or less (0.01 mm to 0.3 mm).

The size and thickness of the copper diaphragm plate 13 are appropriately determined according to the type of the sensor module 36 of the endoscope in which the lens unit 10A (including lens units 10B to 10F) is used. Although the size and thickness of the copper diaphragm plate 13 is not particularly limited, it is necessary to specify the size and thickness capable of being housed in the housing space 17 of the holder 11a. The lens 12 and the copper diaphragm plate 13 can be formed to have different cross-sectional shape and size or formed to have same ross-sectional shape and size.

The cover member 14a is formed by cutting a transparent glass material (cover glass) into a regular quadrangular prism (quadrangular prism) or molding a transparent synthetic resin (cover plastic) into a regular quadrangular prism (quadrangular prism). The cover member 14a includes a front end surface 29 having a flat shape and located at the object side, a rear end surface 30 having a flat shape and located at an opposite side (image side) of the front end surface 29, four side surfaces 31 extending between the front and rear end surfaces 29, 30, and four corners 32 where the side surfaces 31 intersect with each other. In the cover member 14a, the side surfaces 31 continuing from the front end surface 29 located at the object side to the rear end surface 30 located at the image side is formed in a regular quadrangular (square) prism (quadrangular prism), and a cross-sectional shape in the radial direction is formed in a regular quadrangular (square) shape (quadrangular shape). Accordingly, the front end surface 29 and the rear end surface 30 are formed in a regular quadrangular shape (quadrangular shape).

In the cover member 14a, the corners where the front end surface 29 and each of the side surfaces 31 intersect are chamfered by cutting the corners, or the corners where the front end surface 29 and each of the side surfaces 31 intersect are chamfered by molding the synthetic resin material. Four chamfered surfaces 33 inclined at a downward gradient from the front end surface 29 to the side surfaces 31 are formed between the front end surface 29 and the side surfaces 31 of the cover member 14a. A length $C_S$ of the chamfered surfaces 33 of the cover member 14a in a radial direction is within the range of 0.3 mm or less, and preferably within the range of 0.05 mm or more and 0.3 mm or less (0.05 mm to 0.3 mm). The front end surface 29 is surrounded by the chamfered surfaces 33. Note that it is not necessary to chamfer the corners where the front end surface 29 and each of the side surfaces 31 intersect.

As shown in FIG. 3, the cover member 14a is located at frontward in the optical axis direction of the copper diaphragm plate 13 and fitted (housed) in frontward of the housing space 17 of the body portion 15 of the holder 11a. The tips of all of four corners 32 or the tips of a plurality of four corners 32 of the cover member 14a having the regular quadrangular prism (quadrangular prism) shape are in contact with the inner peripheral surface 27 of the body portion 15 of the holder 11a. The body portion 15 of the holder 11a forms a circumscribed circle of the front and rear end surfaces 29, 30 of the cover member 14a having a regular quadrangular cross-section. Note that it is enough that the tips of at least two of the corners 32 in the four corners 32 of the cover member 14a having the regular quadrangular prism (quadrangular prism) shape are in contact with the inner peripheral surface 27 of the body portion 15 of the holder 11a.

In the regular quadrangular prism (quadrangular prism) of the cover member 14a, a length $OD_{SCG}$ of a diagonal line (maximum diameter in radial direction) is 1.2 mm and an outer shape L2 is approximately 0.85 mm. In the cover member 14a, a thickness $H_{CG}$ from the front end surface 29 to the rear end surface 30 is within the range of 0.01 mm or more and 0.5 mm or less (0.01 mm to 0.5 mm). The length $OD_{SCG}$ of the diagonal line, the outer shape L2 and the thickness $H_{CG}$ of the cover member 14a are appropriately determined according to the type of the sensor module 36 of the endoscope in which the lens unit 10A (including lens units 10B to 10F) is used. Although the length $OD_{SCG}$ of the diagonal line, the outer shape L2 and the thickness $H_{CG}$ of the cover member 14a are not particularly limited, it is necessary to specify the length $OD_{SCG}$ of the diagonal line, the outer shape L2 and the thickness $H_{CG}$ so as to be capable of being housed in the housing space 17 of the holder 11a.

In the lens unit 10A, when the cover member 14a having a regular quadrangular cross-sectional shape (quadrangular cross-sectional shape) is fitted (housed) in the housing space 17 of the body portion 15 of the holder 11a having a circular cross-sectional shape, gaps (clearances) 34 are formed between each of four side surfaces 31 of the cover member 14a and the inner peripheral surface 27 of the body portion 15 of the holder 11a, and four gaps 34 are arranged in a circumferential direction of the lens unit 10A. An adhesive material 35 (filler) is injected (filled) in the four gaps 34 formed between each of the side surfaces 31 of the cover member 14a and the inner peripheral surface 27 of the body portion 15 of the holder 11a. The adhesive material 35 is hardened in the gaps 34.

When unnecessary light is entered from the four gaps 34 into the sensor module 36 (light receiving element), the light can be prevented from entering from the gaps 34 by specifying the color of the adhesive material 35 to black or gray and filling the black or gray adhesive material 35 in the gaps 34 for blocking the light, for example. Thus, unnecessary light can be prevented from entering in the sensor module 36 (light receiving element).

Figure 6:
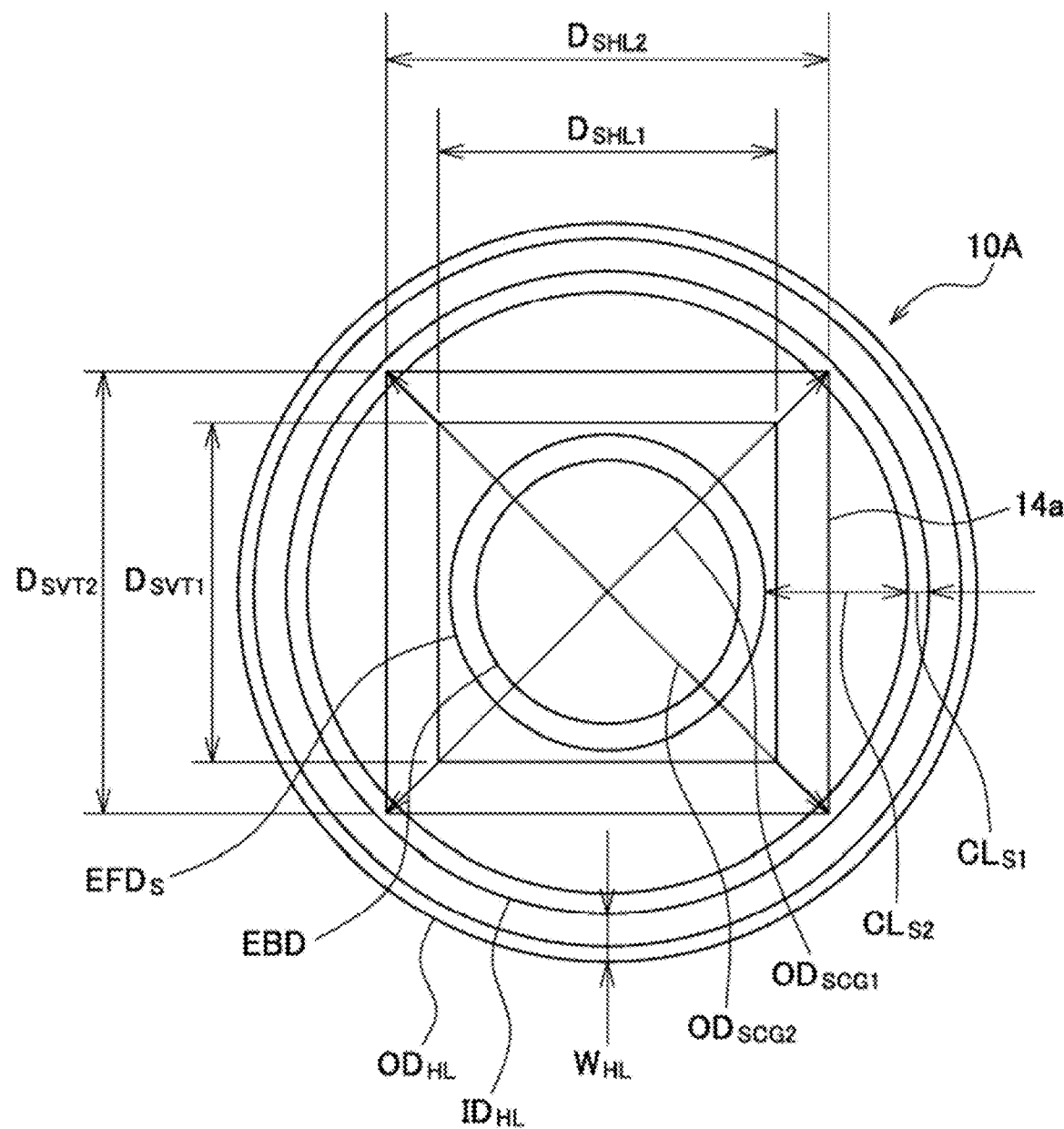
FIG. 6 is a diagram continued from FIG. 5 for explaining an example of the calculation of various values related to the cover member.

In the lens unit 10A (small-sized lens unit), an effective area 37 (EBD) of the light beam extending from the lens 12 through the diaphragm 28 (diaphragm aperture) of the copper diaphragm plate 13 (diaphragm means) to the front end surface 29 located at the object side of the cover member 14a appears on the front end surface 29 of the cover member 14a having the regular quadrangular shape (quadrangular shape) (shown in FIG. 6). The effective area 37 (EBD) of the light beam appeared on the front end surface 29 of the cover member 14a has a circular (complete round) shape. The effective area 37 (EBD) of the light beam is located inside a light receiving area 38 without being displaced outside the light receiving area 38 having the regular quadrangular shape (quadrangular shape) surrounded by the outer peripheral edge of the front end surface 29 of the cover member 14a.

A diameter EBD of the effective area 37 of the light beam shown in FIG. 4 is calculated by the following (Formula 1).

$$EBD=2*H_{CG}*\tan \theta +ID_{IR} \quad \text{(Formula 1)}$$

EBD: Diameter of effective area 37 of light beam
$H_{CG}$: Thickness of cover member 14a
θ: Field angle (half angle)
$ID_{IR}$: Inner diameter of diaphragm
The conditions for calculating EBD are as follows.
(1) Thickness of cover member 14a
  0.01 mm≤$H_{CG}$≤0.5 mm
(2) Inner diameter of diaphragm 28
  0.01 mm≤$ID_{IR}$≤0.3 mm
(3) Field angle (full angle)
  2θ≤150°

When the small-sized lens unit 10A is installed on the distal end of the sensor module 36 (scope) of the endoscope, the light (image) entered from the circular effective area 37 (EBD) located inside the front end surface 29 (light receiving area 38) of the cover member 14a having the regular quadrangular shape (quadrangular shape) passes through the cover member 14a, passes through the diaphragm 28 (diaphragm aperture) of the copper diaphragm plate 13 (diaphragm means), enters in the lens 12, and then enters in the light receiving element of the sensor module 36 from the lens 12. Thus, the light is outputted (displayed) as an image or outputted as a light signal.

In the lens unit 10A, when the tips of at least one of four corners 32 of the cover member 14a formed in the regular quadrangular prism (quadrangular prism) is separated inward in a radial direction from the inner peripheral surface 27 of the housing space 17 of the body portion 15 of the holder 11$a$ at a predetermined separate distance, the predetermined separate distance between the tips of the corners 32 and the inner peripheral surface 27 of the housing space 17 of the body portion 15 of the holder 11$a$ is within the range of 0.1 mm or less, and preferably 0.01 mm or more and 0.1 mm or less (0.01 mm to 0.1 mm).

Figure 5:
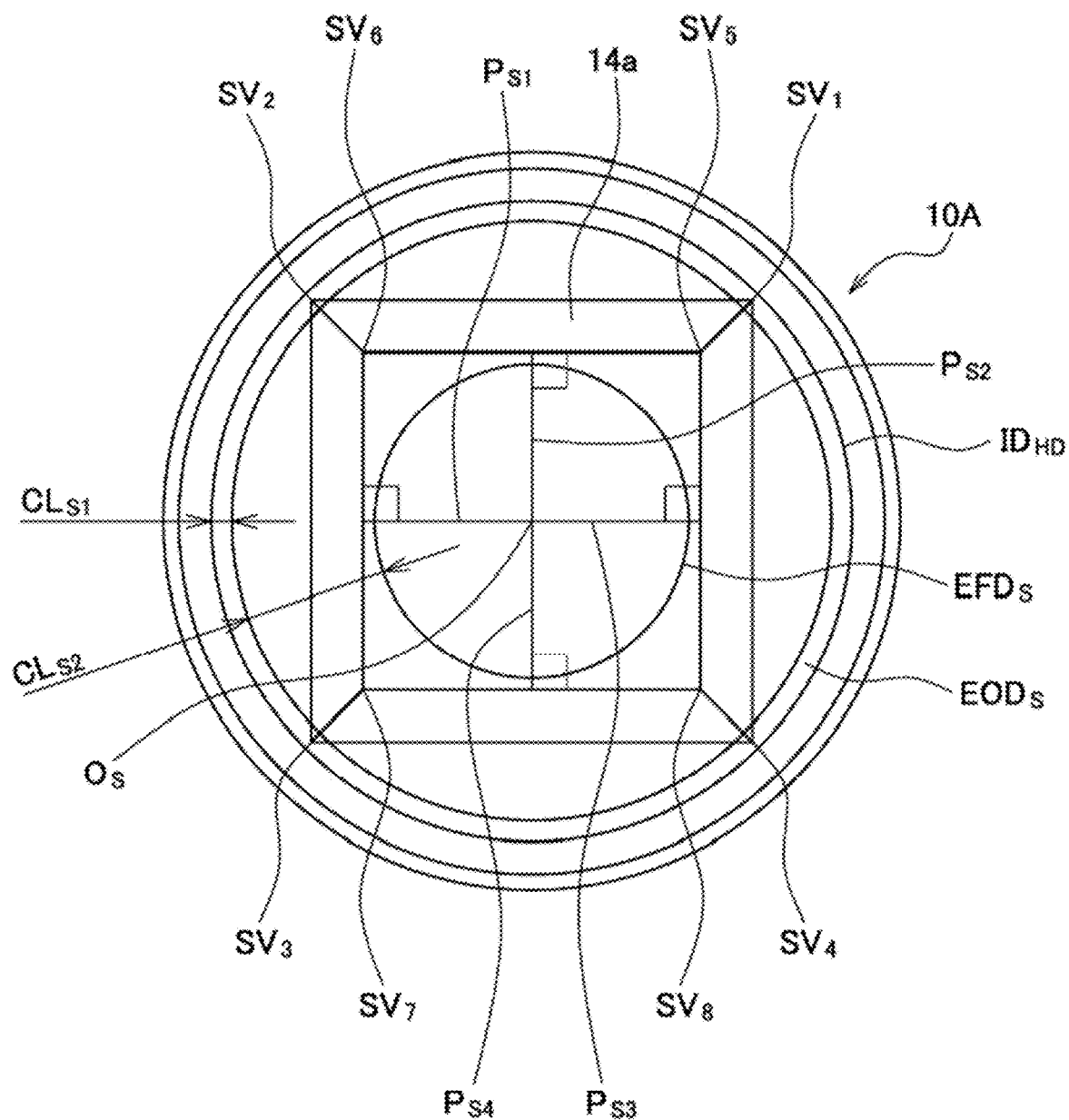
FIG. 5 is a diagram for explaining an example of the calculation of various values related to a cover member.

FIG. 5 is a diagram for explaining an example of the calculation of various values related to the cover member 14$a$. In the lens unit 10A shown in FIG. 1, the effective area EBD of the light beam, the effective area $EFD_S$ of the front end surface 29 (planar part) of the cover member 14$a$, outer shapes $D_{SVT2}$, $D_{SHL2}$ of the cover member 14$a$, the length $OD_{SCG}$ of the diagonal line of the cover member 14$a$, the inner diameter $ID_{HL}$ of the body portion 15 of the holder 11$a$, and the outer diameter $OD_{HL}$ of the body portion 15 of the holder 11$a$ are calculated by the calculation explained below. Note that the objects indicated by each symbol shown in FIG. 5 are as follows.

$ID_{HL}$: Inner diameter of body portion 15 of holder 11$a$ $CL_{S1}$: Variation tolerance area of apexes (corners) of cover member 14$a$ $CL_{S2}$: Variation tolerance area of front end surface 29 of cover member 14$a$ $SV_{1-4}$: Apexes (corners) of cover member 14$a$ $SV_{5-8}$: Apexes (corners) of front end surface 29 of cover member 14$a$ $EFD_S$: Effective area 37 of front end surface 29 of cover member 14$a$ $EOD_S$: Effective area of outer shape of cover member 14$a$ The variation tolerance area of the apexes of the cover member 14$a$ is $CL_{S1} \leq 0.1$ mm, and the variation tolerance area of the front end surface 29 of the cover member 14$a$ is $CL_{S2} \leq 1.4$ mm. The apexes $SV_{1-4}$ of the cover member 14$a$ are within the range of $CL_{S1}$.

In the apexes $SV_{5-8}$ of the front end surface 29 of the cover member 14$a$, when a perpendicular lines are drawn from the center $O_S$ to straight lines connecting the neighboring apexes, the length of the perpendicular lines ($P_{S1}$ to $P_{S4}$) follows the conditions below. When $CL_{s2}$ is 0, it means that the chamfered surface C is not formed.

Figure 7:
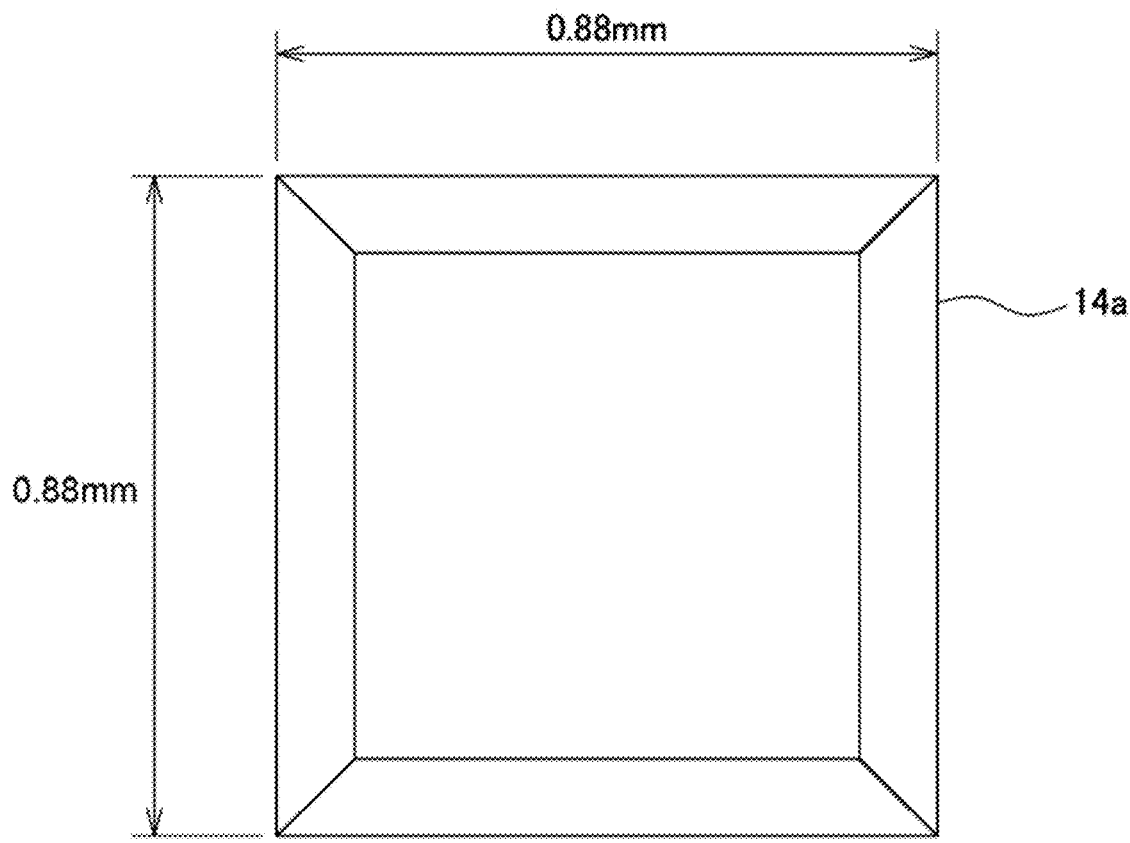
FIG. 7 is a diagram showing calculated outer shape (length of one side), thickness and length of chamfered surface C in a radial direction of the cover member.
Figure 7:
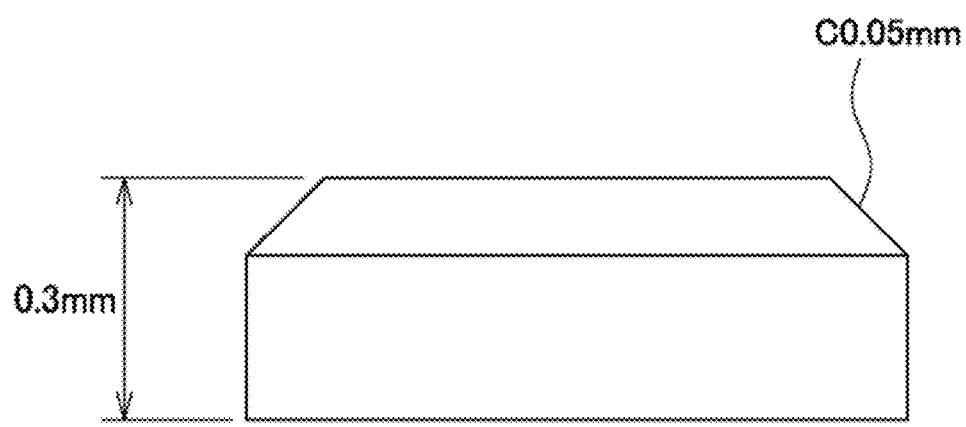

$P_{S1} \geq EFD_S/2$
$P_{S2} \geq EFD_S/2$
$P_{S3} \geq EFD_S/2$
$P_{S4} \geq EFD_S/2$ FIG. 6 is a diagram continued from FIG. 5 for explaining an example of the calculation of various values related to the cover member 14$a$. FIG. 7 is a diagram showing calculated outer shape (length of one side), thickness and length of chamfered surface C in a radial direction of the cover member 14$a$. The objects indicated by each symbol shown in FIG. 6 are as follows.

$ID_{HL}$: Inner diameter of holder 11$a$ $OD_{HL}$: Outer diameter of holder 11$a$ $W_{HL}$: Thickness of body portion 15 of holder 11$a$ $CL_{S1}$: Variation tolerance area of apexes (corners) of cover member 14$a$ $CL_{S2}$: Variation tolerance area of front end surface 29 of cover member 14$a$ EBD: Diameter of effective area 37 of light beam $EFD_S$: Light receiving area 38 of front end surface 29 of cover member 14$a$ $D_{SVT1}$: Length (vertical) of outer shape of front end surface 29 of cover member 14$a$ $D_{SHL1}$: Length (horizontal) of outer shape of front end surface 29 of cover member 14$a$ $OD_{SCG1}$: Length (diagonal) of outer shape of cover member 14$a$ $OD_{SCG2}$: Length (diagonal) of outer shape of cover member 14$a$ The size of each part of the cover member 14$a$ is determined based on the diameter EBD of the effective area 37 of the light beam. $D_{SVT1}$ and $D_{SHL1}$ follow the conditions below, and $OD_{SCG1}$ and $OD_{SCG2}$ follow the conditions below.

$D_{SVT1} \geq EFD_S \geq EBD + CL_{S1}$
$D_{SHL1} \geq EFD_S \geq EBD + CL_{S1}$
$ID_{HL} \geq OD_{SCG1} \geq EFD_S + CL_{S2}$
$ID_{HL} \geq OD_{SCG2} \geq EFD_S + CL_{S2}$ The size of the cover member 14$a$ is determined by the above described conditions. In addition, the size of the outer diameter of the holder 11$a$ is determined by the following (Formula 2).

$$OD_{HL} = ID_{HL} + W_{HL} \quad \text{(Formula 2)}$$

The length $C_S$ of the chamfered surface C in a radial direction and the thickness of the body portion 15 of the holder 11$a$ are specified within the following range.

Length of chamfered surface C of cover member 14$a$: 0 mm $\leq C_S \leq$ 0.3 mm Thickness of body portion 15 of holder 11$a$: 0.01 mm $\leq W_{HL} \leq$ 1 mm A tolerance is determined considering the processing method of the cover member 14$a$. At that time, be sure to confirm that the size is not out of the range explained in FIG. 5.

Concrete examples of the calculation of various values related to the cover member 14$a$ having a regular quadrangular prism shape are shown below. The conditions of the concrete examples of the calculation of various values are as follows.

Thickness of cover member 14$a$: $H_{CG} = 0.3$ mm (0.01 mm $\leq H_{CG} \leq$ 0.5 mm)

Inner diameter of diaphragm 28: $ID_{IR} = 0.1$ mm (0.01 mm $\leq ID_{IR} \leq$ 0.3 mm)

Field angle (full angle): $2\theta = 90°$ ($\theta \leq 150°$)

Size of chamfered surface C of cover member 14$a$: $C_S = 0.05$ mm (0 mm $\leq C_S \leq$ 0.3 mm)

Variation tolerance area of apexes of cover member 14$a$: $CL_{S1} = 0.04$ mm Thickness of body portion 15 of holder 11$a$: $W_{HL} = 0.1$ mm (0.01 mm $\leq W_{HL} \leq$ 1 mm)

(1) Calculation of diameter of effective area 37 of light beam $$\begin{aligned} EBD &= 2 * H_{CG} * \tan\theta + ID_{IR} \\ &= 2 * 0.3 * \tan 45° + 0.1 \\ &= 0.7 \text{mm} \end{aligned}$$

(2) Calculation of light receiving area 38 of front end surface 29 of cover member 14$a$ $$\begin{aligned} EFD_S &= EBD + CL_{S1} * 2 \\ &= 0.7 + 0.04 * 2 \\ &= 0.78 \text{ mm} \end{aligned}$$

(3) Calculation of outer shape (length of one side) of cover member 14a $$D_{SVT2} = D_{SHL2}$$
$$= D_{SVT1} + C_S * 2$$
$$= 0.78 + 0.05 * 2$$
$$= 0.88 \text{ mm}$$

(4) Calculation of length of diagonal line of cover member 14a $$OD_{SCG} = \sqrt{(D_{SVT2}{}^\wedge 2 + D_{SHL2}{}^\wedge 2)}$$
$$= \sqrt{(0.88^\wedge 2 + 0.88^\wedge 2)}$$
$$\approx 1.245$$

(5) Calculation of inner diameter of holder 11a $$ID_{HL} = OD_{SCG} + CL_{S1} * 2$$
$$= 1.245 + 0.04 * 2$$
$$= 1.325 \text{ mm}$$

(6) Calculation of outer diameter of body portion 15 of holder 11a $$OD_{HL} = ID_{HL} + W_{HL} * 2$$
$$= 1.325 + 0.1 * 2$$
$$= 1.525 \text{ mm}$$

As the calculated size of the cover member 14a, as shown in FIG. 7, the outer shape (length of one side) of the cover member 14a is 0.88 mm, the thickness of the cover member 14a is 0.3 mm, and the length of the chamfered surface C in a radial direction is 0.05 mm.

Figure 26:
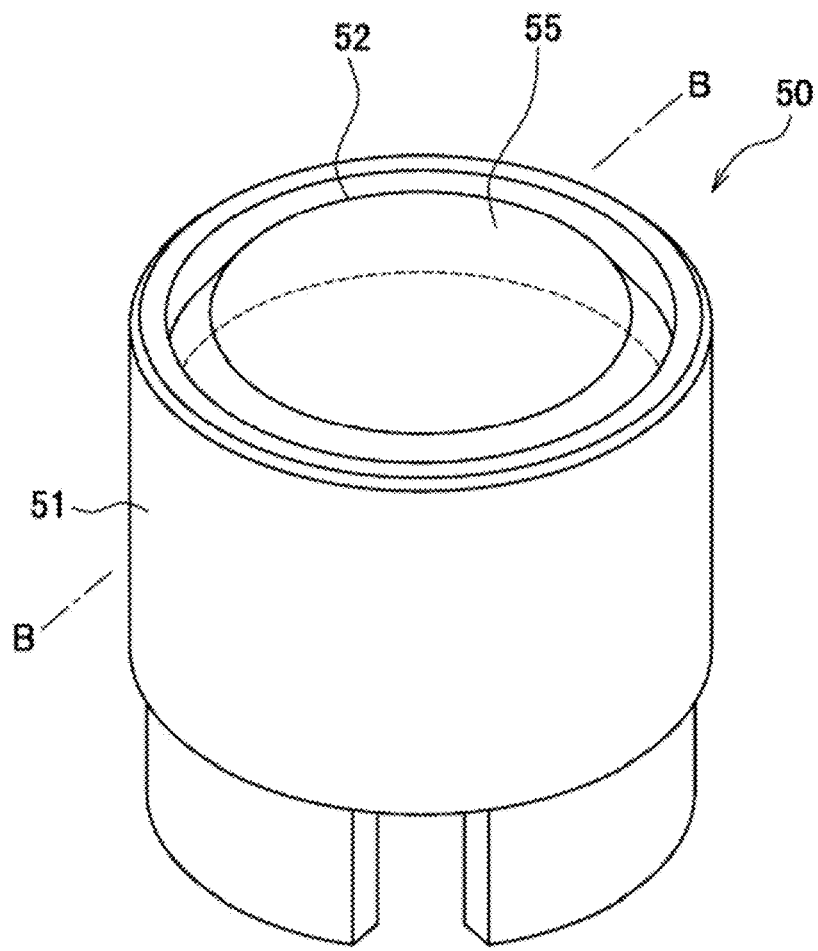
FIG. 26 is a perspective view of the lens unit showing conventional technology.
Figure 27:
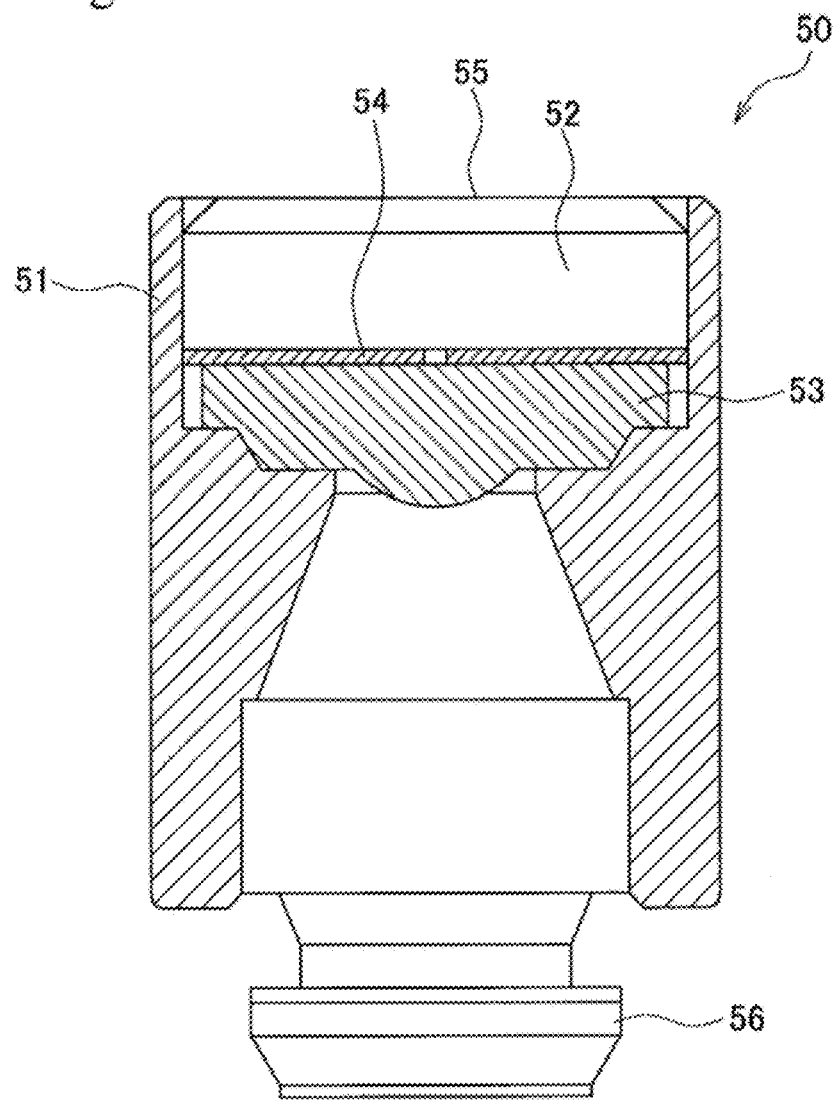
FIG. 27 is a cross-sectional view taken along the line B-B of FIG. 26.

In the lens unit 10A, the side surfaces 31 of the cover member 14a (cover glass or cover plastic) continuing from the front end surface 29 to the rear end surface 30 can be easily formed in the regular quadrangular prism (quadrangular prism) by cutting a glass material or molding a synthetic resin material. Unlike the conventional lens unit 50 shown in FIGS. 26 and 27, handwork of artisans is not required for polishing the outer peripheral surface of the cover glass 55 so that the cover glass 55 has a complete round cross-sectional shape. Accordingly, the lens unit 10A having the cover member 14a formed in a regular quadrangular prism (quadrangular prism) can be mechanically and efficiently manufactured.

In the lens unit 10A, the cover member 14a (cover glass or cover plastic) can be manufactured by cutting a glass material in the regular quadrangular prism (quadrangular prism) or molding a synthetic resin material into the regular quadrangular prism (quadrangular prism). Thus, the cover member 14a can be manufactured at low cost without depending on skilled artisans. In addition, the lens unit 10A having the cover member 14a which is formed in the regular quadrangular prism (quadrangular prism) and does not cause deviation in precision can be manufactured at low cost. Accordingly, production efficiency of the lens unit 10A can be increased.

In the lens unit 10A, the tips of at least two of four corners 32 of the regular quadrangular prism (quadrangular prism) of the cover member 14a (cover glass or cover plastic) are in contact with the inner peripheral surface 27 of the body portion 15 of the holder 11a. Thus, the cover member 14a formed in the regular quadrangular prism can be fixed to the housing space 17 of the body portion 15 of the holder 11a while preventing the cover member 14a from moving in the housing space 17 of the body portion 15 of the holder 11a.

In the lens unit 10A, the circular effective area 37 (EBD) of the light beam is located inside the light receiving area 38 having the regular quadrangular shape (quadrangular shape) surrounded by the outer peripheral edge of the front end surface 29 of the cover member 14a (cover glass or cover plastic). Thus, a part of the effective area 37 (EBD) of the light beam is not displaced (protruded) outside the light receiving area 38 having a regular quadrangular shape. Accordingly, the accurate image can be formed on the lens unit 10A.

In the lens unit 10A, when the side surfaces 31 of the cover member 14a (cover glass or cover plastic) are formed in the regular quadrangular prism (quadrangular prism), the corners can be easily chamfered by cutting the corners where the front end surface 29 of the cover member 14a and each of the four side surfaces 31 intersect or the corners can be easily chamfered by molding the synthetic resin material. Accordingly, unexpected breakage and damage of the corners of the cover member 14a can be prevented by chamfering the corners of the cover member 14a formed in the regular quadrangular prism (quadrangular prism).

When tips of at least one of four corners 32 of the cover member 14a formed in the regular quadrangular prism (quadrangular prism) is separated inward in a radial direction from the inner peripheral surface 27 of the housing space 17 of the body portion 15 of the holder 11a at a predetermined separate distance, if the predetermined separate distance between the tips of the corners 32 and the inner peripheral surface 27 of the housing space 17 exceeds 0.1 mm, a part of the circular effective area 37 (EBD) of the light beam may be displaced (protruded) outside the light receiving area 38 having the regular quadrangular shape (quadrangular shape) surrounded by the outer peripheral edge of the front end surface 29 of the cover member 14a when the cover member 14a is moved in the housing space 17 of the body portion 15 of the holder 11a. In such a case, the accurate image cannot be formed on the lens unit 10A. However, since the predetermined separate distance between the tips of the corners 32 and the inner peripheral surface 27 of the housing space 17 of the body portion 15 of the holder 11a is within the range of 0.1 mm or less and preferably 0.01 mm to 0.1 mm in the lens unit 10A, a part of the effective area 37 (EBD) of the light beam is not displaced outside the light receiving area 38 of the front end surface 29 of the cover member 14a even when the cover member 14a (cover glass or cover plastic) is moved in the housing space 17 of the body portion 15 of the holder 11a. Thus, the effective area 37 (EBD) of the light beam can be located inside the light receiving area 38 of the front end surface 29 of the cover member 14a. Accordingly, the accurate image can be formed on the lens unit 10A.

If the length $C_S$ of the chamfered surface C exceeds 0.3 mm in a radial direction, the light receiving area 38 having the regular quadrangular shape (quadrangular shape) surrounded by the outer peripheral edge of the front end surface 29 of the cover member 14a becomes small and a part of the effective area 37 (EBD) of the light beam may be located (displaced) outside the light receiving area 38 having the regular quadrangular shape (quadrangular shape) surrounded by the outer peripheral edge of the front end surface 29 of the cover member 14a. Thus, the accurate image cannot be formed on the lens unit 10A. However, since the length $C_S$ of the chamfered surface C of the lens unit 10A is 0.3 mm or less in the radial direction and preferably 0.05 mm to 0.3 mm, the effective area 37 (EBD) of the light beam can be located inside the light receiving area 38 having the regular quadrangular shape (quadrangular shape) surrounded by the outer peripheral edge of the front end surface 29 of the cover member 14a (cover glass or cover plastic). Thus, the accurate image can be formed on the lens unit 10A while preventing a part of the effective area 37 (EBD) of the light beam from being located (displaced) outside the light receiving area 38 of the front end surface 29 of the cover member 14a.

Figure 8:
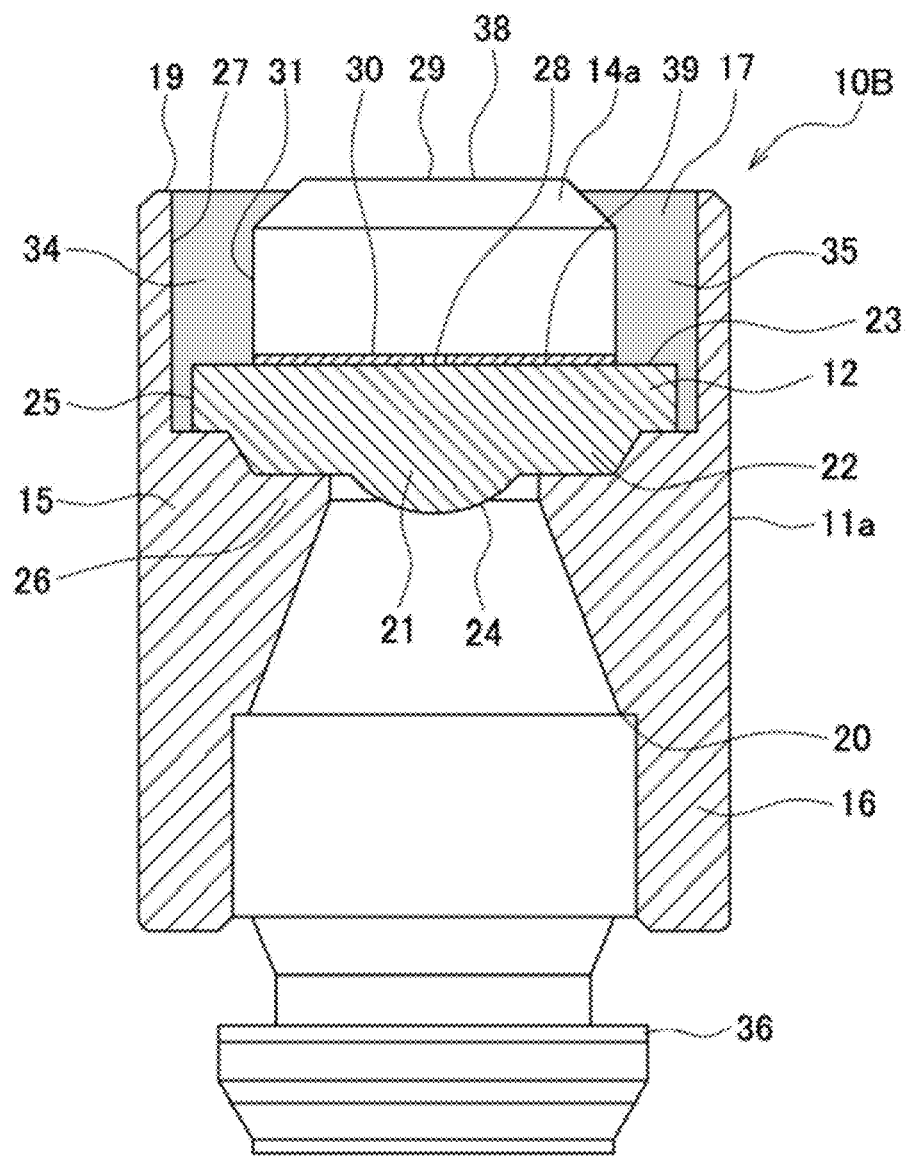
FIG. 8 is a cross-sectional view similar to FIG. 3 showing another example of the lens unit.

FIG. 8 is a cross-sectional view similar to FIG. 3 showing another example of the lens unit 10B. The lens unit 10B shown in FIG. 8 is different from the lens unit shown in FIG. 3 in a point that the diaphragm means is a diaphragm pattern 39 masked by photo-etching on the rear end surface of the cover member. Other configurations are same as the lens unit 10A shown in FIG. 1. Thus, same reference numerals as FIG. 1 are added and the detailed explanation about the other configurations of the lens unit 10B will be omitted by referring to the explanation of FIG. 1.

The lens unit 10B is formed by a holder 11a and individually prepared lens 12 and cover member 14a formed in a regular quadrangular prism (quadrangular prism). The diaphragm pattern 39 (diaphragm means) is masked on the cover member 14a. In the lens unit 10B, the lens 12 is arranged rearward in the optical axis direction of the cover member 14a, and the cover member 14a and the lens 12 are arranged in a row (in series) in the optical axis direction. As shown in FIG. 8, the cover member 14a and the lens 12 are housed in the housing space 17 of the holder 11a individually with each other. The holder 11a, the lens 12 and the cover member 14a are same as those of the lens unit 10A.

The diaphragm pattern 39 is formed on the entire area of the rear end surface 30 of the cover member 14a having the regular quadrangular cross-sectional shape (quadrangular cross-sectional shape). The diaphragm pattern 39 is a chromium film masked by photo-etching on the rear end surface 30 of the cover member 14a and has a color (e.g., black or gray) of blocking the light. The diaphragm 28 (diaphragm aperture) having a circular shape is formed on the center of the diaphragm pattern 39. The inner diameter $ID_{IR}$ of the diaphragm 28 (diaphragm aperture) of the diaphragm pattern 39 is within the range of 0.01 mm or more and 0.3 mm or less (0.01 mm to 0.3 mm).

The diaphragm means can be the diaphragm pattern 39 (chromium film) masked by photo-etching on both the front end surface 29 and the rear end surface 30 of the cover member 14a having the regular quadrangular cross-sectional shape (quadrangular cross-sectional shape). The diaphragm means also can be the diaphragm pattern 39 (chromium film) masked on the front end surface 29.

The outer diameter $OD_{HL}$ of the body portion 15 of the holder 11a (diameter of body portion 15 of holder 11a) is same as that of the lens unit 10A and adjusted within the range of 0.5 mm to 10 mm. The inner diameter $ID_{HL}$ of the body portion 15 of the holder 11a (housing space 17 for housing cover member 14a) is same as that of the lens unit 10A and is within the range of 0.4 mm or more and 8 mm or less (0.4 mm to 8 mm).

When the outer diameter $OD_{HL}$ of the body portion 15 of the holder 11a is within the range of 0.5 mm to 10 mm and the inner diameter $ID_{HL}$ of the body portion 15 of the holder 11a is 0.4 mm or more and 8 mm or less, an extremely small-sized lens unit 10B can be formed by housing the lens 12, the copper diaphragm plate 13 and the cover member 14a in the housing space 17 of the body portion 15 of the holder 11a. Accordingly, the lens unit 10B is capable of being suitably connected to the small-sized sensor module 36.

In the lens unit 10B, the tips of all of four corners 32 or the tips of a plurality of four corners 32 of the cover member 14a having the regular quadrangular prism (quadrangular prism) shape are in contact with the inner peripheral surface 27 of the body portion 15 of the holder 11a. Note that it is enough that the tips of at least two of the corners 32 in the four corners 32 of the cover member 14a are in contact with the inner peripheral surface 27 of the body portion 15 of the holder 11a. The gaps 34 are formed between each of the side surfaces 31 of the cover member 14a and the inner peripheral surface 27 of the body portion 15 of the holder 11a. The adhesive material 35 (filler) colored (e.g., black or gray) to block the light is injected (filled) in the gaps 34 and the adhesive material 35 is hardened in the gaps 34. In the lens unit 10B, a copper diaphragm plate 13a (diaphragm means) is omitted although the lens unit 10A shown in FIG. 1 includes it.

In the lens unit 10B, the effective area 37 (EBD) of the light beam extending from the lens 12 through the diaphragm 28 (diaphragm aperture) of the diaphragm pattern 39 (diaphragm means) to the front end surface 29 located at the object side of the cover member 14a appears on the front end surface 29 of the cover member 14a (shown in FIG. 6). The effective area 37 (EBD) of the light beam is located inside the light receiving area 38 without being displaced outside the light receiving area 38 having the regular quadrangular shape (quadrangular shape) surrounded by the outer peripheral edge of the front end surface 29 of the cover member 14a.

When the small-sized lens unit 10B is installed on the distal end of the sensor module 36 (scope) of the endoscope, the light (image) entered from the circular effective area 37 (EBD) located inside the light receiving area 38 of the front end surface 29 of the cover member 14a having the regular quadrangular shape (quadrangular shape) passes through the cover member 14a, passes through the diaphragm 28 (diaphragm aperture) of the diaphragm pattern 39 (diaphragm means), enters in the lens 12, and then enters in the light receiving element of the sensor module 36 from the lens 12. Thus, the light is outputted (displayed) as an image or outputted as a light signal.

In the lens unit 10B, when the tips of at least one of four corners 32 of the cover member 14a formed in the regular quadrangular prism (quadrangular prism) is separated inward in a radial direction from the inner peripheral surface 27 of the housing space 17 of the body portion 15 of the holder 11a at a predetermined separate distance, the predetermined separate distance between the tips of the corners 32 and the inner peripheral surface 27 of the housing space 17 of the body portion 15 of the holder 11a is within the range of 0.1 mm or less, and preferably 0.01 mm or more and 0.1 mm or less (0.01 mm to 0.1 mm).

The lens unit 10B has following effects in addition to the effects of the lens unit 10A shown in FIG. 1. In the lens unit 10B, the diaphragm pattern 39 (diaphragm means) can be formed by photo-etching on the rear end surface 30 of the cover member 14a formed in the regular quadrangular prism (quadrangular prism). Thus, unlike the lens unit 50 of the conventional technology shown in FIGS. 26 and 27, it is not required to interpose the copper diaphragm plate 54 (diaphragm means) between the lens 53 and the cover glass 55. Accordingly, the copper diaphragm plate 54 can be omitted and labor and time for interposing the copper diaphragm plate 54 between the lens 53 and the cover glass 55 can be reduced.

Figure 9:
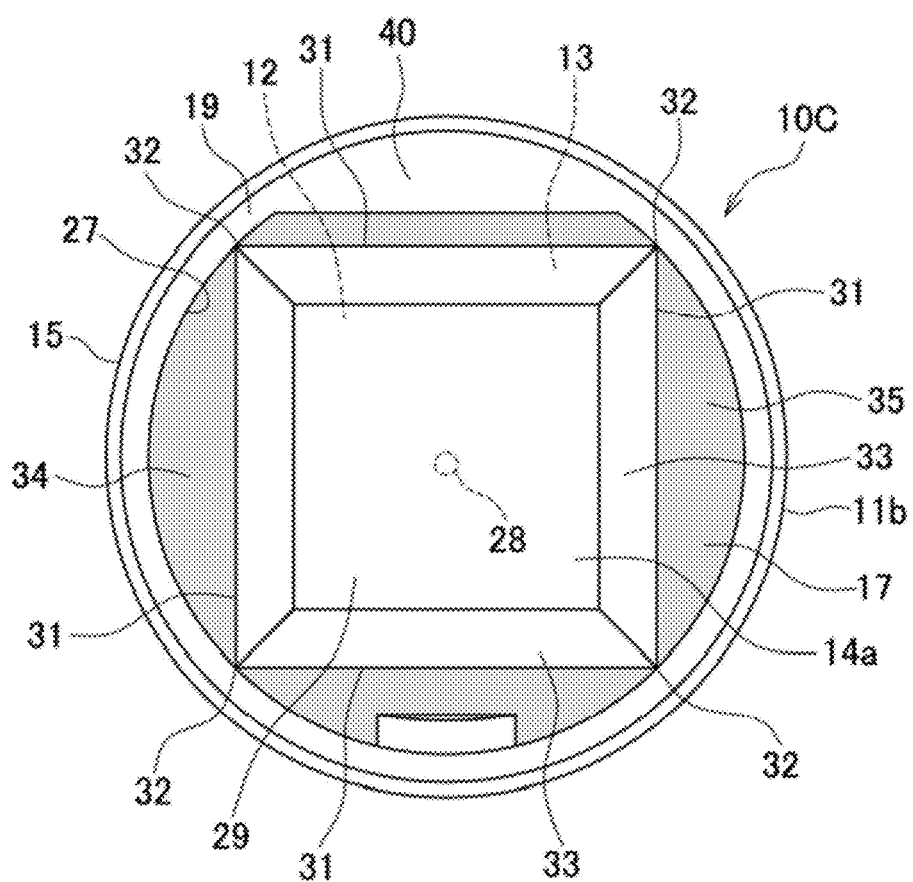
FIG. 9 is a plan view of the lens unit shown as another example.
Figure 10:
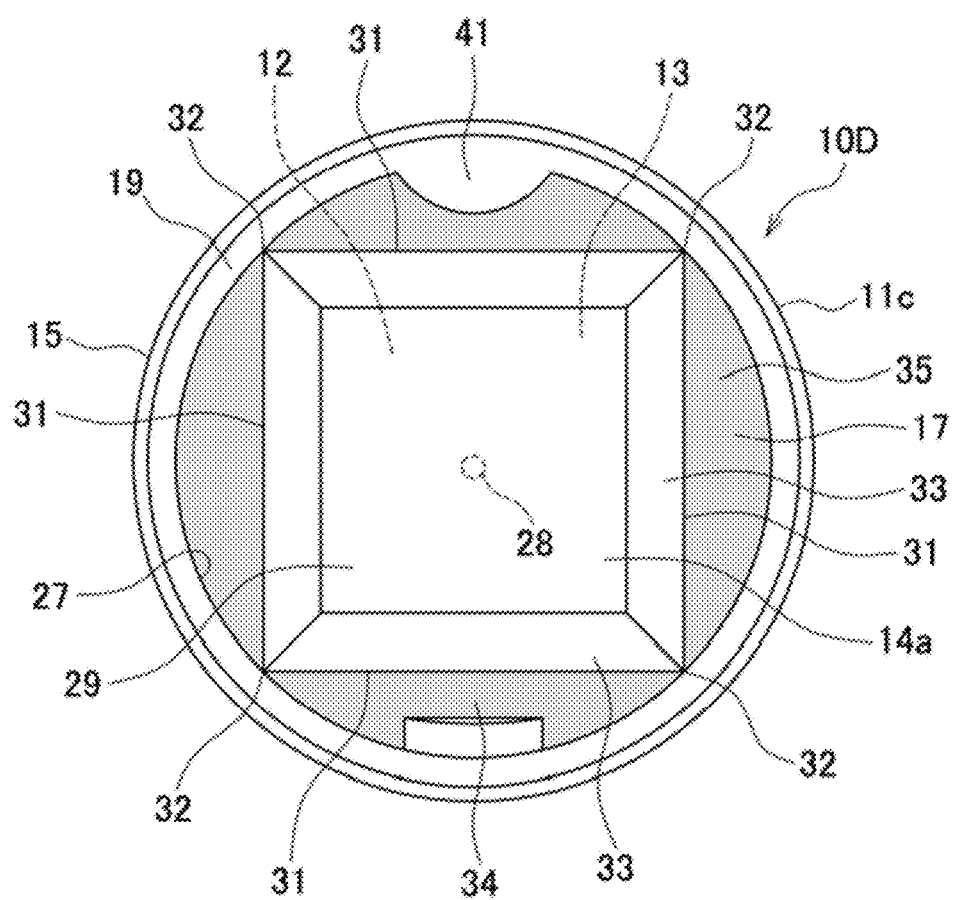
FIG. 10 is a plan view of the lens unit shown as another example.

FIG. 9 is a plan view of a lens unit 10C shown as another example. FIG. 10 is a plan view of a lens unit 10D shown as another example. The lens unit 10C shown in FIG. 9 and lens unit 10D shown in FIG. 10 are different from the lens unit shown in FIG. 1 in a point that a marking protrusion 40 or a marking protrusion 41 extending from the inner peripheral surface 27 of the body portion 15 of the holders 11b, 11c inward in the radial direction. Other configurations are same as the lens unit 10A shown in FIG. 1. Thus, same reference numerals as FIG. 1 are added and the detailed explanation about the other configurations of the lens unit 10C and the lens unit 10D will be omitted by referring to the explanation of FIG. 1.

The lens unit 10C and the lens unit 10D are formed by holders 11b, 11c and individually prepared lens 12, copper diaphragm plate 13 (diaphragm means) and cover member 14a formed in the regular quadrangular prism (quadrangular prism). In the lens unit 10C and the lens unit 10D, the copper diaphragm plate 13 is arranged rearward of the cover member 14a in the optical axis direction, and the lens 12 is arranged rearward of the copper diaphragm plate 13 in the optical axis direction. The cover member 14a, the copper diaphragm plate 13 and the lens 12 are arranged in a row (in series) in the optical axis direction.

The cover member 14a, the copper diaphragm plate 13 and the lens 12 are housed in a housing space 17 of the body portion 15 of the holder 11b individually with each other (shown in FIG. 3). The lens 12, the copper diaphragm plate 13 and the cover member 14a are same as those of the lens unit 10A. Note that, in the lens unit 10C and the lens unit 10D, it is also possible to omit the copper diaphragm plate 13 same as the lens unit 10B shown in FIG. 8 and the diaphragm pattern 39 can be masked by photo-etching on the rear end surface 30 of the cover member 14a.

In the lens unit 10C, a linearly protruded marking protrusion 40 extending from the inner peripheral surface 27 of the body portion 15 of the holder 11b in a radial direction of the holder 11b (toward the housing space 17) is extended to the gaps 34 (housing space 17) formed between the side surfaces 31 of the cover member 14a and the inner peripheral surface 27 of the body portion 15 of the holder 11b. The marking protrusion 40 functions as a marking (positioning mark) for determining the top (upper) portion and the bottom (lower) portion of the sensor module 36 (scope) of the endoscope by visually recognizing the marking protrusion 40.

In the lens unit 10D, a circularly protruded marking protrusion 41 extending from the inner peripheral surface 27 of the body portion 15 of the holder 11c in a radial direction of the holder 11c (toward the housing space 17) is extended to the gaps 34 (housing space 17) formed between the side surfaces 31 of the cover member 14a and the inner peripheral surface 27 of the body portion 15 of the holder 11c. The marking protrusion 41 functions as a marking (positioning mark) for determining the top (upper) portion and the bottom (lower) portion of the sensor module 36 (scope) of the endoscope by visually recognizing the marking protrusion 41. Note that the shape of the marking protrusion 40 and the marking protrusion 41 is not particularly limited. The marking protrusion having various shapes can be formed on the inner peripheral surface 27 of the body portion 15 of the holder 11b or the holder 11c.

The outer diameter $OD_{HL}$ of the body portion 15 of the holders 11b, 11c (diameter of body portion 15 of holders 11b, 11c) is same as that of the lens unit 10A and adjusted within the range of 0.5 mm to 10 mm. The inner diameter $ID_{HL}$ of the body portion 15 of the holders 11b, 11c (housing space 17 for housing cover member 14a) is same as that of the lens unit 10A and is within the range of 0.4 mm or more and 8 mm or less (0.4 mm to 8 mm). When the outer diameter $OD_{HL}$ of the body portion 15 of the holders 11b, 11c is within the range of 0.5 mm to 10 mm and the inner diameter $ID_{HL}$ of the body portion 15 of the holders 11b, 11c is 0.4 mm or more and 8 mm or less, an extremely small-sized lens units 10C, 10D can be formed by housing the lens 12, the copper diaphragm plate 13 and the cover member 14a in the housing space 17 of the body portion 15 of the holders 11b, 11c. Accordingly, the lens units 10C, 10D are capable of being suitably connected to the small-sized sensor module 36.

In the lens unit 10C and the lens unit 10D, the cover member 14a is located at frontward in the optical axis direction of the copper diaphragm plate 13 and the cover member 14a is fitted (housed) in frontward of the housing space 17 of the body portion 15 of the holders 11b, 11c. The tips of all of four corners 32 or the tips of a plurality of four corners 32 of the cover member 14a having the regular quadrangular prism (quadrangular prism) shape are in contact with the inner peripheral surface 27 of the body portion 15 of the holders 11b, 11c. Note that it is enough that the tips of at least two of the corners 32 in the four corners 32 of the cover member 14a are in contact with the inner peripheral surface 27 of the body portion 15 of the holders 11b, 11c.

In the lens unit 10C and the lens unit 10D, when the cover member 14a having a regular quadrangular cross-sectional shape is fitted (housed) in the housing space 17 of the body portion 15 of the holders 11b, 11c having a circular cross-sectional shape at a position avoiding the marking protrusions 40, 41, gaps 34 are formed between each of four side surfaces 31 of the cover member 14a and the inner peripheral surface 27 of the body portion 15 of the holders 11b, 11c, and four gaps 34 are arranged in a circumferential direction of the lens units 10C, 10D.

The adhesive material 35 (filler) is injected (filled) in the four gaps 34 formed between each of the side surfaces 31 of the cover member 14a and the inner peripheral surface 27 of the body portion 15 of the holders 11b, 11c, and the adhesive material 35 is hardened in the gaps 34. When the diaphragm pattern 39 is masked by photo-etching on the rear end surface 30 of the cover member 14a, the adhesive material 35 (filler) colored (e.g., black or gray) to block the light is injected (filled) in the gaps 34.

In the small-sized lens unit 10C and small-sized lens unit 10D, the effective area 37 (EBD) of the light beam extending from the lens 12 through the diaphragm 28 (diaphragm aperture) of the copper diaphragm plate 13 (diaphragm means) to the front end surface 29 located at the object side of the cover member 14a appears on the front end surface 29 of the cover member 14a having the regular quadrangular shape (quadrangular shape) (shown in FIG. 6). The effective area 37 (EBD) of the light beam is located inside the light receiving area 38 without being displaced outside the light receiving area 38 having the regular quadrangular shape (quadrangular shape) surrounded by the outer peripheral edge of the front end surface 29 of the cover member 14a.

When one of the lens units 10C, 10D is installed on the distal end of the sensor module 36 (scope) of the endoscope, the light (image) entered from the circular effective area 37 (EBD) located inside the light receiving area 38 of the front end surface 29 of the cover member 14a having the regular quadrangular shape (quadrangular shape) passes through the cover member 14a, passes through the diaphragm 28 (diaphragm aperture) of the copper diaphragm plate 13 (diaphragm means), enters in the lens 12, and then enters in the light receiving element of the sensor module 36 from the lens 12. Thus, the light is outputted (displayed) as an image or outputted as a light signal.

In the lens unit 10C and the lens unit 10D, when the tips of at least one of four corners 32 of the cover member 14a formed in the regular quadrangular prism (quadrangular prism) is separated inward in a radial direction from the inner peripheral surface 27 of the housing space 17 of the body portion 15 of the holders 11b, 11c at a predetermined separate distance, the predetermined separate distance between the tips of the corners 32 and the inner peripheral surface 27 (excluding the marking protrusions 40, 41) of the housing space 17 of the body portion 15 of the holders 11b, 11c is within the range of 0.1 mm or less, and preferably 0.01 mm or more and 0.1 mm or less (0.01 mm to 0.1 mm).

The lens unit 10C and the lens unit 10D have following effects in addition to the effects of the lens unit 10A shown in FIG. 1 and the lens unit 10B shown in FIG. 5. In the lens unit 10C and the lens unit 10D, when the marking protrusion 40 or the marking protrusion 41 is located at the top (upper) portion of the sensor module 36 (scope) or when the marking protrusion 40 or the marking protrusion 41 is located at the bottom (lower) portion of the sensor module 36, for example, the top (upper) portion of the sensor module 36 and the bottom (lower) portion of the sensor module 36 can be easily confirmed by visually recognizing the marking protrusion 40 or the marking protrusion 41. Accordingly, productivity of the image pickup module and workability of assembling to the endoscope can be improved.

Figure 11:
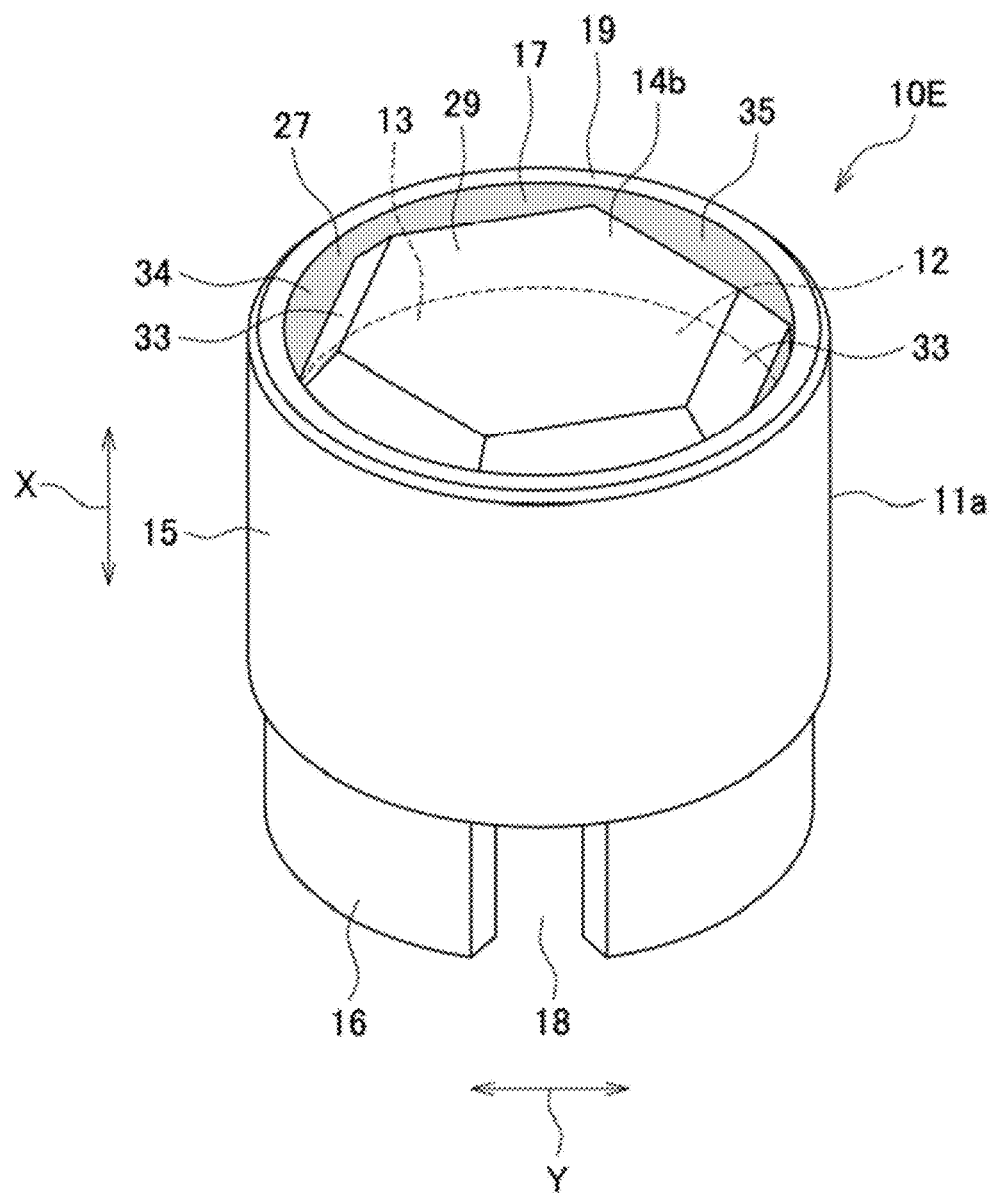
FIG. 11 is a perspective view of the lens unit shown as another example.
Figure 12:
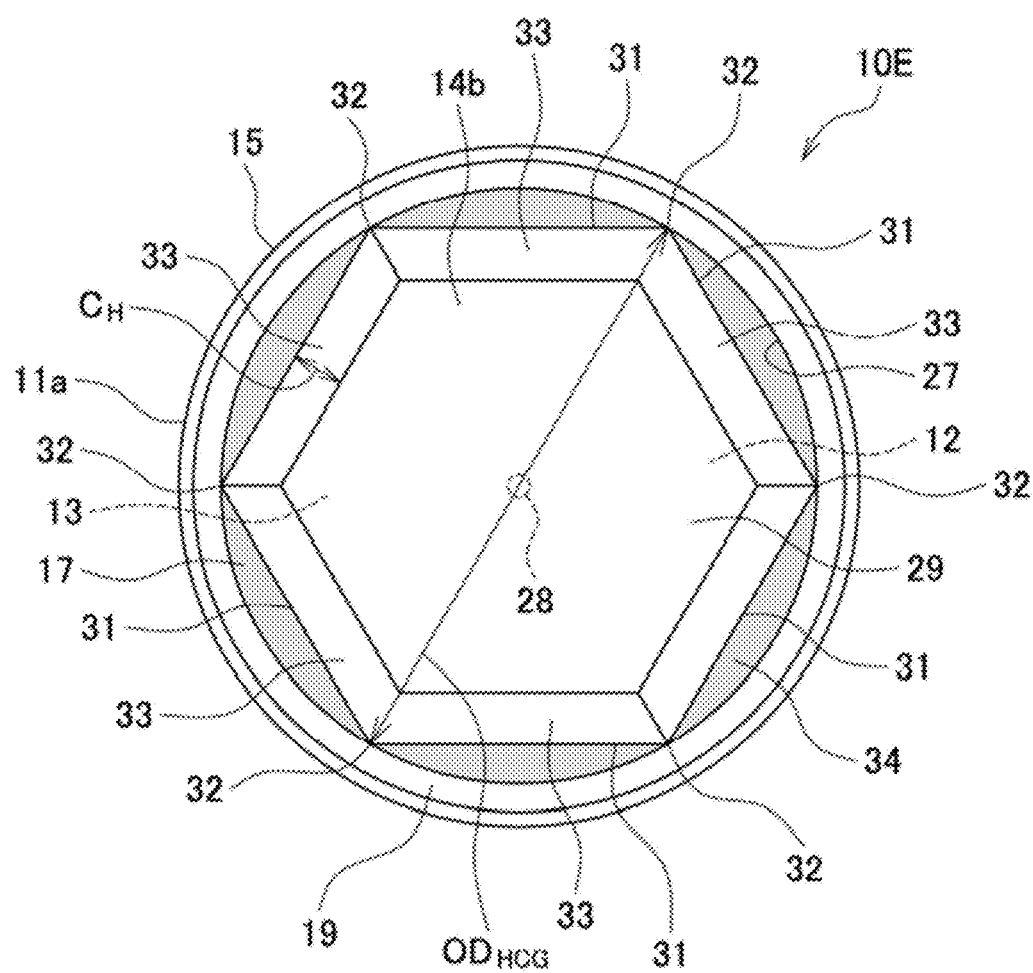
FIG. 12 is a plan view of the lens unit of FIG. 11.

FIG. 11 is a perspective view of a lens unit 10E shown as another example. FIG. 12 is a plan view of the lens unit 10E of FIG. 11. In FIG. 11, an optical axis direction (longitudinal direction) is shown by the arrow mark X and a radial direction is shown by the arrow mark Y. The lens unit 10E shown in FIG. 10 is different from the lens unit shown in FIG. 1 in a point that the side surfaces continuing from the front end surface 29 located at the object side to the rear end surface 30 located at the image side is formed in a regular hexagonal prism (hexagonal prism). Other configurations are same as the lens unit 10A shown in FIG. 1. Thus, same reference numerals as FIG. 1 are added and the detailed explanation about the other configurations of the lens unit 10E will be omitted by referring to the explanation of FIG. 1.

The lens unit 10E is formed by a holder 11a and individually prepared lens 12, copper diaphragm plate 13 (diaphragm means) and cover member 14b formed in the regular hexagonal prism (hexagonal prism). In the lens unit 10E, the copper diaphragm plate 13 is arranged rearward of the cover member 14b in the optical axis direction, and the lens 12 is arranged rearward of the copper diaphragm plate 13 in the optical axis direction. The cover member 14b, the copper diaphragm plate 13 and the lens 12 are arranged in a row (in series) in the optical axis direction.

The cover member 14b, the copper diaphragm plate 13 and the lens 12 are housed in the housing space 17 of the body portion 15 of the holder 11a individually with each other (shown in FIG. 3). The lens 12 and the copper diaphragm plate 13 are same as those of the lens unit 10A. In the lens 12, the entire area of the front end surface 23 is fixed to the copper diaphragm plate 13 by a transparent adhesive material, and the rear end surface 24 of the flange portion 22 is fixed to the flange abutting portion 26 of the housing space 17 of the holder 11a by the adhesive material. Note that, in the lens unit 10E, it is also possible to omit the copper diaphragm plate 13 same as the lens unit 10B shown in FIG. 8 and the diaphragm pattern 39 can be masked by photo-etching on the rear end surface 30 of the cover member 14b.

The cover member 14b is formed by cutting a transparent glass material (cover glass) into a regular hexagonal prism (hexagonal prism) or molding a transparent synthetic resin (cover plastic) into a regular hexagonal prism (hexagonal prism). The cover member 14b includes a front end surface 29 having a flat shape and located at the object side, a rear end surface 30 having a flat shape located at an opposite side (image side) of the front end surface 29, six side surfaces 31 extending between the front and rear end surfaces 29, 30, and six corners 32 where the side surfaces 31 intersect with each other. In the cover member 14b, the side surfaces continuing from the front end surface 29 located at the object side to the rear end surface 30 located at the image side is formed in a regular hexagonal prism (hexagonal prism), and a cross-sectional shape in the radial direction is formed in a regular hexagonal shape (hexagonal shape). Accordingly, the front end surface 29 and the rear end surface 30 are formed in a regular hexagonal shape (hexagonal shape).

In the cover member 14b, the corners where the front end surface 29 and each of the side surfaces 31 intersect are chamfered by cutting the corners, or the corners where the front end surface 29 and each of the side surfaces 31 intersect are chamfered by molding the synthetic resin material. Six chamfered surfaces 33 inclined at a downward gradient from the front end surface 29 to the side surfaces 31 are formed between the front end surface 29 and the side surfaces 31 of the cover member 14b. The front end surface 29 is surrounded by the chamfered surfaces 33. A length $C_H$ of the six chamfered surfaces 33 of the cover member 14b in a radial direction is within the range of 0.3 mm or less, and preferably within the range of 0.05 mm or more and 0.3 mm or less (0.05 mm to 0.3 mm). Note that it is not necessary to chamfer the corners where the front end surface 29 and each of the side surfaces 31 intersect.

The cover member 14b is located at frontward in the optical axis direction of the copper diaphragm plate 13 and fitted (housed) in frontward of the housing space 17 of the body portion 15 of the holder 11a. The tips of all of six corners 32 or the tips of a plurality of six corners 32 of the cover member 14b having the regular hexagonal prism (hexagonal prism) shape are in contact with the inner peripheral surface 27 of the body portion 15 of the holder 11a. The body portion 15 of the holder 11a forms a circumscribed circle of the front and rear end surfaces 29, 30 of the cover member 14b having a regular hexagonal cross-section. Note that it is enough that the tips of at least two of the corners 32 in the six corners 32 of the cover member 14b having the regular hexagonal prism (hexagonal prism) shape are in contact with the inner peripheral surface 27 of the body portion 15 of the holder 11a.

In the regular hexagonal prism (hexagonal prism) of the cover member 14b, a length $OD_{HCG}$ of a diagonal line (maximum diameter in radial direction) is 1.2 mm and an outer shape L2 is approximately 1.04 mm. In the cover member 14b, a thickness $H_{CG}$ from the front end surface 29 to the rear end surface 30 is within the range of 0.01 mm or more and 0.5 mm or less (0.01 mm to 0.5 mm). The length $OD_{HCG}$ of the diagonal line, the outer shape L2 and the thickness $H_{CG}$ of the cover member 14b are appropriately determined according to the type of the sensor module 36 of the endoscope in which the lens unit 10E is used. Although the length $OD_{HCG}$ of the diagonal line, the outer shape L2 and the thickness $H_{CG}$ of the cover member 14b are not particularly limited, it is necessary to specify the length $ODH_{CG}$ of the diagonal line, the outer shape L2 and the thickness $H_{CG}$ so as to be capable of being housed in the housing space 17 of the body portion 15 of the holder 11a.

The outer diameter $OD_{HL}$ of the body portion 15 of the holder 11a (diameter of body portion 15 of holder 11a) is same as that of the lens unit 10A and adjusted within the range of 0.5 mm to 10 mm. The inner diameter $ID_{HL}$ of the body portion 15 of the holder 11a (housing space 17 for housing cover member 14b) is same as that of the lens unit 10A and is within the range of 0.4 mm or more and 8 mm or less (0.4 mm to 8 mm). When the outer diameter $OD_{HL}$ of the body portion 15 of the holder 11a is within the range of 0.5 mm to 10 mm and the inner diameter $ID_{HL}$ of the body portion 15 of the holder 11a is 0.4 mm or more and 8 mm or less, an extremely small-sized lens unit 10E can be formed by housing the lens 12, the copper diaphragm plate 13 and the cover member 14b in the housing space 17 of the body portion 15 of the holder 11a. Accordingly, the lens unit 10E is capable of being suitably connected to the small-sized sensor module 36.

In the lens unit 10E, when the cover member 14b having a regular hexagonal cross-sectional shape (hexagonal cross-sectional shape) is fitted (housed) in the housing space 17 of the body portion 15 of the holder 11a having a circular cross-sectional shape, gaps 34 are formed between each of six side surfaces 31 of the cover member 14b and the inner peripheral surface 27 of the body portion 15 of the holder 11a, and six gaps 34 are arranged in a circumferential direction of the lens unit 10E.

The adhesive material 35 (filler) is injected (filled) in the six gaps 34 formed between each of the side surfaces 31 of the cover member 14b and the inner peripheral surface 27 of the body portion 15 of the holder 11a, and the adhesive material 35 is hardened in the gaps 34. When the diaphragm pattern 39 is masked by photo-etching on the rear end surface 30 of the cover member 14b, the adhesive material 35 (filler) colored (e.g., black or gray) to block the light is injected (filled) in the gaps 34.

Figure 14:
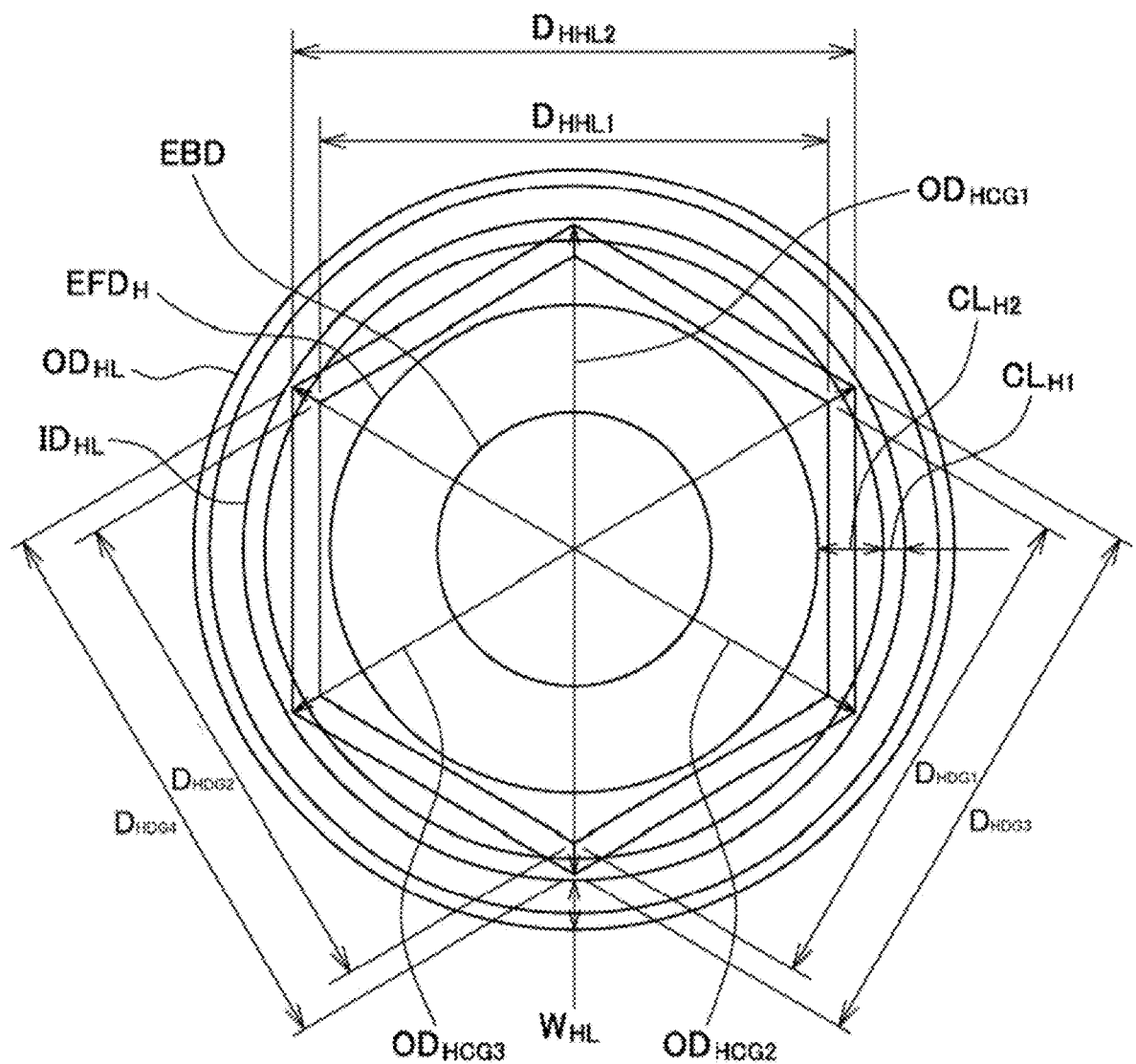
FIG. 14 is a diagram continued from FIG. 13 for explaining an example of the calculation of various values related to the cover member.

In the lens unit 10E, the effective area 37 (EBD) of the light beam extending from the lens 12 through the diaphragm 28 (diaphragm aperture) of the copper diaphragm plate 13 (diaphragm means) to the front end surface 29 located at the object side of the cover member 14b appears on the front end surface 29 of the cover member 14b having the regular hexagonal shape (hexagonal shape) (shown in FIG. 14). The effective area 37 (EBD) of the light beam appeared on the front end surface 29 of the cover member 14b has a circular (complete round) shape. The effective area 37 (EBD) of the light beam is located inside a light receiving area 38 without being displaced outside the light receiving area 38 having the regular hexagonal shape (hexagonal shape) surrounded by the outer peripheral edge of the front end surface 29 of the cover member 14b.

When the lens unit 10E is installed on the distal end of the sensor module 36 (scope) of the endoscope, the light (image) entered from the circular effective area 37 (EBD) located inside the light receiving area 38 of the front end surface 29 of the cover member 14b having the regular hexagonal shape (hexagonal shape) passes through the cover member 14b, passes through the diaphragm 28 (diaphragm aperture) of the copper diaphragm plate 13 (diaphragm means), enters in the lens 12, and then enters in the light receiving element of the sensor module 36 from the lens 12. Thus, the light is outputted (displayed) as an image or outputted as a light signal.

In the lens unit 10E, when the tips of at least one of six corners 32 of the cover member 14b formed in the regular hexagonal prism (hexagonal prism) is separated inward in a radial direction from the inner peripheral surface 27 of the housing space 17 of the body portion 15 of the holder 11a at a predetermined separate distance, the predetermined separate distance between the tips of the corners 32 and the inner peripheral surface 27 of the housing space 17 of the body portion 15 of the holder 11a is within the range of 0.1 mm or less, and preferably 0.01 mm or more and 0.1 mm or less (0.01 mm to 0.1 mm).

Figure 13:
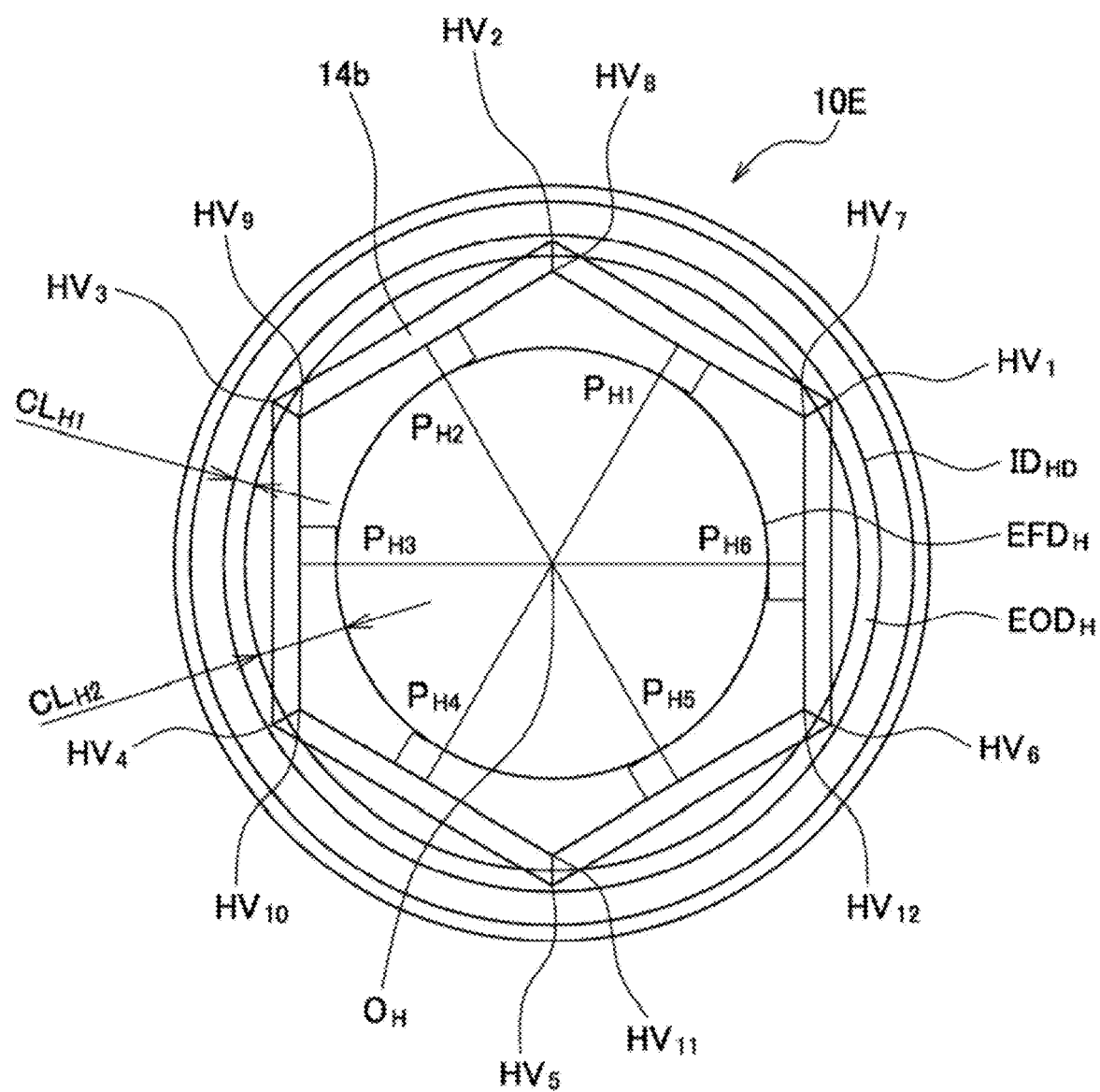
FIG. 13 is a diagram for explaining an example of the calculation of various values related to the cover member.

FIG. 13 is a diagram for explaining an example of the calculation of various values related to the cover member 14b. In the lens unit 10E shown in FIG. 11, the effective area EBD of the light beam, the effective area $EFD_H$ of the front end surface 29 (planar part) of the cover member 14b, outer shapes $D_{HHL2}$, $D_{HDG3}$ and $D_{HDG4}$ of the cover member 14b, the length $OD_{HCG}$ of the diagonal line of the cover member 14b, the inner diameter $ID_{HL}$ of the body portion 15 of the holder 11a, and the outer diameter $OD_{HL}$ of the body portion 15 of the holder 11a are calculated by the calculation explained below. Note that the objects indicated by each symbol shown in FIG. 13 are as follows.

$ID_{HL}$: Inner diameter of body portion 15 of holder 11a $CL_{H1}$: Variation tolerance area of apexes (corners) of cover member 14b $CL_{H2}$: Variation tolerance area of front end surface 29 of cover member 14b $HV_{1-6}$: Apexes (corners) of cover member 14b $HV_{7-12}$: Apexes (corners) of front end surface 29 of cover member 14b $EFD_H$: Light receiving area 38 of front end surface 29 of cover member 14b $EOD_H$: Effective area of outer shape of cover member 14b The variation tolerance area of the apexes of the cover member 14b is $CL_{H1} \leq 0.1$ mm, and the variation tolerance area of the front end surface 29 of the cover member 14b is $CL_{H2} \leq 0.9$ mm. The apexes $HV_{1-6}$ of the cover member 14b are within the range of $CL_{H1}$.

In the apexes $HV_{7-12}$ of the front end surface 29 of the cover member 14b, when a perpendicular lines are drawn from the center $O_H$ to straight lines connecting the neighboring apexes, the length of the perpendicular lines ($P_{H1}$ to $P_{H6}$) follows the conditions below. When $CL_{H2}$ is 0, it means that the chamfered surface C is not formed.

Figure 15:
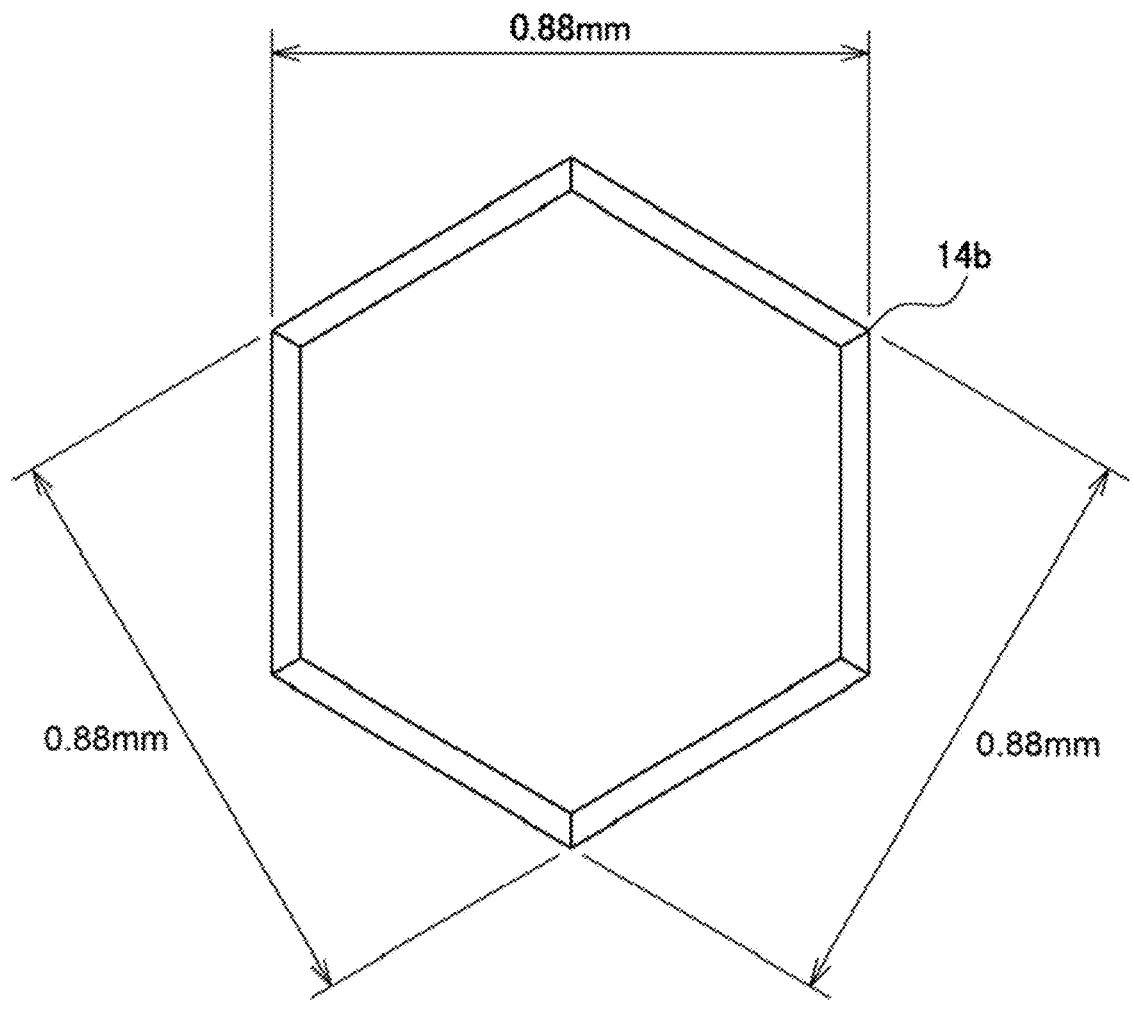
FIG. 15 is a diagram showing calculated outer shape, thickness and length of chamfered surface C in a radial direction of the cover member.
Figure 15:
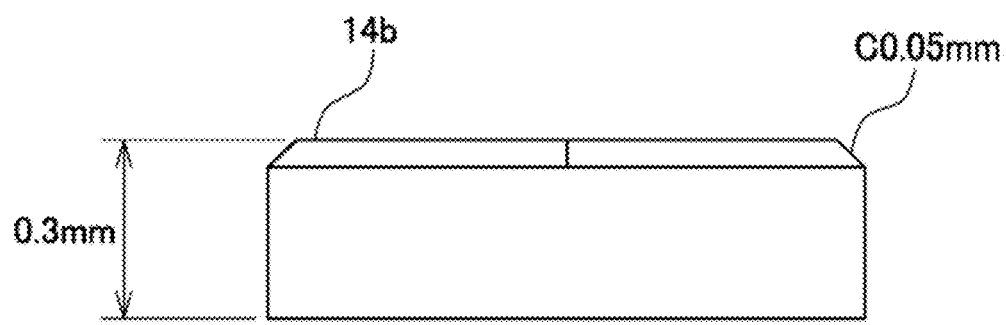

$P_{H1} \geq EFD_H/2$
$P_{H2} \geq EFD_H/2$
$P_{H3} \geq EFD_H/2$
$P_{H4} \geq EFD_H/2$
$P_{H5} \geq EFD_H/2$
$P_{H6} \geq EFD_H/2$ FIG. 14 is a diagram continued from FIG. 13 for explaining an example of the calculation of various values related to the cover member 14b. FIG. 15 is a diagram showing calculated outer shape, thickness and length of chamfered surface C in a radial direction of the cover member 14b. The objects indicated by each symbol shown in FIG. 14 are as follows.

$ID_{HL}$: Inner diameter of holder 11a
$OD_{HL}$: Outer diameter of holder 11a
$W_{HL}$: Thickness of body portion 15 of holder 11a $CL_{H1}$: Variation tolerance area of apexes (corners) of cover member 14b $CL_{H2}$: Variation tolerance area of front end surface 29 of cover member 14b EBD: Diameter of effective area 37 of light beam $EFD_H$: light receiving area 38 of front end surface 29 of cover member 14b $D_{HHL1}$: Length (horizontal) of outer shape of front end surface 29 of cover member 14b $D_{HDG1}$: Length (oblique) of outer shape of front end surface 29 of cover member 14b $D_{HDG2}$: Length (oblique) of outer shape of front end surface 29 of cover member 14b $OD_{HCG1}$: Length (diagonal) of outer shape of cover member 14b $OD_{HCG2}$: Length (diagonal) of outer shape of cover member 14b $OD_{HCG3}$: Length (diagonal) of outer shape of cover member 14b The length (size) of each part of the cover member 14b is determined based on the diameter EBD of the effective area 37 of the light beam. $D_{HHL1}$, $D_{HDG1}$ and $D_{HDG2}$ follow the conditions below, and $OD_{HCG1}$, $OD_{HCG2}$ and $OD_{HCG3}$ follow the conditions below.

$D_{HHL1} \geq EFD_H \geq EBD + CL_{H1}$
$D_{HDG1} \geq EFD_H \geq EBD + CL_{H1}$
$D_{HDG2} \geq EFD_H \geq EBD + CL_{H1}$
$ID_{HL} \geq OD_{HCG1} \geq EFD_H + CL_{H2}$
$ID_{HL} \geq OD_{HCG2} \geq EFD_H + CL_{H2}$
$ID_{HL} \geq OD_{HCG3} \geq EFD_H + CL_{H2}$ The size of the cover member 14b is determined by the above described conditions. In addition, the size of the outer diameter of the holder 11a is determined by the following (Formula 2).

$$OD_{HL} = ID_{HL} + W_{HL} \quad \text{(Formula 2)}$$

The length $C_H$ of the chamfered surface C in a radial direction and the thickness of the body portion 15 of the holder 11a are specified within the following range.

Length of chamfered surface C of cover member 14b: $0 \text{ mm} \leq C_H \leq 0.3 \text{ mm}$ Thickness of body portion 15 of holder 11a: $0.01 \text{ mm} \leq W_{HL} \leq 1 \text{ mm}$ A tolerance is determined considering the processing method of the cover member 14b. At that time, be sure to confirm that the size is not out of the range explained in FIG. 13.

Concrete examples of the calculation of various values related to the cover member 14b having a regular hexagonal prism shape are shown below. The conditions of the concrete examples of the calculation of various values are same as the conditions of the concrete examples of the calculation of various values in the cover member 14a formed in the regular quadrangular prism. Note that the diameter EBD (EBD=0.7 mm) of the effective area 37 of the light beam and the light receiving area 38 ($EFD_H$=0.78 mm) of the front end surface 29 of the cover member 14b are same as those of the cover member 14a of the regular quadrangular prism.

(1) Calculation of outer shape of cover member 14b $$\begin{aligned} D_{HHL2} &= D_{HDG3} \\ &= D_{HDG4} \\ &= D_{HHL1} + C_H * 2 \\ &= 0.78 + 0.05 * 2 \\ &= 0.88 \text{ mm} \end{aligned}$$

(2) Calculation of length of diagonal line of cover member 14b $$\begin{aligned} OD_{HCG} &= 2 * (D_{HHL2}/2) / \cos 30° \\ &= 2 * (0.88/2) / \cos 30° \\ &\approx 1.016 \text{ mm} \end{aligned}$$

(3) Calculation of inner diameter of holder 11a $$\begin{aligned} ID_{HL} &= OD_{HCG} + CL_{S1} * 2 \\ &= 1.016 + 0.04 * 2 \\ &= 1.096 \text{ mm} \end{aligned}$$

(4) Calculation of outer diameter of body portion 15 of holder 11a $$\begin{aligned} OD_{HL} &= ID_{HL} + W_{HL} * 2 \\ &= 1.096 + 0.1 * 2 \\ &= 1.296 \text{ m} \end{aligned}$$

As the calculated size of the cover member 14b, as shown in FIG. 15, the outer shape of the cover member 14b is 0.88 mm, the thickness of the cover member 14b is 0.3 mm, and the length of the chamfered surface C in a radial direction is 0.05 mm.

In the lens unit 10E, the side surfaces 31 of the cover member 14b (cover glass or cover plastic) continuing from the front end surface 29 to the rear end surface 30 can be easily formed in the regular hexagonal prism (hexagonal prism) by cutting a glass material or molding a synthetic resin material. Unlike the conventional lens unit 50 shown in FIGS. 26 and 27, handwork of artisans is not required for polishing the outer peripheral surface of the cover glass 55 so that the cover glass 55 has a complete round cross-sectional shape. Accordingly, the lens unit 10E having the cover member 14b formed in a regular hexagonal prism (hexagonal prism) can be mechanically and efficiently manufactured.

In the lens unit 10E, the cover member 14b (cover glass or cover plastic) can be manufactured by cutting a glass material in the regular hexagonal prism (hexagonal prism) or molding a synthetic resin material into the regular hexagonal prism (hexagonal prism). Thus, the cover member 14b can be manufactured at low cost without depending on skilled artisans. In addition, the lens unit 10E having the cover member 14b which is formed in the regular hexagonal prism (hexagonal prism) and does not cause deviation in precision can be manufactured at low cost. Accordingly, production efficiency of the lens unit 10E can be increased.

In the lens unit 10E, the tips of at least two of six corners 32 of the regular hexagonal prism (hexagonal prism) of the cover member 14b (cover glass or cover plastic) are in contact with the inner peripheral surface 27 of the body portion 15. Thus, the cover member 14b formed in the regular hexagonal prism can be fixed to the housing space 17 of the body portion 15 of the holder 11a while preventing the cover member 14b from moving in the housing space 17 of the body portion 15 of the holder 11a.

In the lens unit 10E, the circular effective area 37 (EBD) of the light beam is located inside the light receiving area 38 having the regular hexagonal shape (hexagonal shape) surrounded by the outer peripheral edge of the front end surface 29 of the cover member 14b (cover glass or cover plastic). Thus, a part of the effective area 37 (EBD) of the light beam is not displaced (protruded) outside the light receiving area 38 having a regular hexagonal shape. Accordingly, the accurate image can be formed on the lens unit 10E.

In the lens unit 10E, when the side surfaces 31 of the cover member 14b (cover glass or cover plastic) are formed in the regular hexagonal prism (hexagonal prism), the corners can be easily chamfered by cutting the corners where the front end surface 29 of the cover member 14b and each of the six side surfaces 31 intersect or the corners can be easily chamfered by molding the synthetic resin material. Accordingly, unexpected breakage and damage of the corners of the cover member 14b can be prevented by chamfering the corners of the cover member 14b.

When tips of at least one of six corners 32 of the cover member 14b formed in the regular hexagonal prism (hexagonal prism) is separated inward in a radial direction from the inner peripheral surface 27 of the housing space 17 of the body portion 15 of the holder 11a at a predetermined separate distance, if the predetermined separate distance between the tips of the corners 32 and the inner peripheral surface 27 of the housing space 17 exceeds 0.1 mm, a part of the circular effective area 37 (EBD) of the light beam may be displaced (protruded) outside the light receiving area 38 having the regular hexagonal shape (hexagonal shape) surrounded by the outer peripheral edge of the front end surface 29 of the cover member 14b when the cover member 14b is moved in the housing space 17 of the body portion 15 of the holder 11a. In such a case, the accurate image cannot be formed on the lens unit 10E. However, since the predetermined separate distance between the tips of the corners 32 and the inner peripheral surface 27 of the housing space 17 of the body portion 15 of the holder 11a is within the range of 0.1 mm or less and preferably 0.01 mm to 0.1 mm in the lens unit 10E, a part of the effective area 37 (EBD) of the light beam is not displaced (protruded) outside the light receiving area 38 of the front end surface 29 of the cover member 14b even when the cover member 14b (cover glass or cover plastic) is moved in the housing space 17 of the body portion 15 of the holder 11a. Thus, the effective area 37 (EBD) of the light beam can be located inside the light receiving area 38 of the front end surface 29 of the cover member 14b. Accordingly, the accurate image can be formed on the lens unit 10E.

If the length $C_H$ of the chamfered surface C exceeds 0.3 mm in a radial direction, the light receiving area 38 having the regular hexagonal shape (hexagonal shape) surrounded by the outer peripheral edge of the front end surface 29 of the cover member 14b becomes small and a part of the effective area 37 (EBD) of the light beam may be located (displaced) outside the light receiving area 38 having the regular hexagonal shape (hexagonal shape) surrounded by the outer peripheral edge of the front end surface 29 of the cover member 14b. Thus, the accurate image cannot be formed on the lens unit 10E. However, since the length $C_H$ of the chamfered surface C of the lens unit 10E is 0.3 mm or less in the radial direction and preferably 0.05 mm to 0.3 mm, the effective area 37 (EBD) of the light beam can be located inside the light receiving area 38 having the regular hexagonal shape (hexagonal shape) surrounded by the outer peripheral edge of the front end surface 29 of the cover member 14b (cover glass or cover plastic). Thus, the accurate image can be formed on the lens unit 10E while preventing a part of the effective area 37 (EBD) of the light beam from being located (displaced) outside the light receiving area 38 of the front end surface 29 of the cover member 14b.

Figure 16:
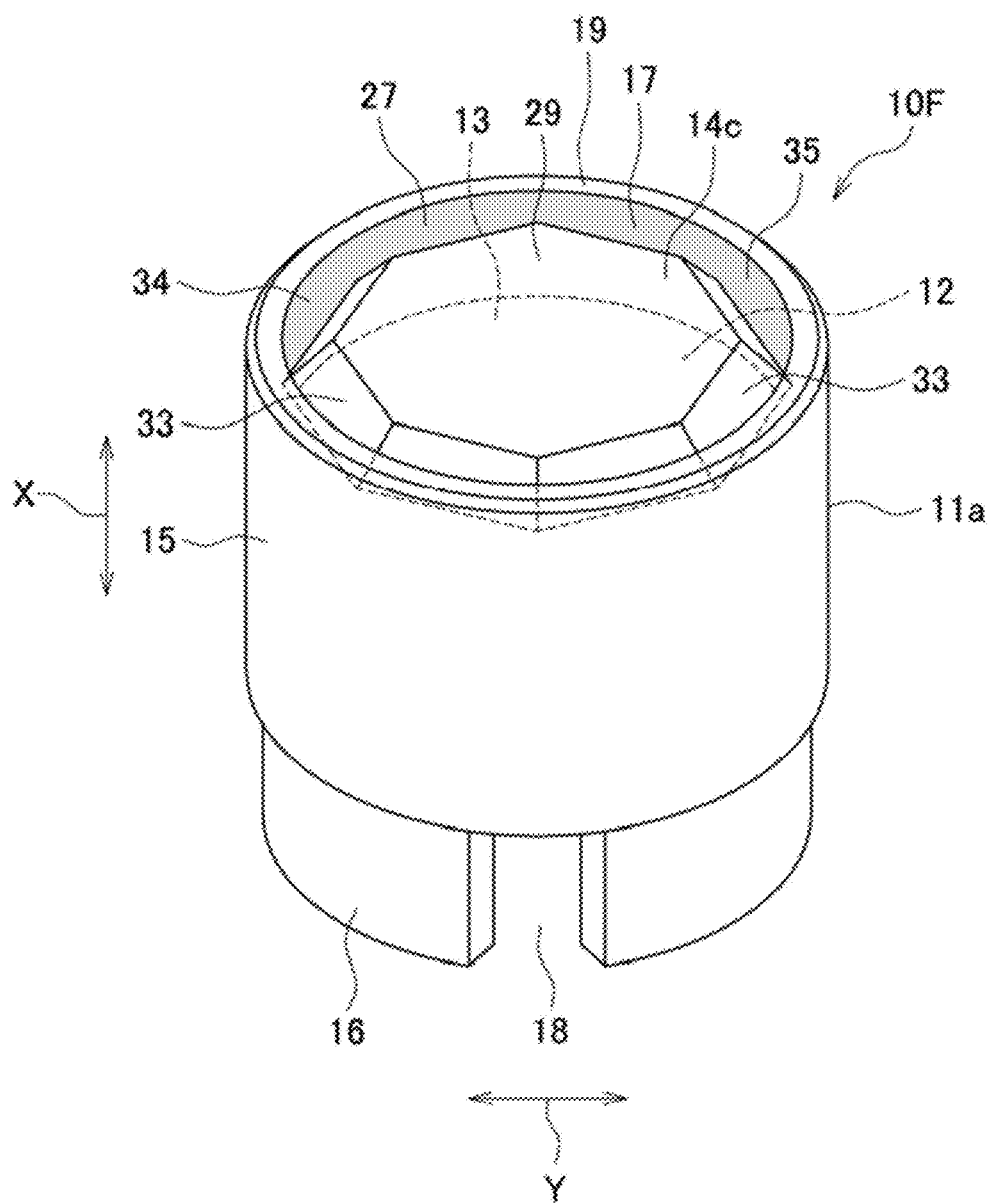
FIG. 16 is a perspective view of the lens unit shown as another example.
Figure 17:
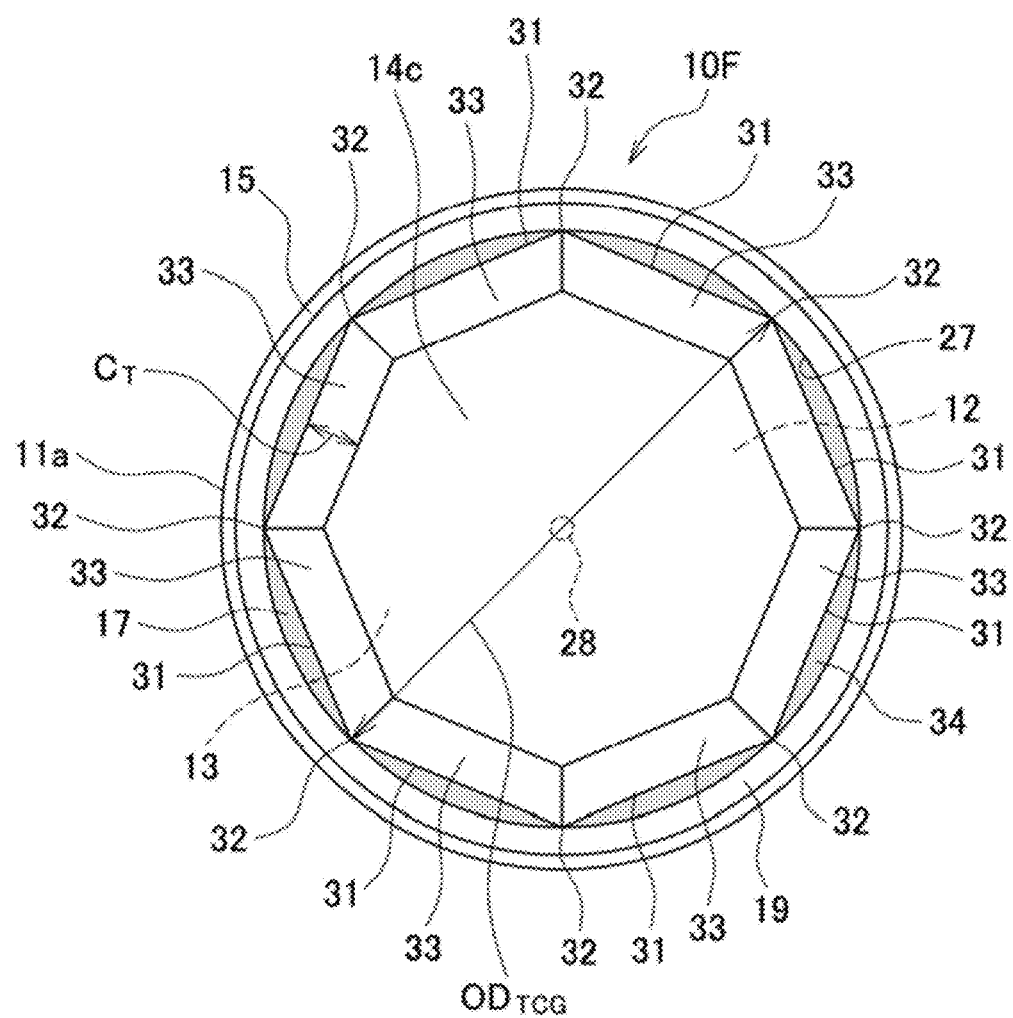
FIG. 17 is a plan view of the lens unit of FIG. 16.

FIG. 16 is a perspective view of a lens unit 10F shown as another example. FIG. 17 is a plan view of the lens unit 10F of FIG. 16. In FIG. 16, an optical axis direction (longitudinal direction) is shown by the arrow mark X and a radial direction is shown by the arrow mark Y. The lens unit 10F shown in FIG. 16 is different from the lens unit shown in FIG. 1 in a point that the side surfaces continuing from the front end surface 29 located at the object side to the rear end surface 30 located at the image side is formed in a regular octagonal prism (octagonal prism). Other configurations are same as the lens unit 10A shown in FIG. 1. Thus, same reference numerals as FIG. 1 are added and the detailed explanation about the other configurations of the lens unit 10F will be omitted by referring to the explanation of FIG. 1.

The lens unit 10F is formed by a holder 11a and individually prepared lens 12, copper diaphragm plate 13 (diaphragm means) and cover member 14c formed in the regular octagonal prism (octagonal prism). In the lens unit 10F, the copper diaphragm plate 13 is arranged rearward of the cover member 14c in the optical axis direction, and the lens 12 is arranged rearward of the copper diaphragm plate 13 in the optical axis direction. The cover member 14c, the copper diaphragm plate 13 and the lens 12 are arranged in a row (in series) in the optical axis direction.

The cover member 14c, the copper diaphragm plate 13 and the lens 12 are housed in the housing space 17 of the body portion 15 of the holder 11a individually with each other (shown in FIG. 3). The lens 12 and the copper diaphragm plate 13 are same as those of the lens unit 10A. In the lens 12, the entire area of the front end surface 23 is fixed to the copper diaphragm plate 13 by a transparent adhesive material, and the rear end surface 24 of the flange portion 22 is fixed to the flange abutting portion 26 of the housing space 17 of the holder 11a by the adhesive material. Note that, in the lens unit 10F, it is also possible to omit the copper diaphragm plate 13 same as the lens unit 10B shown in FIG. 8 and the diaphragm pattern 39 can be masked by photo-etching on the rear end surface 30 of the cover member 14c.

The cover member 14c is formed by cutting a transparent glass material (cover glass) into a regular octagonal prism (octagonal prism) or molding a transparent synthetic resin (cover plastic) into a regular octagonal prism (octagonal prism). The cover member 14c includes a front end surface 29 having a flat shape and located at the object side, a rear end surface 30 having a flat shape located at an opposite side (image side) of the front end surface 29, eight side surfaces 31 extending between the front and rear end surfaces 29, 30, and eight corners 32 where the side surfaces 31 intersect with each other. In the cover member 14c, the side surfaces 31 continuing from the front end surface 29 located at the object side to the rear end surface 30 located at the image side is formed in a regular octagonal prism (octagonal prism), and a cross-sectional shape in the radial direction is formed in a regular octagonal shape (octagonal shape). Accordingly, the front end surface 29 and the rear end surface 30 are formed in a regular octagonal shape (octagonal shape).

In the cover member 14c, the corners where the front end surface 29 and each of the side surfaces 31 intersect are chamfered by cutting the corners, or the corners where the front end surface 29 and each of the side surfaces 31 intersect are chamfered by molding the synthetic resin material. Eight chamfered surfaces 33 inclined at a downward gradient from the front end surface 29 to the side surfaces 31 are formed between the front end surface 29 and the side surfaces 31 of the cover member 14c. The front end surface 29 is surrounded by the chamfered surfaces 33. A length $C_T$ of the eight chamfered surfaces 33 of the cover member 14c in a radial direction is within the range of 0.3 mm or less, and preferably within the range of 0.05 mm or more and 0.3 mm or less (0.05 mm to 0.3 mm). Note that it is not necessary to chamfer the corners where the front end surface 29 and each of the side surfaces 31 intersect.

The cover member 14c is located at frontward in the optical axis direction of the copper diaphragm plate 13 and fitted (housed) in frontward of the housing space 17 of the body portion 15 of the holder 11a. The tips of all of eight corners 32 or the tips of a plurality of eight corners 32 of the cover member 14c having the regular octagonal prism (octagonal prism) shape are in contact with the inner peripheral surface 27 of the body portion 15 of the holder 11a. The body portion 15 of the holder 11a forms a circumscribed circle of the front and rear end surfaces 29, 30 of the cover member 14c having a regular octagonal cross-section. Note that it is enough that the tips of at least two of the corners 32 in the eight corners 32 of the cover member 14c having the regular octagonal prism (octagonal prism) shape are in contact with the inner peripheral surface 27 of the body portion 15 of the holder 11a.

In the regular octagonal prism (octagonal prism) of the cover member 14c, a length $OD_{TCG}$ of a diagonal line (maximum diameter in radial direction) is 1.2 mm and an outer shape L2 is approximately 1.11 mm. In the cover member 14c, a thickness $H_{CG}$ from the front end surface 29 to the rear end surface 30 is within the range of 0.01 mm or more and 0.5 mm or less (0.01 mm to 0.5 mm). The length $OD_{TCG}$ of the diagonal line, the outer shape L2 and the thickness $H_{CG}$ of the cover member 14c are appropriately determined according to the type of the sensor module 36 of the endoscope in which the lens unit 10F is used. Although the length $OD_{TCG}$ of the diagonal line, the outer shape L2 and the thickness $H_{CG}$ of the cover member 14c are not particularly limited, it is necessary to specify the length $OD_{TCG}$ of the diagonal line, the outer shape L2 and the thickness $H_{CG}$ so as to be capable of being housed in the housing space 17 of the body portion 15 of the holder 11a.

The outer diameter $OD_{HL}$ of the body portion 15 of the holder 11a (diameter of body portion 15 of holder 11a) is same as that of the lens unit 10A and adjusted within the range of 0.5 mm to 10 mm. The inner diameter $ID_{HL}$ of the body portion 15 of the holder 11a (housing space 17 for housing cover member 14c) is same as that of the lens unit 10A and is within the range of 0.4 mm or more and 8 mm or less (0.4 mm to 8 mm). When the outer diameter $OD_{HL}$ of the body portion 15 of the holder 11a is within the range of 0.5 mm to 10 mm and the inner diameter $ID_{HL}$ of the body portion 15 of the holder 11a is 0.4 mm or more and 8 mm or less, an extremely small-sized lens unit 10F can be formed by housing the lens 12, the copper diaphragm plate 13 and the cover member 14c in the housing space 17 of the body portion 15 of the holder 11a. Accordingly, the lens unit 10F is capable of being suitably connected to the small-sized sensor module 36.

In the lens unit 10F, when the cover member 14c having a regular octagonal cross-sectional shape (octagonal cross-sectional shape) is fitted (housed) in the housing space 17 of the body portion 15 of the holder 11a having a circular cross-sectional shape, gaps 34 are formed between each of eight side surfaces 31 of the cover member 14c and the inner peripheral surface 27 of the body portion 15 of the holder 11a, and eight gaps 34 are arranged in a circumferential direction of the lens unit 10F.

The adhesive material 35 (filler) is injected (filled) in the eight gaps 34 formed between each of the side surfaces 31 of the cover member 14c and the inner peripheral surface 27 of the body portion 15 of the holder 11a, and the adhesive material 35 is hardened in the gaps 34. When the diaphragm pattern 39 is masked by photo-etching on the rear end surface 30 of the cover member 14c, the adhesive material 35 (filler) colored (e.g., black or gray) to block the light is injected (filled) in the gaps 34.

Figure 19:
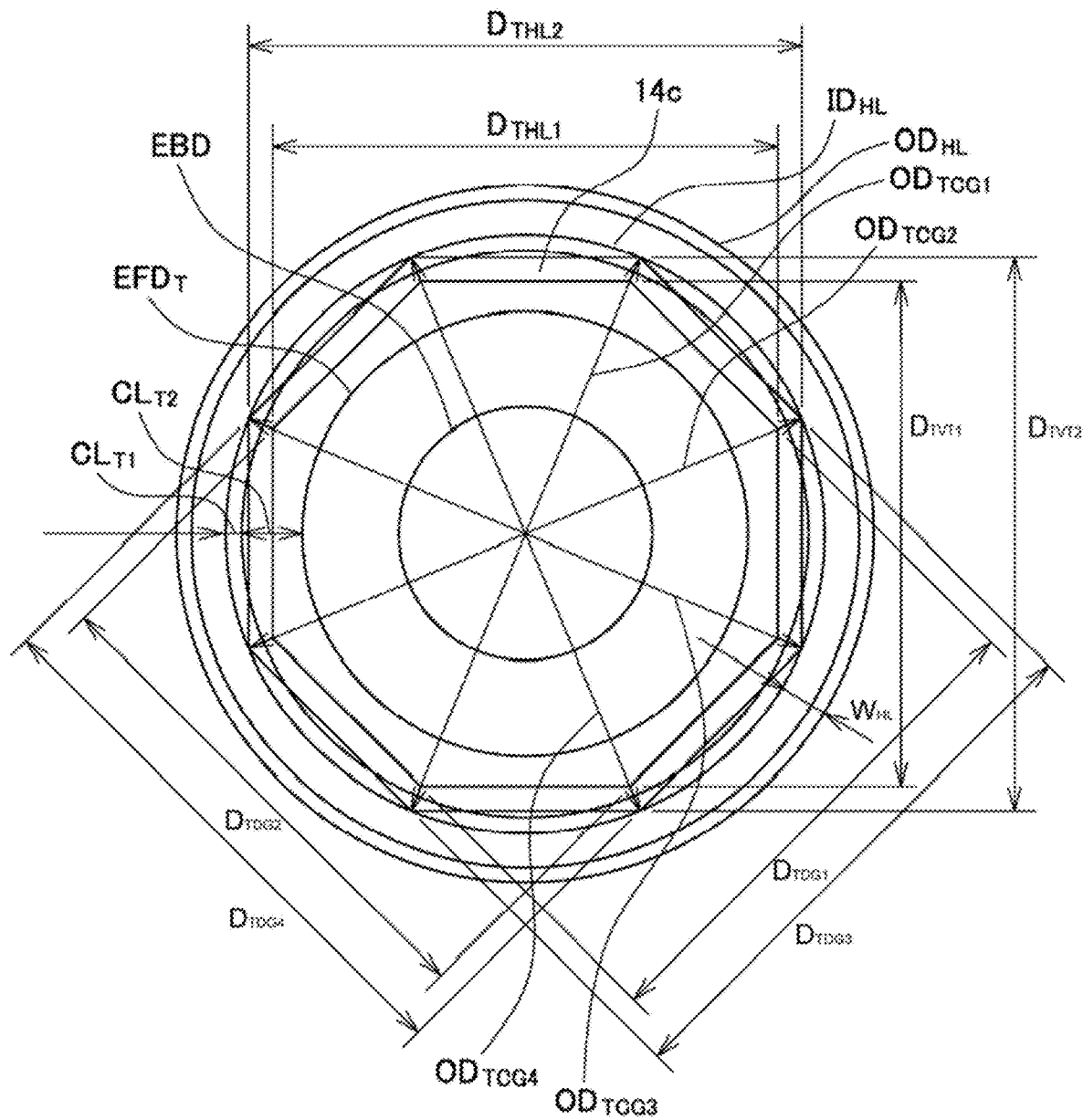
FIG. 19 is a diagram continued from FIG. 18 for explaining an example of the calculation of various values related to the cover member.

In the lens unit 10F, the effective area 37 (EBD) of the light beam extending from the lens 12 through the diaphragm 28 (diaphragm aperture) of the copper diaphragm plate 13 (diaphragm means) to the front end surface 29 located at the object side of the cover member 14c appears on the front end surface 29 of the cover member 14c having the regular octagonal shape (octagonal shape) (shown in FIG. 19). The effective area 37 (EBD) of the light beam appeared on the front end surface 29 of the cover member 14c has a circular (complete round) shape. The effective area 37 (EBD) of the light beam is located inside a light receiving area 38 without being displaced outside the light receiving area 38 having the regular octagonal shape (octagonal shape) surrounded by the outer peripheral edge of the front end surface 29 of the cover member 14c.

When the lens unit 10F is installed on the distal end of the sensor module 36 (scope) of the endoscope, the light (image) entered from the circular effective area 37 (EBD) located inside the light receiving area 38 of the front end surface 29 of the cover member 14c having the regular octagonal shape (octagonal shape) passes through the cover member 14c, passes through the diaphragm 28 (diaphragm aperture) of the copper diaphragm plate 13 (diaphragm means), enters in the lens 12, and then enters in the light receiving element of the sensor module 36 from the lens 12. Thus, the light is outputted (displayed) as an image or outputted as a light signal.

In the lens unit 10F, when the tips of at least one of eight corners 32 of the cover member 14c formed in the regular octagonal prism (octagonal prism) is separated inward in a radial direction from the inner peripheral surface 27 of the housing space 17 of the body portion 15 of the holder 11a at a predetermined separate distance, the predetermined separate distance between the tips of the corners 32 and the inner peripheral surface 27 of the housing space 17 of the body portion 15 of the holder 11a is within the range of 0.1 mm or less, and preferably 0.01 mm or more and 0.1 mm or less (0.01 mm to 0.1 mm).

Figure 18:
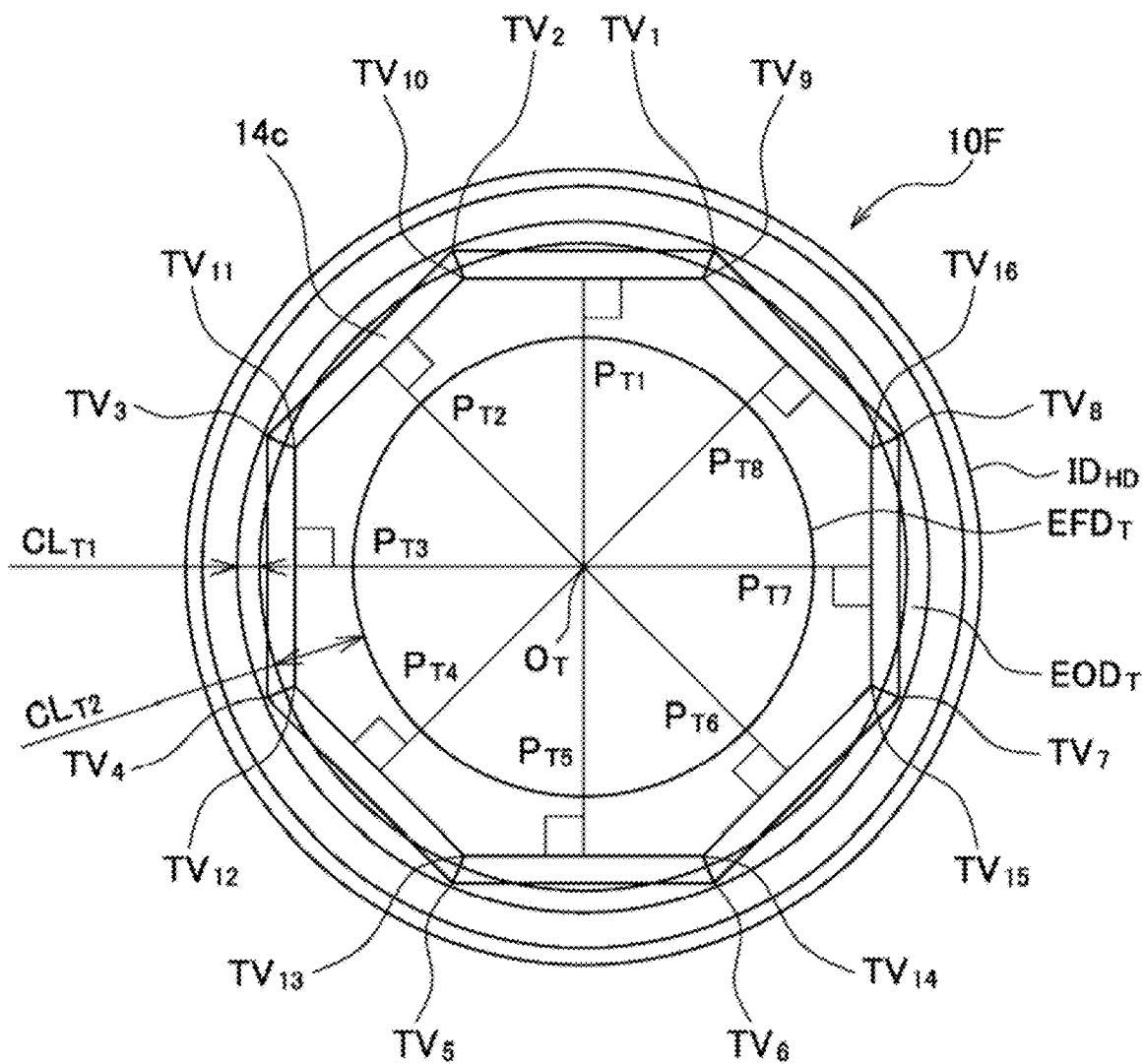
FIG. 18 is a diagram for explaining an example of the calculation of various values related to the cover member.

FIG. 18 is a diagram for explaining an example of the calculation of various values related to the cover member 14c. In the lens unit 10F shown in FIG. 16, the effective area EBD of the light beam, the effective area $EFD_T$ of the front end surface 29 (planar part) of the cover member 14c, outer shapes $D_{TVT2}$, $D_{THL2}$, $D_{TDG3}$, $D_{TDG4}$ of the cover member 14c, the length $OD_{TCG}$ of the diagonal line of the cover member 14c, the inner diameter $ID_{HL}$ of the body portion 15 of the holder 11a, and the outer diameter $OD_{HL}$ of the body portion 15 of the holder 11a are calculated by the calculation explained below. Note that the objects indicated by each symbol shown in FIG. 18 are as follows.

$ID_{HL}$: Inner diameter of body portion 15 of holder 11a $CL_{T1}$: Variation tolerance area of apexes (corners) of cover member 14c $CL_{T2}$: Variation tolerance area of front end surface 29 of cover member 14c $TV_{1-8}$: Apexes (corners) of cover member 14c $TV_{9-16}$: Apexes (corners) of front end surface 29 of cover member 14c $EFD_T$: Light receiving area 38 of front end surface 29 of cover member 14c $EOD_T$: Effective area of outer shape of cover member 14c The variation tolerance area of the apexes of the cover member 14c is $CL_{T1} \leq 0.1$ mm, and the variation tolerance area of the front end surface 29 of the cover member 14c is $CL_{T2} \leq 0.6$ mm. The apexes $TV_{1-8}$ of the cover member 14c are within the range of $CL_{T1}$.

In the apexes $TV_{9-16}$ of the front end surface 29 of the cover member 14c, when a perpendicular lines are drawn from the center OT to straight lines connecting the neighboring apexes, the length of the perpendicular lines ($P_{T1}$ to $P_{T8}$) follows the conditions below.

When $CL_{T2}$ is 0, it means that the chamfered surface C is not formed.

Figure 20:
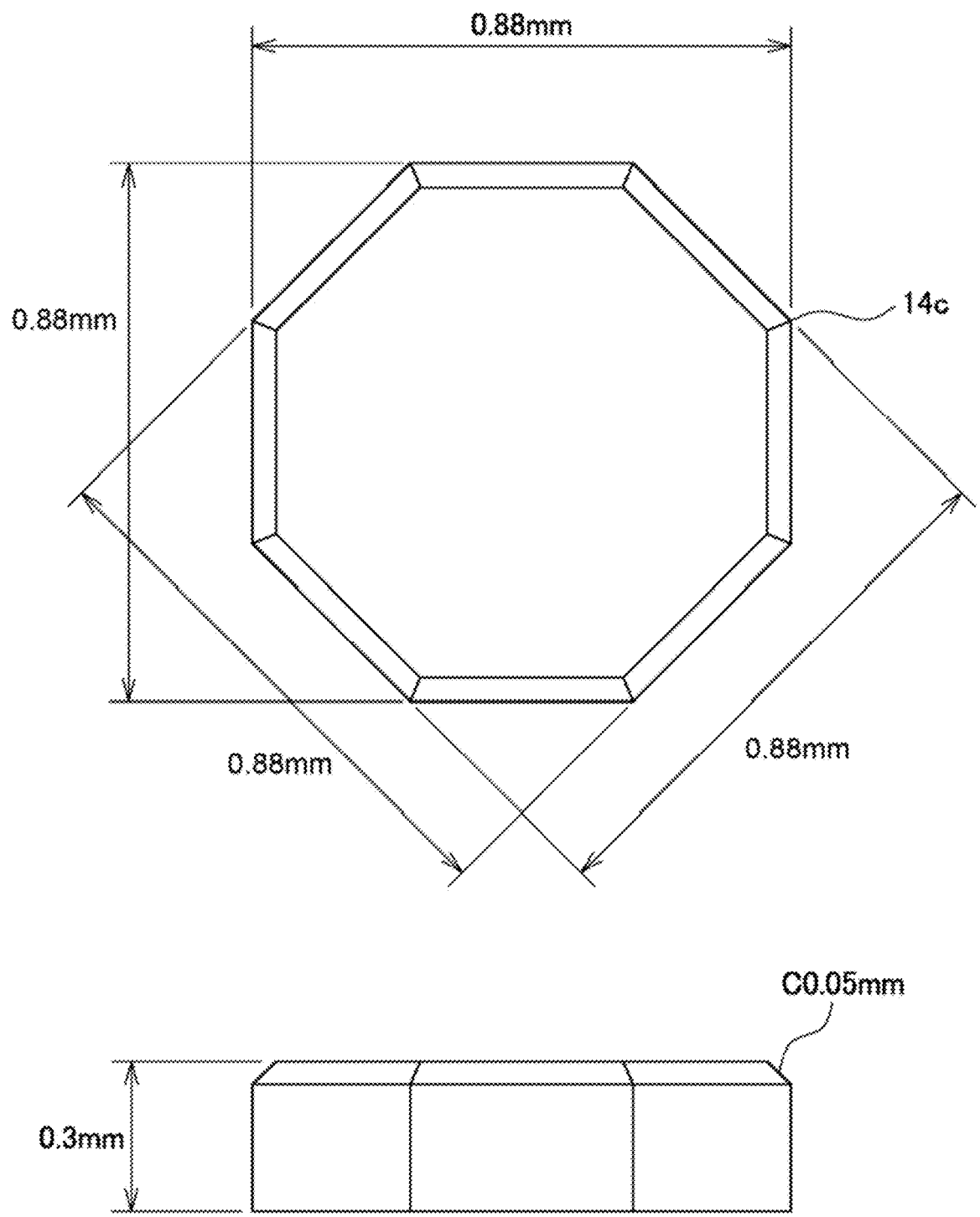
FIG. 20 is a diagram showing calculated outer shape, thickness and length of chamfered surface C in a radial direction of the cover member.

$P_{T1} \geq EFD_T/2$
$P_{T2} \geq EFD_T/2$
$P_{T3} \geq EFD_T/2$
$P_{T4} \geq EFD_T/2$
$P_{T5} \geq EFD_T/2$
$P_{T6} \geq EFD_T/2$
$P_{T7} \geq EFD_T/2$
$P_{T8} \geq EFD_T/2$ FIG. 19 is a diagram continued from FIG. 18 for explaining an example of the calculation of various values related to the cover member 14c. FIG. 20 is a diagram showing calculated outer shape, thickness and length of chamfered surface C in a radial direction of the cover member 14c. The objects indicated by each symbol shown in FIG. 19 are as follows.

$ID_{HL}$: Inner diameter of holder 11a $OD_{HL}$: Outer diameter of holder 11a $W_{HL}$: Thickness of body portion 15 of holder 11a $CL_{T1}$: Variation tolerance area of apexes (corners) of cover member 14c $CL_{T2}$: Variation tolerance area of front end surface 29 of cover member 14c EBD: Diameter of effective area 37 of light beam $EFD_T$: Light receiving area 38 of front end surface 29 of cover member 14c $D_{TVT1}$: Length (vertical) of outer shape of front end surface 29 of cover member 14c $D_{THL1}$: Length (horizontal) of outer shape of front end surface 29 of cover member 14c $D_{TDG1}$: Length (oblique) of outer shape of front end surface 29 of cover member 14c $D_{TDG2}$: Length (oblique) of outer shape of front end surface 29 of cover member 14c $OD_{TCG1}$: Length (diagonal) of outer shape of cover member 14c $OD_{TCG2}$: Length (diagonal) of outer shape of cover member 14c $OD_{TCG3}$: Length (diagonal) of outer shape of cover member 14c $OD_{TCG4}$: Length (diagonal) of outer shape of cover member 14c The length (size) of each part of the cover member 14c is determined based on the diameter EBD of the effective area 37 of the light beam. $D_{TVT1}$, $D_{THL1}$, $D_{TDG1}$ and $D_{TDG2}$ follow the conditions below, and $OD_{TCG1}$, $OD_{TCG2}$, $OD_{TCG3}$ and $OD_{TCG4}$ follow the conditions below.

$D_{TVT1} \geq EFD_T \geq EBD + CL_{T1}$
$D_{THL1} \geq EFD_T \geq EBD + CL_{T1}$
$D_{TDG1} \geq EFD_T \geq EBD + CL_{T1}$
$D_{TDG2} \geq EFD_T \geq EBD + CL_{T1}$
$ID_{HL} \geq OD_{TCG1} \geq EFD_T + CL_{T2}$
$ID_{HL} \geq OD_{TCG2} \geq EFD_T + CL_{T2}$
$ID_{HL} \geq OD_{TCG3} \geq EFD_T + CL_{T2}$
$ID_{HL} \geq OD_{TCG4} \geq EFD_T + CL_{T2}$ The size of the cover member 14c is determined by the above described conditions. In addition, the size of the outer diameter of the holder 11a is determined by the following (Formula 2).

$$OD_{HL} = ID_{HL} + W_{HL} \quad \text{(Formula 2)}$$

The length $C_T$ of the chamfered surface C in a radial direction and the thickness of the body portion 15 of the holder 11a are specified within the following range.

Length of chamfered surface C of cover member 14b: $0 \text{ mm} \leq C_T \leq 0.3$ mm Thickness of body portion 15 of holder 11a: $0.01 \text{ mm} \leq W_{HL} \leq 1$ mm A tolerance is determined considering the processing method of the cover member 14c. At that time, be sure to confirm that the size is not out of the range explained in FIG. 18.

Concrete examples of the calculation of various values related to the cover member 14c having a regular hexagonal prism shape are shown below. The conditions of the concrete examples of the calculation of various values are same as the conditions of the concrete examples of the calculation of various values in the cover member 14a formed in the regular quadrangular prism. Note that the diameter EBD (EBD=0.7 mm) of the effective area 37 of the light beam and the light receiving area 38 ($EFD_H$=0.78 mm) of the front end surface 29 of the cover member 14c are same as those of the cover member 14a of the regular quadrangular prism.

(1) Calculation of outer shape of cover member 14c $$\begin{aligned} D_{TVT2} &= D_{THL2} \\ &= D_{TDG3} \\ &= D_{TDG4} \\ &= D_{THL1} + C_T * 2 \\ &= 0.78 + 0.05 * 2 \\ &= 0.88 \text{ mm} \end{aligned}$$

(2) Calculation of length of diagonal line of cover member 14c $$\begin{aligned} OD_{TCG} &= 2 * (D_{THL2}/2) / \cos 22.5° \\ &= 2 * (0.88/2) / \cos 22.5° \\ &\approx 0.813 \text{ mm} \end{aligned}$$

(3) Calculation of inner diameter of holder 11a $$\begin{aligned} ID_{HL} &= OD_{TCG} + CL_{T1} * 2 \\ &= 0.813 + 0.04 * 2 \\ &= 0.893 \text{ mm} \end{aligned}$$

(4) Calculation of outer diameter of body portion 15 of holder 11a $$OD_{HL} = ID_{HL} + W_{HL} * 2$$
$$= 0.893 + 0.1 * 2$$
$$= 1.093 \text{ mm}$$

As the calculated size of the cover member 14c, as shown in FIG. 20, the outer shape of the cover member 14c is 0.88 mm, the thickness of the cover member 14c is 0.3 mm, and the length of the chamfered surface C in a radial direction is 0.05 mm.

In the lens unit 10F, the side surfaces 31 of the cover member 14c (cover glass or cover plastic) continuing from the front end surface 29 to the rear end surface 30 can be easily formed in the regular octagonal prism (octagonal prism) by cutting a glass material or molding a synthetic resin material. Unlike the conventional lens unit 50 shown in FIGS. 26 and 27, handwork of artisans is not required for polishing the outer peripheral surface of the cover glass 55 so that the cover glass 55 has a complete round cross-sectional shape. Accordingly, the lens unit 10F having the cover member 14c formed in a regular octagonal prism (octagonal prism) can be mechanically and efficiently manufactured.

In the lens unit 10F, the cover member 14c (cover glass or cover plastic) can be manufactured by cutting a glass material in the regular octagonal prism (octagonal prism) or molding a synthetic resin material into the regular octagonal prism (octagonal prism). Thus, the cover member 14c can be manufactured at low cost without depending on skilled artisans. In addition, the lens unit 10F having the cover member 14c which is formed in the regular octagonal prism (octagonal prism) and does not cause deviation in precision can be manufactured at low cost. Accordingly, production efficiency of the lens unit 10F can be increased.

In the lens unit 10F, the tips of at least two of eight corners 32 of the regular octagonal prism (octagonal prism) of the cover member 14c (cover glass or cover plastic) are in contact with the inner peripheral surface 27 of the body portion 15 of the holder 11a. Thus, the cover member 14c formed in the regular octagonal prism can be fixed to the housing space 17 of the body portion 15 of the holder 11a while preventing the cover member 14c from moving in the housing space 17 of the body portion 15 of the holder 11a.

In the lens unit 10F, the circular effective area 37 (EBD) of the light beam is located inside the light receiving area 38 having the regular octagonal shape (octagonal shape) surrounded by the outer peripheral edge of the front end surface 29 of the cover member 14c (cover glass or cover plastic). Thus, a part of the effective area 37 (EBD) of the light beam is not displaced (protruded) outside the light receiving area 38 having a regular octagonal shape. Accordingly, the accurate image can be formed on the lens unit 10F.

In the lens unit 10F, when the side surfaces 31 of the cover member 14c (cover glass or cover plastic) are formed in the regular octagonal prism (octagonal prism), the corners can be easily chamfered by cutting the corners where the front end surface 29 of the cover member 14c and each of the eight side surfaces 31 intersect or the corners can be easily chamfered by molding the synthetic resin material. Accordingly, unexpected breakage and damage of the corners of the cover member 14c can be prevented by chamfering the corners of the cover member 14c.

When tips of at least one of eight corners 32 of the cover member 14c formed in the regular octagonal prism (octagonal prism) is separated inward in a radial direction from the inner peripheral surface 27 of the housing space 17 of the body portion 15 of the holder 11a at a predetermined separate distance, if the predetermined separate distance between the tips of the corners 32 and the inner peripheral surface 27 of the housing space 17 exceeds 0.1 mm, a part of the circular effective area 37 (EBD) of the light beam may be displaced (protruded) outside the light receiving area 38 having the regular octagonal shape (octagonal shape) surrounded by the outer peripheral edge of the front end surface 29 of the cover member 14c when the cover member 14c is moved in the housing space 17 of the body portion 15 of the holder 11a. In such a case, the accurate image cannot be formed on the lens unit 10F. However, since the predetermined separate distance between the tips of the corners 32 and the inner peripheral surface 27 of the housing space 17 of the body portion 15 of the holder 11a is within the range of 0.1 mm or less and preferably 0.01 mm to 0.1 mm in the lens unit 10F, a part of the effective area 37 (EBD) of the light beam is not displaced (protruded) outside the light receiving area 38 of the front end surface 29 of the cover member 14c even when the cover member 14c (cover glass or cover plastic) is moved in the housing space 17 of the body portion 15 of the holder 11a. Thus, the effective area 37 (EBD) of the light beam can be located inside the light receiving area 38 of the front end surface 29 of the cover member 14c. Accordingly, the accurate image can be formed on the lens unit 10F.

If the length $C_T$ of the chamfered surface C exceeds 0.3 mm in a radial direction, the light receiving area 38 having the regular octagonal shape (octagonal shape) surrounded by the outer peripheral edge of the front end surface 29 of the cover member 14c becomes small and a part of the effective area 37 (EBD) of the light beam may be located (displaced) outside the light receiving area 38 having the regular octagonal shape (octagonal shape) surrounded by the outer peripheral edge of the front end surface 29 of the cover member 14c. Thus, the accurate image cannot be formed on the lens unit 10F. However, since the length $C_T$ of the chamfered surface C of the lens unit 10F is 0.3 mm or less in the radial direction and preferably 0.05 mm to 0.3 mm, the effective area 37 (EBD) of the light beam can be located inside the light receiving area 38 having the regular octagonal shape (octagonal shape) surrounded by the outer peripheral edge of the front end surface 29 of the cover member 14c (cover glass or cover plastic). Thus, the accurate image can be formed on the lens unit 10F while preventing a part of the effective area 37 (EBD) of the light beam from being located (displaced) outside the light receiving area 38 of the front end surface 29 of the cover member 14c.

Figure 21:
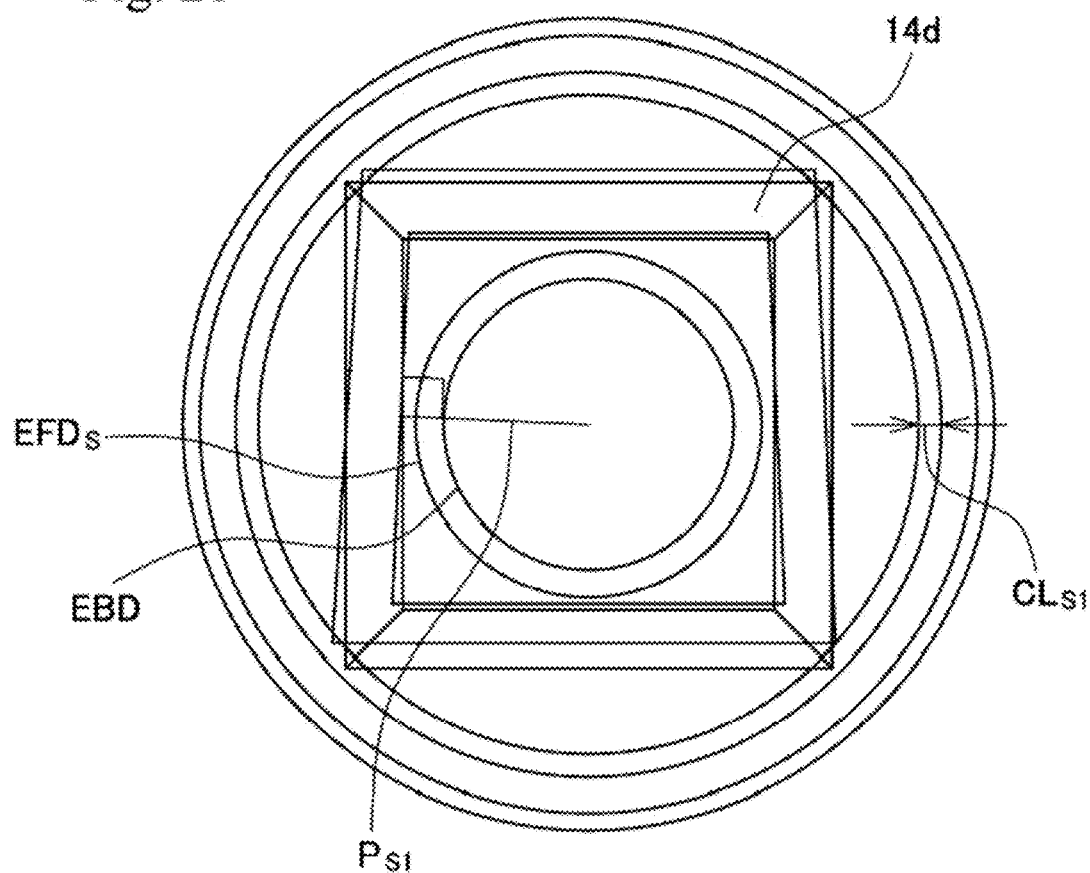
FIG. 21 is a diagram for explaining an example of the calculation of various values related to a cover member having a trapezoidal plane shape.
Figure 21:
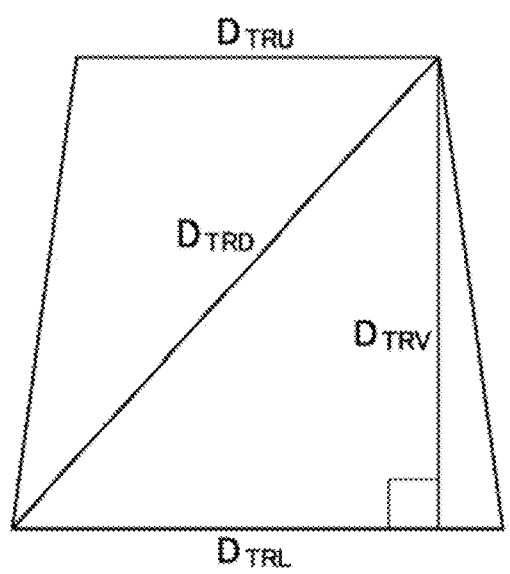
Figure 22:
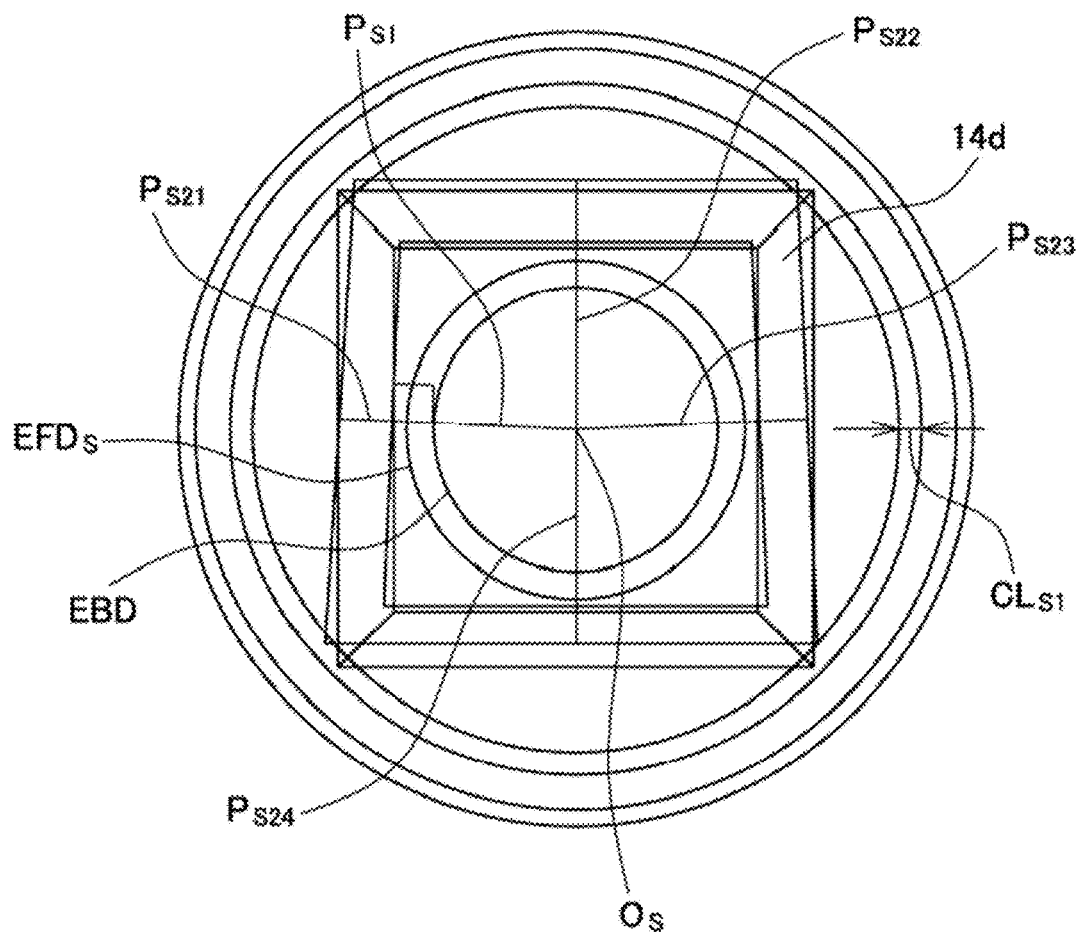
FIG. 22 is a diagram continued from FIG. 21 for explaining an example of the calculation of various values related to the cover member.
Figure 22:
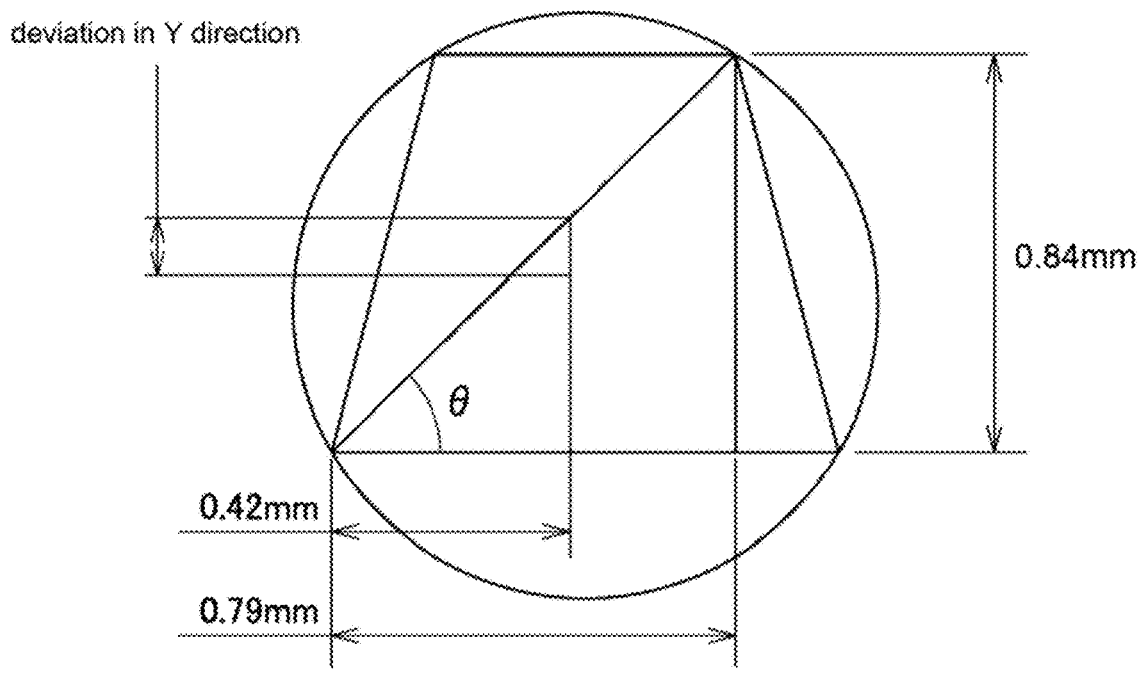
Figure 23:
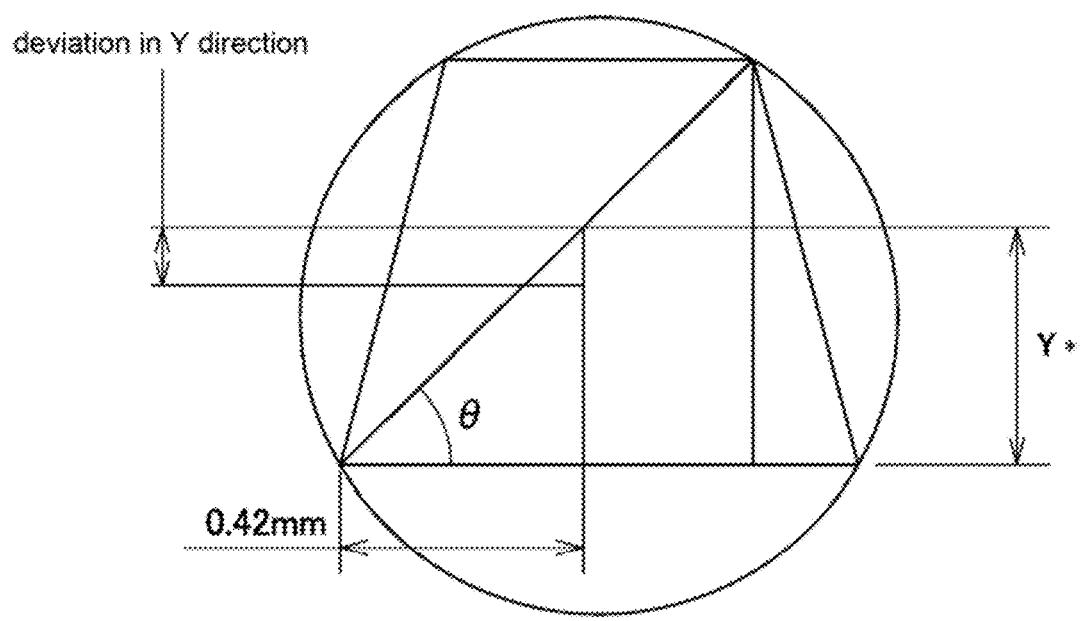
FIG. 23 is a diagram continued from FIG. 22 for explaining an example of the calculation of various values related to the cover member.
Figure 24:
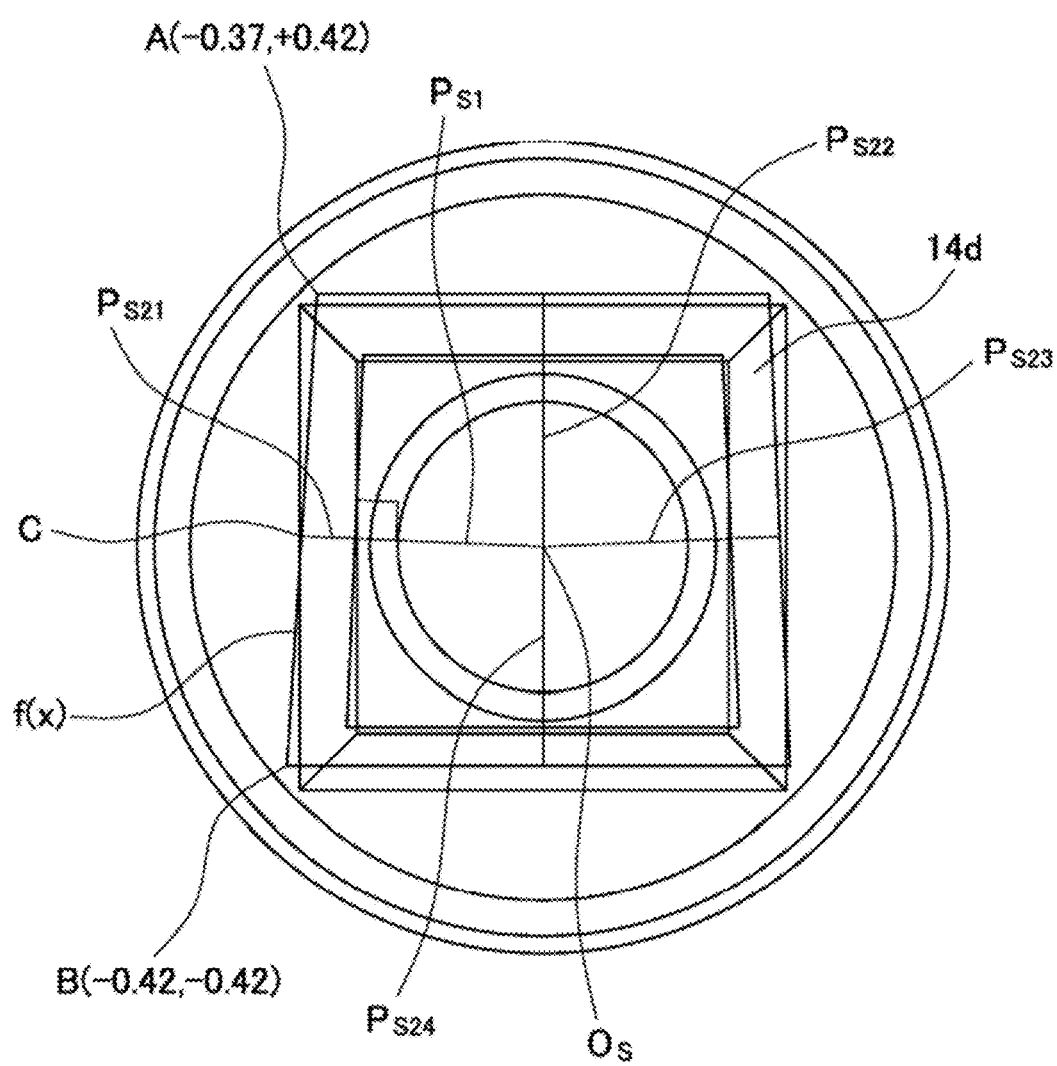
FIG. 24 is a diagram continued from FIG. 23 for explaining an example of the calculation of various values related to the cover member.
Figure 25:
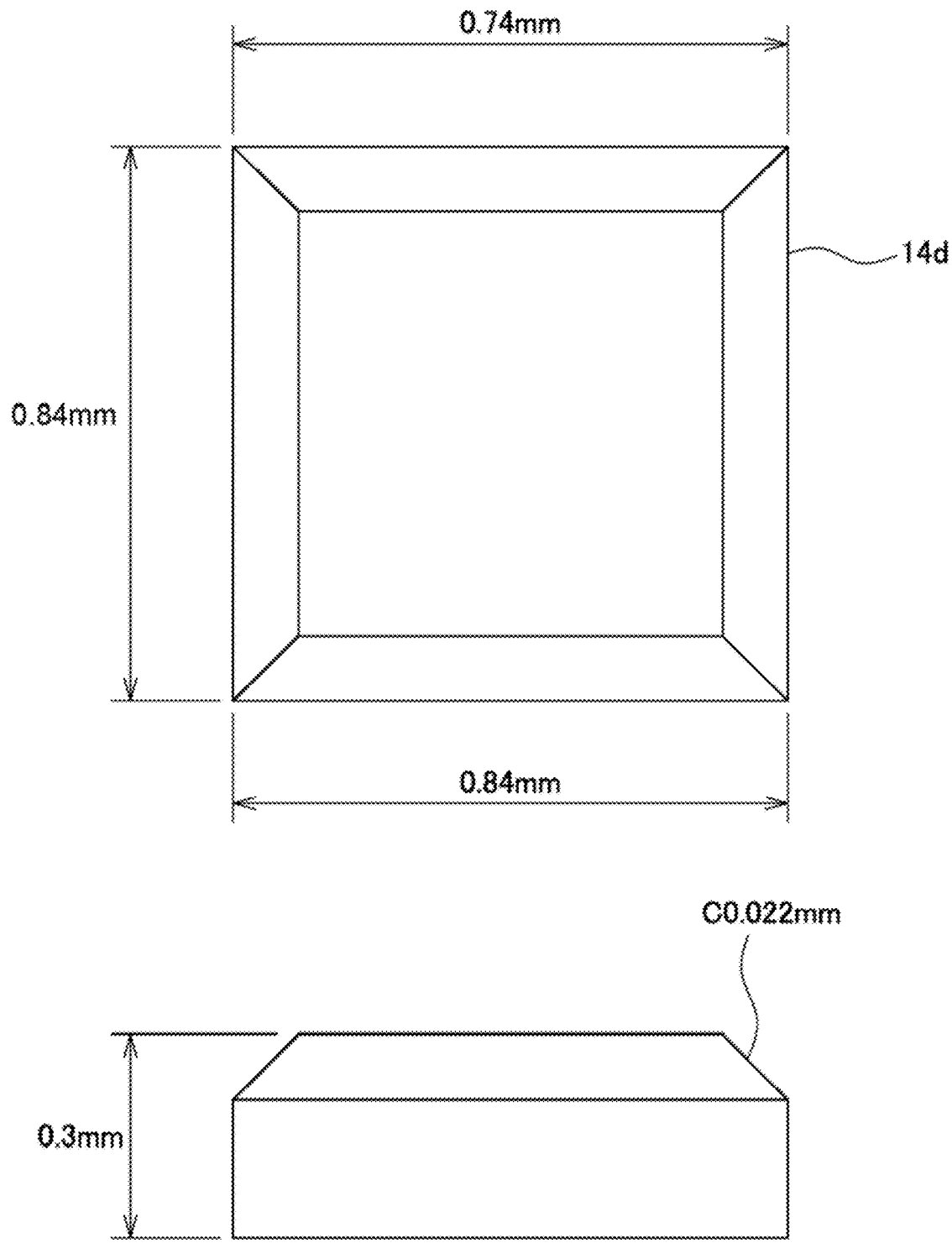
FIG. 25 is a diagram showing upper base, lower base, feet, thickness and length of chamfered surface C in a radial direction of the cover member.

FIG. 21 is a diagram for explaining an example of the calculation of various values related to a cover member 14d having a trapezoidal plane shape. FIG. 22 is a diagram continued from FIG. 21 for explaining an example of the calculation of various values related to the cover member 14d. FIG. 23 is a diagram continued from FIG. 22 for explaining an example of the calculation of various values related to the cover member 14d. FIG. 24 is a diagram continued from FIG. 23 for explaining an example of the calculation of various values related to the cover member 14d. FIG. 25 is a diagram showing upper base, lower base, feet, thickness and length of chamfered surface C in a radial direction of the cover member 14d.

The various values related to the cover member 14d formed in a trapezoidal prism (quadrangular pyramid) are calculated based on the calculation of the various values related to the cover member 14a formed in the regular quadrangular prism (quadrangular prism) explained based on FIGS. 5 and 6. When the shape shown in FIG. 21 is assumed, the upper base is relatively small (short) compared to the regular quadrangular shape. If the upper base is smaller by 0.1 mm, the diagonal line of the trapezoidal shape (isosceles trapezoid) can be calculated as follows.

$$DTRD = \sqrt{((\text{upper base} + 0.1/2)^{\wedge}2 + \text{height}^{\wedge}2)}$$
$$= \sqrt{((DTRU + 0.1/2)^{\wedge}2 + DTRV^{\wedge}2)}$$
$$= \sqrt{((0.78 + 0.1/2)^{\wedge}2 + 0.88^{\wedge}2)}$$
$$\approx 1.210\ m$$

Since the inner diameter $ID_{HL}$ of the body portion 15 of the holder 11a is 1.325 mm, a clearance between the cover member 14d and the inner peripheral surface 27 of the body portion 15 of the holder 11a is out of the range of $CL_{S1} \leq 0.1$ mm.
$CL_{S1}$=1.325-1.210=0.115 mm
In this case, it should be considered to reduce the clearance between the cover member 14d and the inner peripheral surface 27 of the body portion 15 of the holder 11a, for example. When $CL_{S1}$=0.02 mm, the inner diameter of the body portion 15 of the holder 11a becomes 1.228 mm. Since the size of the cover member 14d is changed, $CL_{S1}$ is within the range of $CL_{S1} \leq 0.1$ mm.
$CL_{S1}$=1.228-1.153=0.075 mm Then, the apexes of the front end surface 29 of the cover member 14d (length Cs of the chamfered surface C in a radial direction) will be considered. As shown in FIG. 22, lines $PS_{21}$ to $PS_{24}$ which are perpendicularly drawn from the center $O_S$ of the front end surface 29 of the cover member 14d to the outer peripheral sides of the cover member 14d are as follows. A circumscribed circle of the trapezoidal shape is drawn.

If the circumscribed circle is supposed as the inner diameter $ID_{HL}$ of the body portion 15 of the holder 11a, the center of the circumscribed circle and the center (the position equally distanced from four apexes) of the trapezoidal shape are displaced with each other. The amount of the above described displacement should be preliminarily taken into consideration. Since the cover member 14d is formed in a trapezoidal shape and the upper base is shorter by 0.1 mm than the lower base, the center of the trapezoidal shape is not laterally displaced with respect to the center of the circumscribed circle.

The displacement in the vertical direction (displacement in Y-axis direction) (shown in FIG. 23) is as follows.

$$\theta = \arctan(0.84/0.79) \approx 46.757°$$

A displacement between an intersection of two diagonals in this angle and the center of the circle is the amount of the displacement between the trapezoidal shape and the circle. Thus, the displacement in the Y-direction in the center (the position of X=0.42 mm from the apex) of the diagonal line having an angle of 46.757° is confirmed. Since the displacement from the center of the circle is not generated at all when the shape is the regular quadrangular shape (i.e., the angle of the diagonal line is 45°), amount of the displacement from 45° is calculated.

$$YS = 0.42 * \tan 45°$$
$$= 0.42\ \text{mm (in case of the regular quadrangular shape)}$$

-continued $$YTR = 0.42 * \tan 46.757°$$
$$= 0.446\ \text{mm (in case of the trapezoidal shape)}$$
$$YS - YTR = 0.42 - 0.446 = -0.026\ \text{mm}$$

As explained above, the displacement of 0.026 mm is calculated.

Therefore, the length of the chamfered surface C in the trapezoidal shape should be shorter than target value of the regular quadrangular shape by 0.026 mm or more. Alternatively, if the size of the cover member 14d can be increased, it is also possible to increase the size of the cover member 14d by 0.026 mm or more.

Note that the length (size) of the chamfered surface C is adjusted here.

$PS_{21}$ to $PS_{24}$ shown in FIG. 24 will be calculated.

When $O_S$ is considered as the point of origin (0, 0), the coordinates of the apex A and the apex B are shown in FIG. 24.

The function f(X) of the line connecting the point A and the point B will be calculated.
 −0.42=−0.42*a+b
 0.42=−0.37*a+b
 a=84/5
 b=0.42+0.37*84/5

Accordingly, the formula expressing the line connecting the point A and the point B is as follows.

$$f(X)=84/5*X+0.42+0.37*84/5$$

In addition, $PS_{21}$ which is orthogonal to the function f(X) at the point C and passes through the point of origin is expressed by the following formula.

$$PS_{21}=-5/84*X$$

From the formula of $PS_{21}$, the coordinate of the point C is calculated.

$$X=-0.394, Y=0.023$$

Therefore, the length of $PS_{21}$ is 0.395 mm.

Since $PS_{21}=PS_{23}$, $PS_{23}$ is also 0.395 mm. In addition, since $PS_{22}$ and $PS_{24}$ are a half of 0.84 mm, $PS_{22}$ and $PS_{24}$ are 0.42 mm. Here, the displacement between the center of the circle and the center of the trapezoidal shape will be considered. It is already known from the above described calculation that the center is displaced in the Y-direction by 0.026 mm. Thus, the following result is obtained. 0.42 mm-0.026 mm=0.394 mm From the above described result, it is known that the minimum distance from the center of the effective area 37 of the light beam to the front end surface (planar part) of the cover member 14d of the front end surface is 0.394 mm. When the minimum distance is compared with the effective area (0.7 mm/2=0.35 mm) of the light beam, the following result is obtained.

$$0.394-0.35=0.044\ \text{mm}$$

Thus, the length available for using as the chamfered surface C is 0.022 mm which is a half of 0.044 mm.

As shown in FIG. 25, the calculated sizes of the cover member 14d are as follows. In the cover member 14d formed in the isosceles trapezoid, the upper base is 0.74 mm, the lower base is 0.84 mm, the feet is 0.84 mm, the thickness of the cover member 14d is 0.3 mm and length of the chamfered surface C in the radial direction is 0.022 mm.

DESCRIPTION OF THE REFERENCE NUMERALS 10A to 10F: lens unit
11a to 11c: holder
12: lens
13: copper diaphragm plate (diaphragm means)
14a to 14d: cover member
15: body portion
16: leg portion
17: housing space
18: sensor module housing space
19: front end
20: rear end
21: lens portion
22: flange portion
23: front end surface of lens
24: rear end surface of lens
25: side surfaces of lens
26: flange abutting portion
27: inner peripheral surface
28: diaphragm (diaphragm aperture)
29: front end surface of cover member
30: rear end surface of cover member
31: side surfaces of cover member
32: corner of cover member
33: chamfered surface of cover member
34: gap
35: adhesive material (filler)
36: sensor module
37: effective area
38: light receiving area
39: diaphragm pattern (diaphragm means)
40: marking protrusion
41: marking protrusion

What is claimed is:

1. A lens unit, comprising:
a holder having a housing space;
a lens;
a diaphragm means; and
a cover member, wherein
the lens, the diaphragm means and the cover member are housed individually in the housing space having a circular cross-section,
side surfaces of the cover member are formed in a polygonal prism with even-numbered corners, the side surfaces continuing from a front end surface to a rear end surface which is located nearer to the lens,
at least two of the corners of the polygonal prism are in contact with an inner peripheral surface of the housing space of the holder for housing the cover member,
a gap is formed between each of the side surfaces of the cover member and the inner peripheral surface of the holder in the lens unit,
an effective area of a light beam is located inside a light receiving area having a polygonal shape surrounded by a peripheral edge of the front end surface of the cover member,
the outermost shape of the cross-sectional shape of the lens cut perpendicular to an optical axis direction is different from the outermost shape of the cross-sectional shape of the cover member cut perpendicular to the optical axis direction,
a gap is formed between an outer periphery of the lens and an inner peripheral surface of the holder, and
the outermost shape of the cross-sectional shape of the lens cut perpendicular to the optical axis direction is a circular shape.

2. The lens unit according to claim 1, wherein
the side surfaces of the cover member are formed in a quadrangular prism, the side surfaces continuing from the front end surface to the rear end surface,
at least two of the corners of the quadrangular prism of the cover member are in contact with the inner peripheral surface of the housing space,
the gap is formed between each of the side surfaces of the quadrangular prism of the cover member and the inner peripheral surface of the holder in the lens unit, and
the effective area of the light beam is circular and located inside the light receiving area having a quadrangular shape surrounded by the peripheral edge of the front end surface of the quadrangular prism of the cover member.

3. The lens unit according to claim 1, wherein
the side surfaces of the cover member are formed in a hexagonal prism, the side surfaces continuing from the front end surface to the rear end surface,
at least two of the corners of the hexagonal prism of the cover member are in contact with the inner peripheral surface of the housing space,
the gap is formed between each of the side surfaces of the hexagonal prism of the cover member and the inner peripheral surface of the holder in the lens unit, and
the effective area of the light beam is circular and located inside the light receiving area having a hexagonal shape surrounded by the peripheral edge of the front end surface of the hexagonal prism of the cover member.

4. The lens unit according to claim 1, wherein
the side surfaces of the cover member are formed in an octagonal prism, the side surfaces continuing from the front end surface to the rear end surface,
at least two of the corners of the octagonal prism of the cover member are in contact with the inner peripheral surface of the housing space,
the gap is formed between each of the side surfaces of the octagonal prism of the cover member and the inner peripheral surface of the holder in the lens unit, and
the effective area of the light beam is circular and located inside the light receiving area having an octagonal shape surrounded by the peripheral edge of the front end surface of the octagonal prism of the cover member.

5. The lens unit according to claim 1, wherein
the cover member is chamfered at the corners where the front end surface and each of the side surfaces intersect so that a chamfered surface is formed between the front end surface and the side surfaces of the cover member.

6. The lens unit according to claim 5, wherein
a length of the chamfered surface of the cover member is 0.3 mm or less in a radial direction.

7. The lens unit according to claim 1, wherein
an inner diameter of the housing space of the holder for housing the cover member is 0.4 mm to 8 mm.

8. The lens unit according to claim 1, wherein
a thickness from the front end surface to the rear end surface of the cover member is 0.01 mm to 0.5 mm.

9. The lens unit according to claim 1, wherein
an inner diameter of a diaphragm in the diaphragm means is 0.01 mm to 0.3 mm, and
a field angle of the lens is 150° or less.

10. The lens unit according to claim 1, wherein
a marking protrusion extending from the inner peripheral surface of the holder inward in a radial direction is extended to the gap formed between the side surfaces of the cover member and the inner peripheral surface of the holder.

11. The lens unit according to claim 1, wherein
a filler is filled in the gap formed between each of the side surfaces of the cover member and the inner peripheral surface of the holder.

12. The lens unit according to claim 1, wherein
the diaphragm means is a diaphragm pattern masked by photo-etching at least on one of the front end surface and the rear end surface of the cover member.

13. The lens unit according to claim 1, wherein
the lens unit is installed on a distal end of a sensor module of an endoscope.

14. The lens unit according to claim 3, wherein
when at least one of the corners of the cover member is separated inward in a radial direction from the inner peripheral surface of the housing space at a predetermined separate distance in the lens unit, the predetermined separate distance between the corners and the inner peripheral surface of the housing space is 0.1 mm or less.

15. The lens unit according to claim 2, wherein
an inner diameter of the housing space of the holder for housing the cover member is 0.4 mm to 8 mm.

16. The lens unit according to claim 3, wherein
an inner diameter of the housing space of the holder for housing the cover member is 0.4 mm to 8 mm.

17. The lens unit according to claim 1, wherein
the diaphragm means is a plate having a disk shape fitted in the housing space.

* * * * *